United States Patent
Diolaiti et al.

(10) Patent No.: US 8,620,473 B2
(45) Date of Patent: Dec. 31, 2013

(54) MEDICAL ROBOTIC SYSTEM WITH COUPLED CONTROL MODES

(75) Inventors: Nicola Diolaiti, Palo Alto, CA (US); David Q. Larkin, Menlo Park, CA (US); Catherine J. Mohr, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 654 days.

(21) Appl. No.: 12/780,071

(22) Filed: May 14, 2010

(65) Prior Publication Data

US 2010/0274087 A1   Oct. 28, 2010

Related U.S. Application Data

(63) Continuation-in-part of application No. 11/762,200, filed on Jun. 13, 2007, now Pat. No. 7,725,214, and a continuation-in-part of application No. 12/489,566, filed on Jun. 23, 2009, and a continuation-in-part of application No. 12/613,328, filed on Nov. 5, 2009, which is a continuation-in-part of application No. 12/541,913, filed on Aug. 15, 2009.

(51) Int. Cl.
    *G06F 19/00* (2011.01)
(52) U.S. Cl.
    USPC ........... 700/245; 700/247; 700/248; 600/407; 600/424; 901/46
(58) Field of Classification Search
    USPC .......... 700/245, 247, 248, 250, 254; 600/407, 600/424; 901/46, 47
    See application file for complete search history.

(56) References Cited

U.S. PATENT DOCUMENTS

| | | |
|---|---|---|
| 4,644,237 A | 2/1987 | Frushour et al. |
| 4,791,934 A | 12/1988 | Brunnett |
| 4,831,549 A | 5/1989 | Red et al. |
| 4,837,703 A | 6/1989 | Kakazu et al. |
| 4,979,949 A | 12/1990 | Matsen, III |
| 5,230,338 A | 7/1993 | Allen et al. |
| 5,343,385 A | 8/1994 | Joskowicz et al. |
| 5,408,409 A | 4/1995 | Glassman et al. |

(Continued)

FOREIGN PATENT DOCUMENTS

| | | |
|---|---|---|
| EP | 812682 A1 | 12/1997 |
| EP | 1125557 A2 | 8/2001 |

(Continued)

OTHER PUBLICATIONS

PCT/US2011/036109 Invitation to Pay Additional Fees and Partial International Search Report, mailed Aug. 18, 2011, 5 pages.

(Continued)

*Primary Examiner* — Toan To

(57) ABSTRACT

In a coupled control mode, the surgeon directly controls movement of an associated slave manipulator with an input device while indirectly controlling movement of one or more non-associated slave manipulators, in response to commanded motion of the directly controlled slave manipulator, to achieve a secondary objective. By automatically performing secondary tasks through coupled control modes, the system's usability is enhanced by reducing the surgeon's need to switch to another direct mode to manually achieve the desired secondary objective. Thus, coupled control modes allow the surgeon to better focus on performing medical procedures and to pay less attention to managing the system.

46 Claims, 25 Drawing Sheets

(56) References Cited

U.S. PATENT DOCUMENTS

| | | | |
|---|---|---|---|
| 5,417,210 A | 5/1995 | Funda et al. |
| 5,528,955 A | 6/1996 | Hannaford et al. |
| 5,748,767 A | 5/1998 | Raab |
| 5,755,725 A | 5/1998 | Druais |
| 5,820,545 A | 10/1998 | Arbter et al. |
| 5,820,623 A | 10/1998 | Ng |
| 5,950,629 A | 9/1999 | Taylor et al. |
| 5,987,591 A | 11/1999 | Jyumonji |
| 6,120,433 A | 9/2000 | Mizuno et al. |
| 6,224,542 B1 | 5/2001 | Chang et al. |
| 6,325,808 B1 | 12/2001 | Bernard et al. |
| 6,398,726 B1 | 6/2002 | Ramans et al. |
| 6,459,926 B1 | 10/2002 | Nowlin et al. |
| 6,468,265 B1 | 10/2002 | Evans et al. |
| 6,493,608 B1 | 12/2002 | Niemeyer |
| 6,522,906 B1 | 2/2003 | Salisbury, Jr. et al. |
| 6,574,355 B2 | 6/2003 | Green |
| 6,645,196 B1 | 11/2003 | Nixon et al. |
| 6,659,939 B2 | 12/2003 | Moll et al. |
| 6,770,081 B1 | 8/2004 | Cooper et al. |
| 6,837,883 B2 | 1/2005 | Moll et al. |
| 6,926,709 B2 | 8/2005 | Bieger et al. |
| 6,991,627 B2 | 1/2006 | Madhani et al. |
| 7,155,315 B2 | 12/2006 | Niemeyer et al. |
| 7,194,118 B1 | 3/2007 | Harris et al. |
| 7,806,891 B2 * | 10/2010 | Nowlin et al. | 606/1 |
| 7,819,859 B2 * | 10/2010 | Prisco et al. | 606/1 |
| 7,963,913 B2 * | 6/2011 | Devengenzo et al. | 600/130 |
| 7,979,157 B2 | 7/2011 | Anvari |
| 8,062,288 B2 * | 11/2011 | Cooper et al. | 606/1 |
| 8,120,301 B2 * | 2/2012 | Goldberg et al. | 318/581 |
| 8,130,907 B2 * | 3/2012 | Maurer et al. | 378/65 |
| 8,155,479 B2 * | 4/2012 | Hoffman et al. | 382/276 |
| 8,170,716 B2 * | 5/2012 | Coste-Maniere et al. | 700/245 |
| 8,256,319 B2 * | 9/2012 | Cooper et al. | 74/490.01 |
| 8,315,720 B2 * | 11/2012 | Mohr et al. | 700/83 |
| 8,335,590 B2 * | 12/2012 | Costa et al. | 700/259 |
| 2001/0035871 A1 | 11/2001 | Bieger et al. |
| 2002/0045905 A1 | 4/2002 | Gerbi et al. |
| 2002/0120188 A1 | 8/2002 | Brock et al. |
| 2003/0055410 A1 | 3/2003 | Evans et al. |
| 2003/0109780 A1 | 6/2003 | Coste-Maniere et al. |
| 2004/0106916 A1 | 6/2004 | Quaid et al. |
| 2004/0238732 A1 | 12/2004 | State et al. |
| 2005/0059960 A1 | 3/2005 | Simaan et al. |
| 2005/0096502 A1 | 5/2005 | Khalili |
| 2006/0142657 A1 | 6/2006 | Quaid et al. |
| 2006/0241414 A1 | 10/2006 | Nowlin et al. |
| 2006/0258938 A1 | 11/2006 | Hoffman et al. |
| 2007/0013336 A1 | 1/2007 | Nowlin et al. |
| 2007/0038080 A1 | 2/2007 | Salisbury, Jr. et al. |
| 2007/0142968 A1 | 6/2007 | Prisco et al. |
| 2007/0265491 A1 | 11/2007 | Krag et al. |
| 2007/0270650 A1 | 11/2007 | Eno et al. |
| 2007/0283970 A1 | 12/2007 | Mohr et al. |
| 2007/0287884 A1 | 12/2007 | Schena |
| 2007/0287992 A1 | 12/2007 | Diolaiti et al. |
| 2008/0004603 A1 | 1/2008 | Larkin et al. |
| 2008/0033240 A1 | 2/2008 | Hoffman et al. |
| 2008/0065105 A1 | 3/2008 | Larkin et al. |
| 2008/0065109 A1 | 3/2008 | Larkin |
| 2008/0081992 A1 | 4/2008 | Kagermeier |
| 2008/0247506 A1 | 10/2008 | Maschke |
| 2009/0012531 A1 | 1/2009 | Quaid et al. |
| 2009/0036902 A1 | 2/2009 | DiMaio et al. |
| 2009/0088634 A1 | 4/2009 | Zhao et al. |
| 2009/0192524 A1 | 7/2009 | Itkowitz et al. |
| 2009/0326553 A1 | 12/2009 | Mustufa et al. |

FOREIGN PATENT DOCUMENTS

| | | |
|---|---|---|
| WO | WO2004014244 A2 | 2/2004 |
| WO | WO2006079108 A1 | 7/2006 |
| WO | 2007088208 A1 | 8/2007 |
| WO | WO2007136768 A2 | 11/2007 |
| WO | WO207146987 A2 | 12/2007 |
| WO | WO2008002830 A2 | 1/2008 |
| WO | WO2009034477 A2 | 3/2009 |
| WO | WO2009037576 A2 | 3/2009 |
| WO | WO2009158164 A1 | 12/2009 |
| WO | WO201039394 | 4/2010 |

OTHER PUBLICATIONS

PCT/U810/38246 International Search Report and Written Opinion of the International Searching Authority, mailed Sep. 14, 2010, 17 pages.

Christoforou, E.G. et al., "Robotic Arm for Magnetic Resonance Imaging Guided Interventions," 1st IEEE/RAS-EMBS International Conference on Biomedical Robotics and Biomechatronics, Feb. 20-22, 2006, pp. 911916.

PCT/US07/71850 International Search Report and Written Opinion of the International Searching Authority, mailed Feb. 13, 2009, 9 pages.

PCT/US09/46234 International Search Report and Written Opinion of the International Searching Authority, mailed Sep. 9, 2009, 13 pages.

PCT/US10/28897 International Search Report and Written Opinion of the International Searching Authority, mailed Jul. 19, 2010, 16 pages.

Vertut, Jean and Phillipe Coiffet, *Robot Technology: Teleoperation and Robotics Evolution and Development*, English translation Prentice-Hall, Inc., Inglewood Cliffs, NJ, USA 1986, vol. 3A, 332 pages.

PCT/US2011/036109 International Search Report and Written Opinion of the International Searching Authority, mailed Oct. 19, 2011, 16 pages.

Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.

Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.

\* cited by examiner

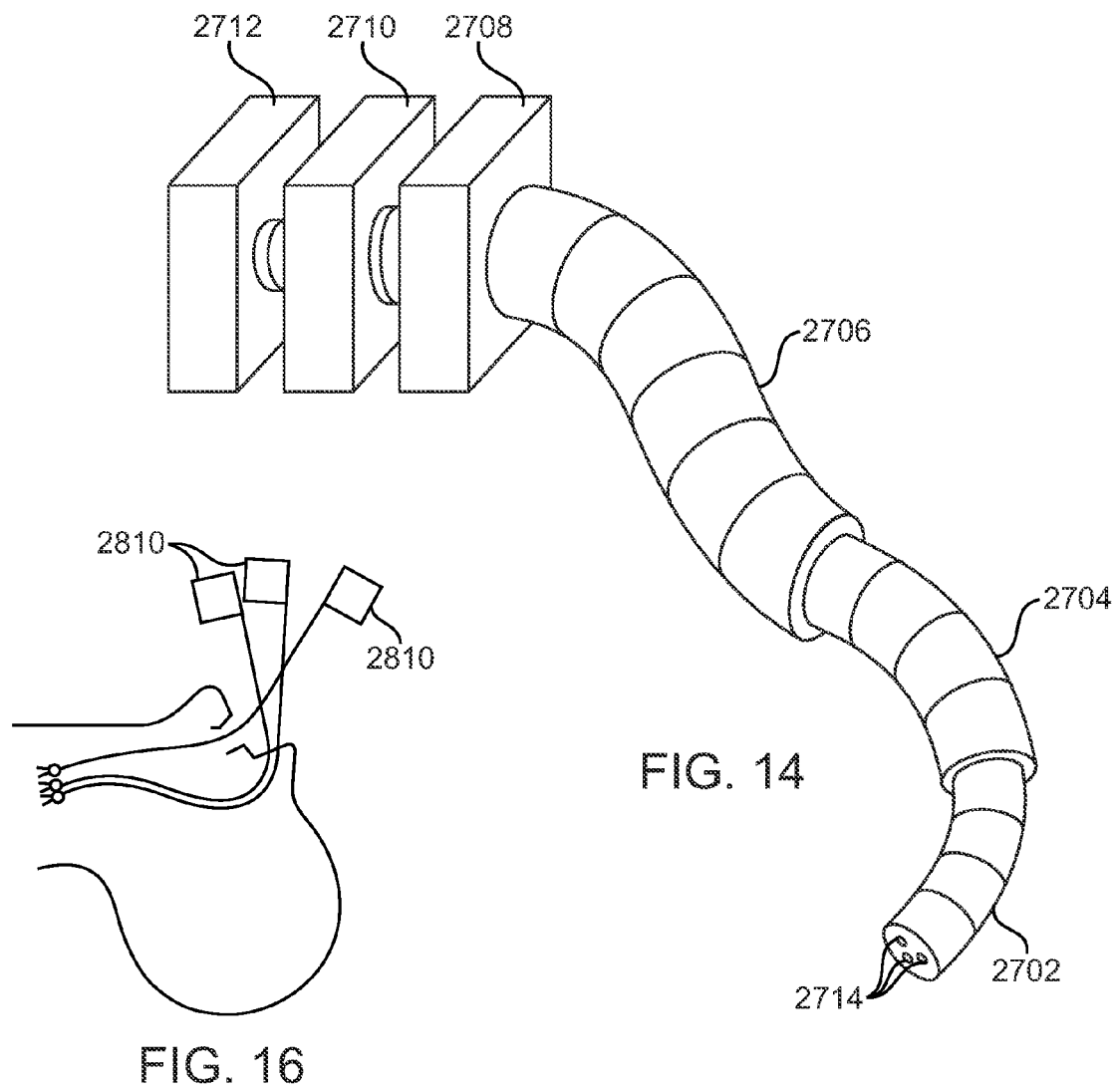
FIG. 14
FIG. 16
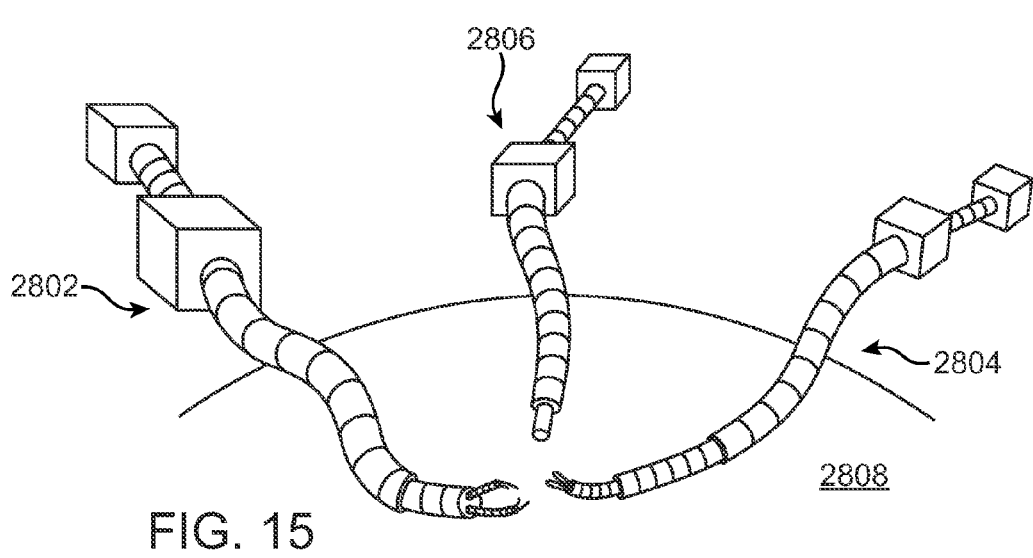
FIG. 15

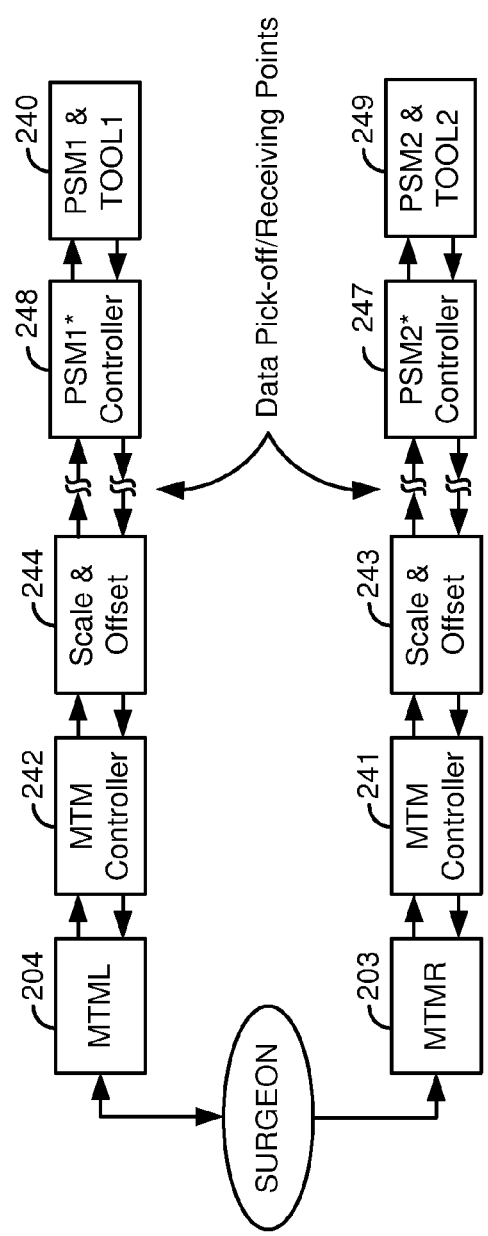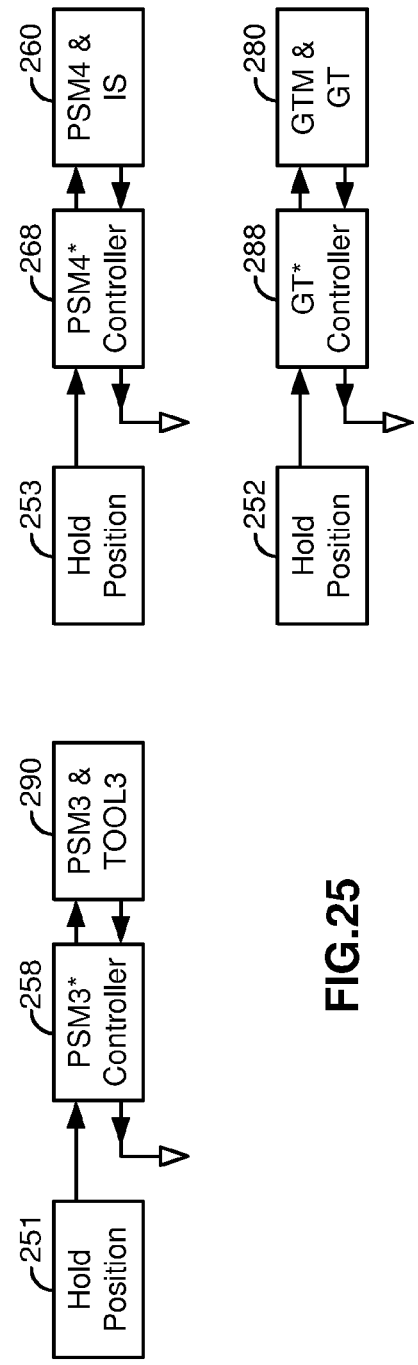
FIG.24
FIG.25

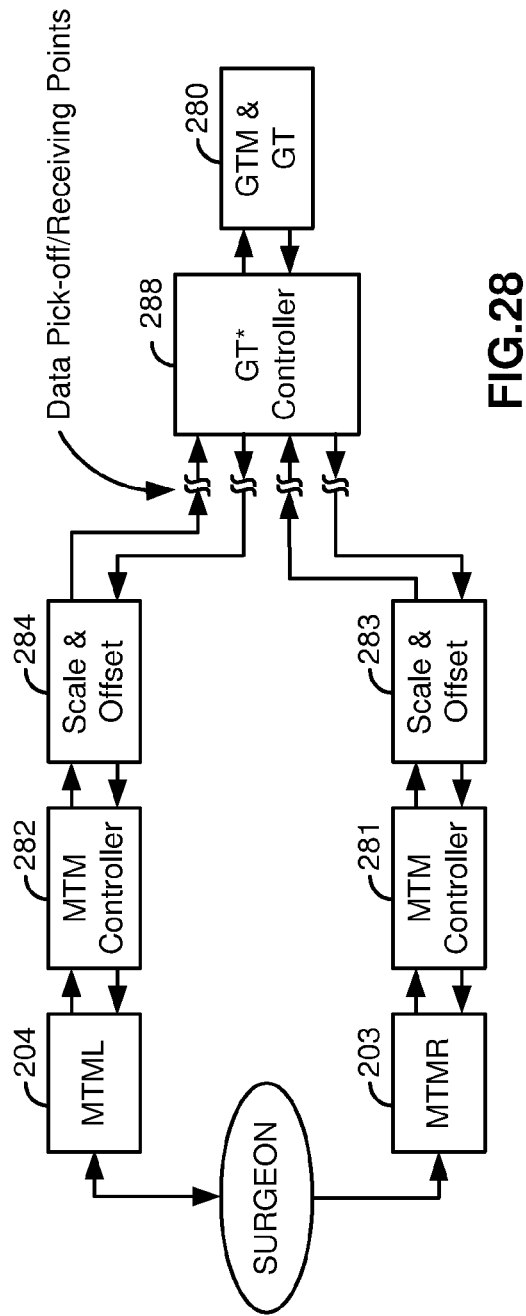
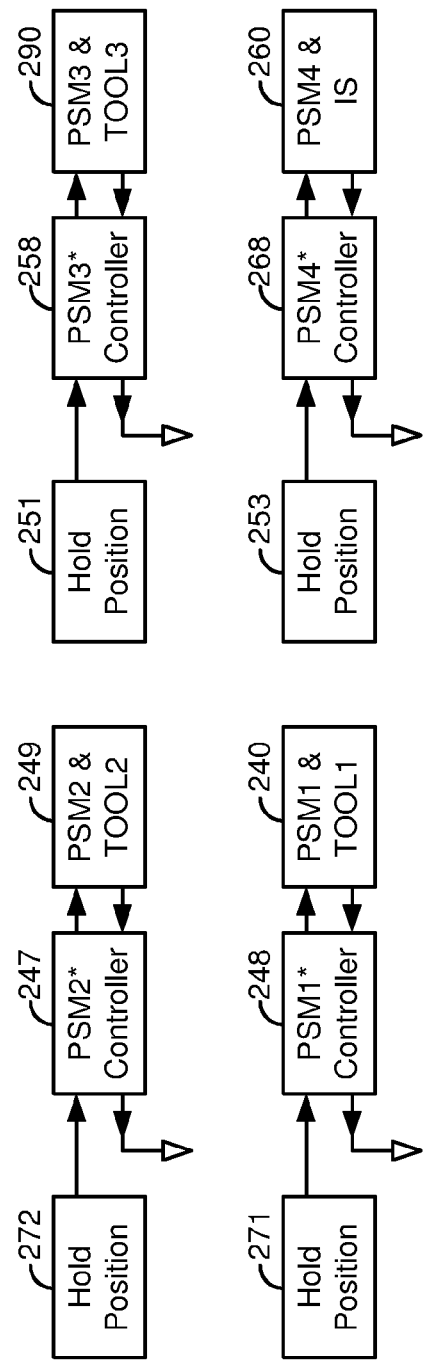
FIG.28
FIG.29

MEDICAL ROBOTIC SYSTEM WITH COUPLED CONTROL MODES

CROSS REFERENCE TO RELATED APPLICATIONS

This application is a continuation-in-part application of U.S. patent application Ser. No. 11/762,200 entitled "Minimally Invasive Surgical System" filed 13 Jun. 2007, which is incorporated herein by reference.

This application is also a continuation-in-part application of U.S. patent application No. 12/489,566 entitled "Medical robotic system providing an auxiliary view including range of motion limitations for articulatable instruments extending out of a distal end of an entry guide" filed 23 Jun. 2009 and a continuation-in-part application of U.S. patent application Ser. No. 12/613,328 entitled "Controller assisted reconfiguration of an articulated instrument during movement into and out of an entry guide" filed 5 Nov. 2009, which is a continuation-in-part of U.S. patent application Ser. No. 12/541,913 entitled "Smooth control of an articulated instrument across areas with different work space conditions" filed 15 Aug. 2009, all of which are incorporated by reference.

In addition, this application is related to the following U. S. patent applications, all of which are incorporated by reference:

U.S. patent application Ser. No. 11/762,217 entitled "Retraction of tissue for single port entry, robotically assisted medical procedures" by Mohr;

U.S. patent application Ser. No. 11/762,222 entitled "Bracing of bundled medical devices for single port entry, robotically assisted medical procedures" by Mohr et al.;

U.S. patent application Ser. No. 11/762,231 entitled "Extendable suction surface for bracing medical devices during robotically assisted medical procedures" by Schena;

U.S. patent application Ser. No. 11/762,236 entitled "Control system configured to compensate for non-ideal actuator-to-joint linkage characteristics in a medical robotic system" by Diolaiti et al.;

U.S. patent application Ser. No. 11/762,185 entitled "Surgical instrument actuation system" by Cooper et al.;

U.S. patent application Ser. No. 11/762,172 entitled "Surgical instrument actuator" by Cooper et al.;

U.S. patent application Ser. No. 11/762,165 entitled "Minimally invasive surgical system" by Larkin et al.;

U.S. patent application Ser. No. 11/762,161 entitled "Minimally invasive surgical instrument advancement" by Larkin et al.;

U.S. patent application Ser. No. 11/762,158 entitled "Surgical instrument control and actuation" by Cooper et al.;

U.S. patent application Ser. No. 11/762,154 entitled "Surgical instrument with parallel motion mechanism" by Cooper;

U.S. patent application Ser. No. 11/762,149 entitled "Minimally invasive surgical apparatus with side exit instruments" by Larkin;

U.S. patent application Ser. No. 11/762,170 entitled "Minimally invasive surgical apparatus with side exit instruments" by Larkin;

U.S. patent application Ser. No. 11/762,143 entitled "Minimally invasive surgical instrument system" by Larkin;

U.S. patent application Ser. No. 11/762,135 entitled "Side looking minimally invasive surgery instrument assembly" by Cooper et al.;

U.S. patent application Ser. No. 11/762,132 entitled "Side looking minimally invasive surgery instrument assembly" by Cooper et al.;

U.S. patent application Ser. No. 11/762,127 entitled "Guide tube control of minimally invasive surgical instruments" by Larkin et al.;

U.S. patent application Ser. No. 11/762,123 entitled "Minimally invasive surgery guide tube" by Larkin et al.;

U.S. patent application Ser. No. 11/762,120 entitled "Minimally invasive surgery guide tube" by Larkin et al.;

U.S. patent application Ser. No. 11/762,118 entitled "Minimally invasive surgical retractor system" by Larkin;

U.S. patent application Ser. No. 11/762,114 entitled "Minimally invasive surgical illumination" by Schena et al.;

U.S. patent application Ser. No. 11/762,110 entitled "Retrograde instrument" by Duval et al.;

U.S. patent application Ser. No. 11/762,204 entitled "Retrograde instrument" by Duval et al.;

U.S. patent application Ser. No. 11/762,202 entitled "Preventing instrument/tissue collisions" by Larkin;

U.S. patent application Ser. No. 11/762,189 entitled "Minimally invasive surgery instrument assembly with reduced cross section" by Larkin et al.;

U.S. patent application Ser. No. 11/762,191 entitled "Minimally invasive surgical system" by Larkin et al.; and U.S. patent application Ser. No. 11/762,196 entitled "Minimally invasive surgical system" by Duval et al.

BACKGROUND

1. Field of Invention

The present invention generally relates to medical robotic systems and in particular, to a medical robotic system providing coupled control modes.

2. Background Art

Minimally invasive surgery is known under various names (e.g., endoscopy, laparoscopy, arthroscopy, endovascular, keyhole, etc.), often specific to the anatomical area in which work is done. Such surgery includes the use of both hand-held and teleoperated/telemanipulated/telepresence (robot assisted/telerobotics) equipment, such as the da Vinci® Surgical System made by Intuitive Surgical, Inc. of Sunnyvale, Calif. Both diagnostic (e.g., biopsy) and therapeutic procedures ("medical procedures") are done. Instruments may be inserted into a patient percutaneously via surgical incision or via natural orifice. A new, experimental minimally invasive surgery variation is Natural Orifice Transluminal Endoscopic Surgery (NOTES), in which instruments enter via a natural orifice (e.g., mouth, nostril, ear canal, anus, vagina, urethra) and continue to a surgical site via a transluminal incision (e.g., in a gastric or colonic wall) within the body. Although teleoperative surgery using the da Vinci® Surgical System provides great benefits over, for instance, many hand-held procedures, for some patients and for some anatomical areas the da Vinci® Surgical System may be unable to effectively access a surgical site. In addition, further reducing the size and number of incisions generally aids patient recovery and helps reduce patient trauma and discomfort.

Various slave manipulators are provided in such medical robotic systems to perform useful functions, such as manipulating instruments to perform medical procedures on a patient, positioning and orienting imaging systems such as endoscopic imaging devices to capture images of the instruments' working ends, and delivering the working ends of the instruments and an image capturing end of the imaging system to a work site in the patient. The delivery of the working and image capturing ends of the instruments and imaging system ("medical devices") uses one or more guide tubes and structures that hold and manipulate the guide tube(s). In addition, master manipulators are used as input devices to track the motion of their operator's hands and to provide appropriate haptic feedback to the operator indicative of the state of their associated slave manipulators. Depending on their respective function, the slave and master manipulators ("robotic manipulators") may be designed with different workspaces and dexterities.

In general, the reachable workspace of a medical device that is being manipulated by a slave manipulator is the set of points and orientations in space that its distal tip (e.g., working or image capturing end) can reach. On the other hand, the dexterous workspace of the medical device's distal tip generally identifies the set of points in space that can be reached by primarily changing its orientation (e.g., changing the position of a wrist joint that orients the distal tip). As explanation, dexterity is a measure of the capability of a robotic manipulator to control the position (in a limited manner) and orientation of the working end of its associated medical device. Further, it relates the joint degrees of freedom (i.e. the number of independently actuated joints in a kinematic chain of the robotic manipulator/medical device) and the Cartesian/output degrees of freedom that describe the independent rigid body positions and orientations of the distal tip. While the number of output (slave manipulator) degrees of freedom (DOF) is often at most six, the number of input (master manipulator) joint DOFs varies greatly depending on the master manipulator design As may be readily appreciated, the dexterous workspace is generally a subset of the reachable workspace. To enable the surgeon to finely control working ends of the instruments, instrument slave manipulators are generally designed to optimize their dexterity, even at the expense of sacrificing their overall reachable workspace. To compensate for such limitation, a base manipulator (such as a patient side cart) with a large reachable workspace may be used to deliver the instrument and imaging system slave manipulators near the entry apertures (e.g., minimally invasive incisions or natural orifices) in the patient body. Further, when the instruments and imaging system are disposed within a common guide tube, the guide tube serves as a secondary base since movement of the guide tube in this case effectively moves all of the instruments and the imaging system disposed therein. The instrument and imaging system slave manipulators may then finally deliver the working and image capturing ends of their respective medical devices to the work site (e.g., target anatomy) in the patient.

The overall capability of a medical robotic system is achieved by a balance between the workspace and dexterity of all the robotic manipulators that constitute it. However, the differences in the individual capabilities of each manipulator have to be clear and well understood by the user in order to effectively utilize the system. It is in general difficult for the user to select which manipulator to control from the console and how to move it in order to achieve a desired "working configuration" of their respective medical devices inside the patient, with the instruments' working ends having the best possible dexterity and reach, while the capturing end of the imaging system is positioned in such a way to provide good visualization of the medical procedure being performed at the work site without interfering with the instruments' movements. Hence, it is desirable to provide the system with the capability of performing secondary or coupled control movements, e.g., for the camera manipulator and the base manipulator (guide tube manipulator and/or manipulator for moving the setup arms and or support for the patient side support system), so as not to distract the user from performing the medical procedure at the time using the surgical instruments.

The number of degrees of freedom (DOFs) is the number of independent variables that uniquely identify the pose/configuration of a system. Since robotic manipulators are kinematic chains that map the (input) joint space into the (output) Cartesian space, the notion of DOF can be expressed in any of these two spaces. In particular, the set of joint DOFs is the set of joint variables for all the independently controlled joints. Without loss of generality, joints are mechanisms that provide a single translational (prismatic joints) or rotational (revolute joints) DOF. Any mechanism that provides more than one DOF motion is considered, from a kinematic modeling perspective, as two or more separate joints. The set of Cartesian DOFs is usually represented by the three translational (position) variables (e.g., surge, heave, sway) and by the three rotational (orientation) variables (e.g. Euler angles or roll/pitch/yaw angles) that describe the position and orientation of an end effector (or tip) frame with respect to a given reference Cartesian frame.

For example, a planar mechanism with an end effector mounted on two independent and perpendicular rails has the capability of controlling the x/y position within the area spanned by the two rails (prismatic DOFs). If the end effector can be rotated around an axis perpendicular to the plane of the rails, then there are then three input DOFs (the two rail positions and the yaw angle) that correspond to three output DOFs (the x/y position and the orientation angle of the end effector).

Although the number of Cartesian DOFs is at most six, a condition in which all the translational and orientational variables are independently controlled, the number of joint DOFs is generally the result of design choices that involve considerations of the complexity of the mechanism and the task specifications. Accordingly, the number of joint DOFs can be more than, equal to, or less than six. For non-redundant kinematic chains, the number of independently controlled joints is equal to the degree of mobility for the end effector frame. For a certain number of prismatic and revolute joint DOFs, the end effector frame will have an equal number of DOFs (except when in singular configurations) in Cartesian space that will correspond to a combination of translational (x/y/z position) and rotational (roll/pitch/yaw orientation angle) motions.

The distinction between the input and the output DOFs is extremely important in situations with redundant or "defective" kinematic chains (e.g., mechanical manipulators). In particular, "defective" manipulators have fewer than six independently controlled joints and therefore do not have the capability of fully controlling end effector position and orientation. Instead, defective manipulators are limited to controlling only a subset of the position and orientation variables. On the other hand, redundant manipulators have more than six joint DOFs. Thus, a redundant manipulator can use more than one joint configuration to establish a desired 6-DOF end effector pose. In other words, additional degrees of freedom can be used to control not just the end effector position and orientation but also the "shape" of the manipulator itself. In addition to the kinematic degrees of freedom, mechanisms may have other DOFs, such as the pivoting lever movement of gripping jaws or scissors blades.

It is also important to consider reference frames for the space in which DOFs are specified. For example, a single DOF change in joint space (e.g., the joint between two links rotates) may result in a motion that combines changes in the Cartesian translational and orientational variables of the frame attached to the distal tip of one of the links (the frame at the distal tip both rotates and translates through space).

Kinematics describes the process of converting from one measurement space to another. For example, using joint space measurements to determine the Cartesian space position and orientation of a reference frame at the tip of a kinematic chain is "forward" kinematics. Using Cartesian space position and orientation for the reference frame at the tip of a kinematic chain to determine the required joint positions is "inverse" kinematics. If there are any revolute joints, kinematics involves non-linear (trigonometric) functions.

SUMMARY

An object of aspects of the invention is to provide coupled control modes in which one or more devices may be directly controlled to achieve a primary objective and one or more other devices may be indirectly controlled to achieve secondary objectives.

These and additional objects are accomplished by the various aspects of the present invention, wherein briefly stated, one aspect is a robotic system comprising: a master input device; first and second slave manipulators; and means for commanding the second slave manipulator to move in response at least in part to commanded movement of the first slave manipulator when the first slave manipulator moves in response to movement of the master input device and commanding the first slave manipulator to move in response at least in part to commanded movement of the second slave manipulator when the second slave manipulator moves in response to movement of the master input device.

Another aspect is a robotic system comprising: a first instrument; a base that the first instrument is coupled to so that the first instrument moves when the base moves; a base controller means for causing the base to be moved so as to optimize a workspace of the first instrument as the first instrument moves; and a first instrument controller for moving the first instrument according to commanded movement while compensating for movement of the base.

Another aspect is a method for controlling movement of one or more instruments coupled to a base so that the instruments move as the base moves, the method comprising: commanding manipulation of the base so as to optimize an operable workspace of a first instrument; and commanding manipulation of the first instrument according to commanded movement while compensating for movement of the base.

Another aspect is a robotic system comprising: a plurality of devices each manipulated by a corresponding one of a plurality of slave manipulators; a master input device; and means for commanding the plurality of slave manipulators to move their respective devices in a common degree-of-freedom direction in response to movement of the master input device.

Another aspect is a method for retracting a plurality of devices back into a guide tube, the method comprising: receiving a retraction command from an input device; retracting a plurality of devices extending beyond a distal end of a guide tube back together towards the guide tube in response to the retraction command; and driving the plurality of devices to retraction configurations so that each of the plurality of devices may freely enter the guide tube.

Still another aspect is a robotic system comprising: a plurality of instruments each manipulated by a corresponding one of a plurality of slave manipulators; an imaging system manipulated by an imaging system manipulator; a master input device; and means for commanding the plurality of slave manipulators to move the plurality of instruments in response to movement of the imaging system when the imaging system manipulator moves in response to movement of the master input device.

Yet another aspect is a method for coupling control of an imaging system with other devices in a robotic system, the method comprising: causing a plurality of instruments to move so as to follow an image capturing end of an imaging system as the imaging system moves in response to movement of a master input device.

BRIEF DESCRIPTION OF THE DRAWINGS

FIG. 14 is a diagrammatic view of transmission mechanisms associated with flexible coaxial guide tubes and instruments.

FIG. 15 is a diagrammatic view of multi-port surgery.

FIG. 16 is another diagrammatic view of multi-port surgery.

FIGS. 24-25 are block diagrams of a direct "tool following" mode architecture implemented in the manipulator controllers in the telesurgical system.

FIGS. 28-29 are block diagrams of a direct "guide tube" mode architecture implemented in the manipulator controllers in the telesurgical system.

DETAILED DESCRIPTION

Figure 1:
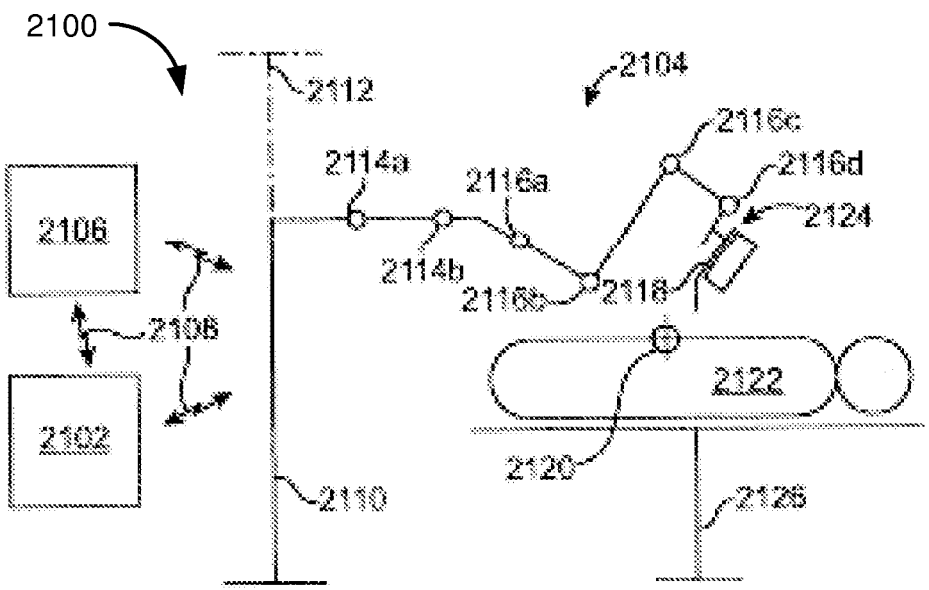
FIG. 1 is a schematic view of a robot-assisted minimally invasive telesurgical system.

This description and the accompanying drawings that illustrate aspects and embodiments of the present invention should not be taken as limiting—the claims define the protected invention. Various mechanical, compositional, structural, electrical, and operational changes may be made without departing from the spirit and scope of this description and the claims. In some instances, well-known circuits, structures, and techniques have not been shown in detail in order not to obscure the invention. Like numbers in two or more figures represent the same or similar elements.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations), and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Telemanipulation and like terms generally refer to an operator manipulating a master device (e.g., an input kinematic chain) in a relatively natural way (e.g., a natural hand or finger movement), whereupon the master device movements are made into commands that are processed and transmitted in real time to a slave device (e.g., an output kinematic chain) that reacts nearly instantaneously to the commands and to environmental forces. Telemanipulation is disclosed in U.S. Pat. No. 6,574,355 (Green), which is incorporated by reference.

To avoid repetition in the figures and the descriptions below of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description.

Accordingly, several general aspects apply to various descriptions below. For example, at least one surgical end effector is shown or described in various figures. An end effector is the part of the minimally invasive surgical instrument or assembly that performs a specific surgical function (e.g., forceps/graspers, needle drivers, scissors, electrocautery hooks, staplers, clip appliers/removers, etc.). Many end effectors have a single DOF (e.g., graspers that open and close). The end effector may be coupled to the surgical instrument body with a mechanism that provides one or more additional DOFs, such as "wrist" type mechanisms. Examples of such mechanisms are shown in U.S. Pat. No. 6,371,952 (Madhani et al.) and in U.S. Pat. No. 6,817,974 (Cooper et al.), both of which are incorporated by reference, and may be known as various Intuitive Surgical, Inc. Endowrist® mechanisms as used on both 8 mm and 5 mm instruments for the da Vinci® Surgical System. Although the surgical instruments described herein generally include end effectors, it should be understood that in some aspects an end effector may be omitted. For example, the distal tip of an instrument body shaft may be used to retract tissue. As another example, suction or irrigation openings may exist at the distal tip of a body shaft or the wrist mechanism. In these aspects, it should be understood that descriptions of positioning and orienting an end effector include positioning and orienting the tip of a surgical instrument that does not have an end effector. For example, a description that addresses the reference frame for a tip of an end effector should also be read to include the reference frame of the tip of a surgical instrument that does not have an end effector.

Throughout this description, it should be understood that a mono-or stereoscopic imaging system/image capture component/camera device may be placed at the distal end of an instrument wherever an end effector is shown or described (the device may be considered a "camera instrument"), or it may be placed near or at the distal end of any guide tube or other instrument assembly element. Accordingly, the terms "imaging system" and the like as used herein should be broadly construed to include both image capture components and combinations of image capture components with associated circuitry and hardware, within the context of the aspects and embodiments being described. Such endoscopic imaging systems (e.g., optical, infrared, ultrasound, etc.) include systems with distally positioned image sensing chips and associated circuits that relay captured image data via a wired or wireless connection to outside the body. Such endoscopic imaging systems also include systems that relay images for capture outside the body (e.g., by using rod lenses or fiber optics). In some instruments or instrument assemblies a direct view optical system (the endoscopic image is viewed directly at an eyepiece) may be used. An example of a distally positioned semiconductor stereoscopic imaging system is described in U.S. patent application Ser. No. 11/614,661

"Stereoscopic Endoscope" (Shafer et al.), which is incorporated by reference. Well-known endoscopic imaging system components, such as electrical and fiber optic illumination connections, are omitted or symbolically represented for clarity. Illumination for endoscopic imaging is typically represented in the drawings by a single illumination port. It should be understood that these depictions are exemplary. The sizes, positions, and numbers of illumination ports may vary. Illumination ports are typically arranged on multiple sides of the imaging apertures, or completely surrounding the imaging apertures, to minimize deep shadows.

In this description, cannulas are typically used to prevent a surgical instrument or guide tube from rubbing on patient tissue. Cannulas may be used for both incisions and natural orifices. For situations in which an instrument or guide tube does not frequently translate or rotate relative to its insertion (longitudinal) axis, a cannula may not be used. For situations that require insufflation, the cannula may include a seal to prevent excess insufflation gas leakage past the instrument or guide tube. For example, for thoracic surgery that does not require insufflation, the cannula seal may be omitted, and if instruments or guide tube insertion axis movement is minimal, then the cannula itself may be omitted. A rigid guide tube may function as a cannula in some configurations for instruments that are inserted relative to the guide tube. Cannulas and guide tubes may be, e.g., steel or extruded plastic. Plastic, which is less expensive than steel, may be suitable for one-time use.

Various instances and assemblies of flexible surgical instruments and guide tubes are contemplated as applicable with the present invention. Such flexibility, in this description, is achieved in various ways. For example, a segment or an instrument or guide tube may be a continuously curving flexible structure, such as one based on a helical wound coil or on tubes with various segments removed (e.g., kerf-type cuts). Or, the flexible part may be made of a series of short, pivotally connected segments ("vertebrae") that provide a snake-like approximation of a continuously curving structure. Instrument and guide tube structures may include those in U.S. Patent Application Pub. No. US 2004/0138700 (Cooper et al.), which is incorporated by reference. For clarity, the figures and associated descriptions generally show only two segments of instruments and guide tubes, termed proximal (closer to the transmission mechanism; farther from the surgical site) and distal (farther from the transmission mechanism; closer to the surgical site). It should be understood that the instruments and guide tubes may be divided into three or more segments, each segment being rigid, passively flexible, or actively flexible. Flexing and bending as described for a distal segment, a proximal segment, or an entire mechanism also apply to intermediate segments that have been omitted for clarity. For instance, an intermediate segment between proximal and distal segments may bend in a simple or compound curve. Flexible segments may be various lengths. Segments with a smaller outside diameter may have a smaller minimum radius of curvature while bending than segments with a larger outside diameter. For cable-controlled systems, unacceptably high cable friction or binding limits minimum radius of curvature and the total bend angle while bending. The guide tube's (or any joint's) minimum bend radius is such that it does not kink or otherwise inhibit the smooth motion of the inner surgical instrument's mechanism. Flexible components may be, for example, up to approximately four feet in length and approximately 0.6 inches in diameter. Other lengths and diameters (e.g., shorter, smaller) and the degree of flexibility for a specific mechanism may be determined by the target anatomy for which the mechanism has been designed.

In some instances only a distal segment of an instrument or guide tube is flexible, and the proximal segment is rigid. In other instances, the entire segment of the instrument or guide tube that is inside the patient is flexible. In still other instances, an extreme distal segment may be rigid, and one or more other proximal segments are flexible. The flexible segments may be passive or they may be actively controllable ("steerable"). Such active control may be done using, for example, sets of opposing cables (e.g., one set controlling "pitch" and an orthogonal set controlling "yaw"; three cables can be used to perform similar action). Other control elements such as small electric or magnetic actuators, shape memory alloys, electroactive polymers ("artificial muscle"), pneumatic or hydraulic bellows or pistons, and the like may be used. In instances in which a segment of an instrument or guide tube is fully or partially inside another guide tube, various combinations of passive and active flexibility may exist. For instance, an actively flexible instrument inside a passively flexible guide tube may exert sufficient lateral force to flex the surrounding guide tube. Similarly, an actively flexible guide tube may flex a passively flexible instrument inside it. Actively flexible segments of guide tubes and instruments may work in concert. For both flexible and rigid instruments and guide tubes, control cables placed farther from the center longitudinal axis may provide a mechanical advantage over cables placed nearer to the center longitudinal axis, depending on compliance considerations in the various designs.

The flexible segment's compliance (stiffness) may vary from being almost completely flaccid (small internal frictions exist) to being substantially rigid. In some aspects, the compliance is controllable. For example, a segment or all of a flexible segment of an instrument or guide tube can be made substantially (i.e., effectively but not infinitely) rigid (the segment is "rigidizable" or "lockable"). The lockable segment may be locked in a straight, simple curve or in a compound curve shape. Locking may be accomplished by applying tension to one or more cables that run longitudinally along the instrument or guide tube that is sufficient to cause friction to prevent adjacent vertebrae from moving. The cable or cables may run through a large, central hole in each vertebra or may run through smaller holes near the vertebra's outer circumference. Alternatively, the drive element of one or more motors that move one or more control cables may be soft-locked in position (e.g., by servocontrol) to hold the cables in position and thereby prevent instrument or guide tube movement, thus locking the vertebrae in place. Keeping a motor drive element in place may be done to effectively keep other movable instrument and guide tube components in place as well. It should be understood that the stiffness under servocontrol, although effective, is generally less than the stiffness that may be obtained with braking placed directly on joints, such as the braking used to keep passive setup joints in place. Cable stiffness generally dominates because it is generally less than servosystem or braked joint stiffness.

In some situations, the compliance of the flexible segment may be continuously varied between flaccid and rigid states. For example, locking cable tension can be increased to increase stiffness but without locking the flexible segment in a rigid state. Such intermediate compliance may allow for telesurgical operation while reducing tissue trauma that may occur due to movements caused by reactive forces from the surgical site. Suitable bend sensors incorporated into the flexible segment allow the telesurgical system to determine instrument and/or guide tube position as it bends. U.S. patent application Pub. No. US 2006/0013523 (Childers et al.), which is incorporated by reference, discloses a fiber optic position shape sensing device and method. U.S. patent application Ser. No. 11/491,384 (Larkin et al.), which is incorporated by reference, discloses fiber optic bend sensors (e.g., fiber Bragg gratings) used in the control of such segments and flexible devices.

A surgeon's inputs to control aspects of the minimally invasive surgical instrument assemblies, instruments, and end effectors as described herein are generally done using an intuitive, camera referenced control interface. For example, the da Vinci® Surgical System includes a Surgeon's console with such a control interface, which may be modified to control aspects described herein. The surgeon manipulates one or more master manual input mechanisms having, e.g., 6 DOFs to control the slave instrument assembly and instrument. The input mechanisms include a finger-operated grasper to control one or more end effector DOFs (e.g., closing grasping jaws). Intuitive control is provided by orienting the relative positions of the end effectors and the endoscopic imaging system with the positions of the surgeon's input mechanisms and image output display. This orientation allows the surgeon to manipulate the input mechanisms and end effector controls as if viewing the surgical work site in substantially true presence. This teleoperation true presence means that the surgeon views an image from a perspective that appears to be that of an operator directly viewing and working at the surgical site. U.S. Pat. No. 6,671,581 (Niemeyer et al.), which is incorporated by reference, contains further information on camera referenced control in a minimally invasive surgical apparatus.

FIG. 1 is a schematic view that illustrates aspects of a robot-assisted (telemanipulative) minimally invasive surgical system 2100 in which instruments are inserted in a patient through a single entry aperture through a guide tube. This system's general architecture is similar to the architecture of other such systems such as Intuitive Surgical, Inc.'s da Vinci® Surgical System and the Zeus® Surgical System. The three main components are a surgeon's console 2102, a patient side support system 2104, and a video system 2106, all interconnected 2108 by wired or wireless connections as shown.

Figure 4:
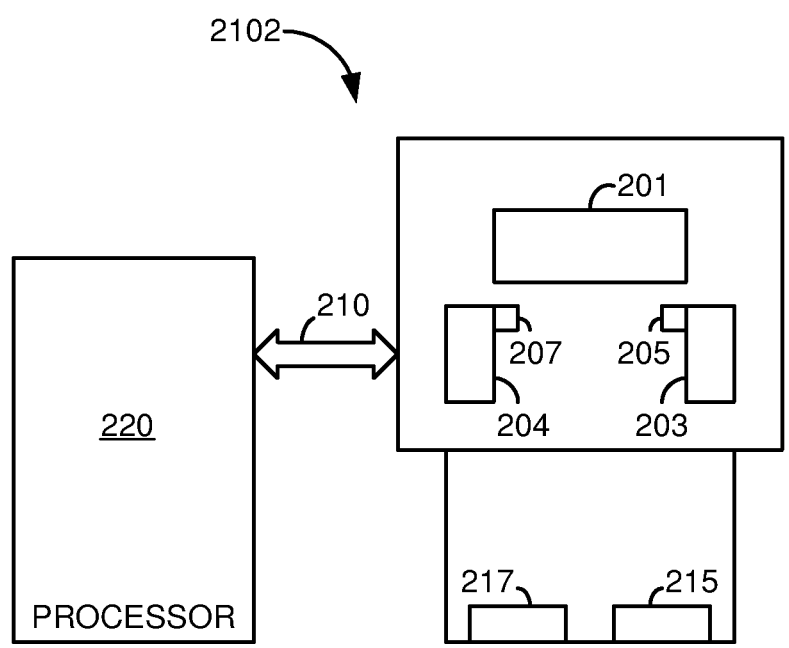
FIG. 4 is a simplified front view of a surgeon's console in a telesurgical system.

As shown in FIG. 4, the surgeon's console 2102 includes, e.g., hand-operable, multiple DOF mechanical input ("master") devices 203, 204 and foot pedals 215, 217 that allow the surgeon to manipulate the surgical instruments, guide tubes, and imaging system ("slave") devices as described herein. These input devices may in some aspects provide haptic feedback from the instruments and instrument assembly components to the surgeon. Buttons 205, 207 are provided on the hand-operable input devices 203, 204 for switching functions as described herein or for other operational purposes. Console 2102 also includes a stereoscopic video output display 201 positioned such that images on the display are generally focused at a distance that corresponds to the surgeon's hands working behind/below the display screen. A processor 220 in communication with other components of the console via bus 210 performs various functions in the system 2100. One important function that it performs is to implement the various controllers described herein to translate and transfer the mechanical motion of input devices through control signals so that the Surgeon can effectively manipulate and otherwise move devices, such as the surgical instruments, an imaging system, and one or more guide tubes, that are selectively associated with the input devices at the time. Although described as a processor, it is to be appreciated that the processor 220 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 2102, the processor 220 may also comprise a number of subunits distributed throughout the system. These aspects are discussed more fully in U.S. Pat. No. 6,671,581, which is incorporated by reference above.

Referring back to FIG. 1, the patient side support system 2104 includes a floor-mounted structure 2110, or alternately a ceiling mounted structure 2112 as shown by the alternate lines. The structure 2110 may be movable or fixed (e.g., to the floor, ceiling, or other equipment such as an operating table). In one embodiment a set-up arm assembly 2114 is a modified da Vinci® Surgical System arm assembly. The arm assembly 2114 includes two illustrative passive rotational setup joints 2114a, 2114b, which allow manual positioning of the coupled links when their brakes are released. A passive prismatic setup joint (not shown) between the arm assembly and the structure 2110 may be used to allow for large vertical adjustments. In addition, a guide tube manipulator 2116 includes illustrative active roll joint 2116a and active yaw joint 2116b. Joints 2116c and 2116d act as a parallel mechanism so that a guide tube (of a surgical instrument assembly) held by a platform 2118 moves around remote center 2120 at an entry port, such as patient 1222's umbilicus. In one embodiment, an active prismatic joint 2124 is used to insert and withdraw the guide tube. One or more surgical instruments and an endoscopic imaging system are independently mounted to platform 2118. The various setup and active joints allow the manipulators to move the guide tube, instruments, and imaging system when patient 2122 is placed in various positions on movable table 2126.

Figure 2:
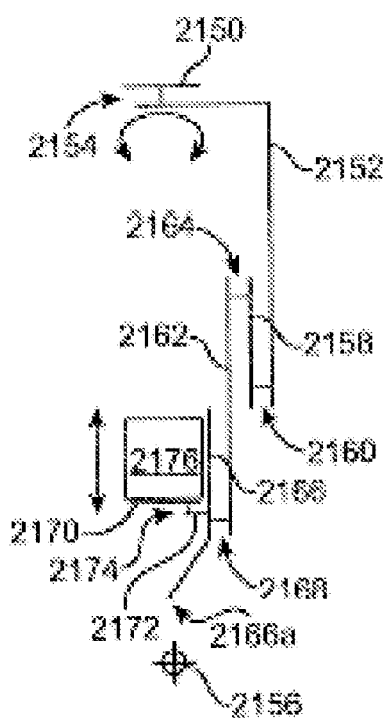
FIGS. 2 and 3 are schematic views of a patient side support system in a telesurgical system.
Figure 3:
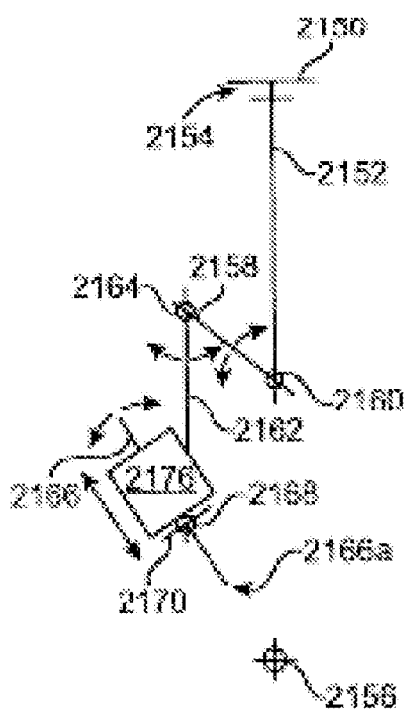

FIGS. 2 and 3 are schematic side and front elevation views of another illustrative embodiment of a patient side support system. Support 2150 is fixed (e.g., floor or ceiling mounted). Link 2152 is coupled to support 2150 at passive rotational setup joint 2154. As shown, joint 2154's rotational axis is aligned with remote center point 2156, which is generally the position at which a guide tube (of a surgical instrument assembly; not shown) enters the patient (e.g., at the umbilicus for abdominal surgery). Link 2158 is coupled to link 2152 at rotational joint 2160. Link 2162 is coupled to link 2158 at rotational joint 2164. Link 2166 is coupled to link 2162 at rotational joint 2168. The guide tube is mounted to slide through the end 2166a of link 2166. Platform 2170 is supported and coupled to link 2166 by a prismatic joint 2172 and a rotational joint 2174. Prismatic joint 2172 inserts and withdraws the guide tube as it slides along link 2166. Joint 2174 includes a bearing assembly that holds a "C" shaped ring cantilever. As the "C" ring slides through the bearing it rotates around a center point inside the "C", thereby rolling the guide tube. The opening in the "C" allows guide tubes to be mounted or exchanged without moving overlying manipulators. Platform 2170 supports multiple manipulators 2176 for surgical instruments and an imaging system, as described below.

These illustrative robotic arm assemblies are used, for example, for instrument assemblies that include a rigid guide tube and are operated to move with reference to a remote center. Certain setup and active joints in the manipulator arm may be omitted if motion around a remote center is not required. It should be understood that manipulator arms may include various combinations of links, passive, and active joints (redundant DOFs may be provided) to achieve a necessary range of poses for surgery.

Referring again to FIG. 1, video system 2106 performs image processing functions for, e.g., captured endoscopic imaging data of the surgical site and/or preoperative or real time image data from other imaging systems external to the patient. Video system 2106 outputs processed image data (e.g., images of the surgical site, as well as relevant control and patient information) to the surgeon at the surgeon's console 2102. In some aspects the processed image data is output to an optional external monitor visible to other operating room personnel or to one or more locations remote from the operating room (e.g., a surgeon at another location may monitor the video; live feed video may be used for training; etc.).

Figure 5:
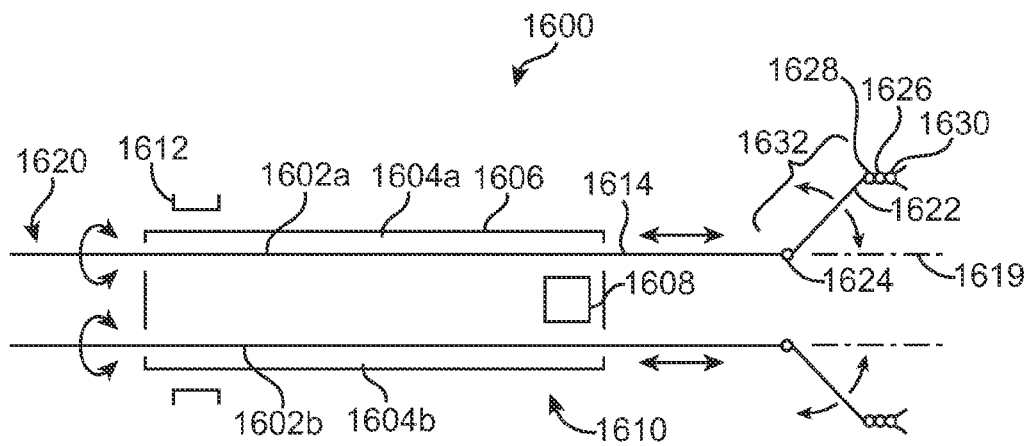
FIG. 5 is a schematic view that illustrates aspects of a minimally invasive surgical instrument assembly.

As an example of an instrument assembly, FIG. 5 is a schematic view that illustrates aspects of a minimally invasive surgical instrument assembly 1600. Two surgical instruments 1602a,1602b extend through channels 1604a,1604b that extend longitudinally through rigid guide tube 1606. In some aspects guide tube 1606 is straight and in others it is curved to accommodate a particular insertion port (the instruments are similarly curved to facilitate insertion). Guide tube 1606 may have various cross-sectional shapes (e.g., circular, oval, rounded polygon), and various numbers of surgical instruments and channels may be used. Some optional working channels may be used to provide supporting surgical functions such as irrigation and suction. In some aspects an endoscopic imaging system (e.g., mono-or stereoscopic image capture or direct view) is at guide tube 1606's distal end 1610. In one aspect guide tube 1606 is inserted into a patient via an incision (e.g., approximately 2.0 cm at the umbilicus) or natural orifice, either with or without the use of a cannula 1612 or similar guiding structure. In some aspects guide tube 1606 may rotate within cannula 1612.

Surgical instruments 1602a and 1602b function in a like manner, and many instrument functions (body roll, wrist operation, end effector operation, etc.) are similar to the surgical instruments used in the da Vinci® Surgical System (both 8 mm and 5 mm instrument body diameters). In other aspects the instruments may function differently and/or have capabilities not embodied in da Vinci® Surgical System instruments (e.g., one instrument may be straight, one instrument may be jointed, one instrument may be flexible, etc.). In the present example, instrument 1602a includes a transmission portion (not shown) at its proximal end, an elongated instrument body 1614, one of various surgical end effectors 1616, and a snake-like, two degree of freedom wrist mechanism 1618 that couples end effector 1616 to instrument body 1614. As in the da Vinci® Surgical Systems, in some aspects the transmission portion includes disks that interface with electrical actuators (e.g., servomotors) permanently mounted on a support arm so that instruments may easily be changed. Other linkages such as matching gimbal plates and levers may be used to transfer actuating forces at the mechanical interface. Mechanical mechanisms (e.g., gears, levers, gimbals) in the transmission portion transfer the actuating forces from the disks to cables, wires, and/or cable, wire, and hypotube combinations that run through one or more channels in instrument body 1614 (which may include one or more articulated segments) to control wrist 1618 and end effector 1616 movement. In some aspects, one or more disks and associated mechanisms transfer actuating forces that roll instrument body 1614 around its longitudinal axis 1619 as shown. In some aspects the actuators for a particular instrument are themselves mounted on a single linear actuator that moves instrument body 1614 longitudinally as shown within channel 1604a. The main segment of instrument body 1614 is a substantially rigid single tube, although in some aspects it may be slightly resiliently flexible. This small flexibility allows a proximal body segment 1620 proximal of guide tube 1606 (i.e., outside the patient) be slightly flexed so that several instrument bodies can be spaced more closely within guide tube 1606 than their individual transmission segment housings would otherwise allow, like several cut flowers of equal length being placed in a small-necked vase. This flexing is minimal (e.g., less than or equal to about a 5-degree bend angle in one embodiment) and does not induce significant friction because the bend angle for the control cables and hypotubes inside the instrument body is small.

Instruments 1602a and 1602b each include a proximal body segment that extends through the guide tube and at least one distal body segment that is positioned beyond the guide tube's distal end. For example, instrument 1602a includes proximal body segment 1620 that extends through guide tube 1606, a distal body segment 1622 that is coupled to proximal body segment 1620 at a joint 1624, a wrist mechanism 1626 that is coupled to distal body segment 1622 at another joint 1628 (the coupling may include another, short distal body segment), and an end effector 1630. In some aspects the distal body segment 1622 and joints 1624 and 1628 function as a parallel motion mechanism 1632 in which the position of a reference frame at the distal end of the mechanism may be changed with respect to a reference frame at the proximal end of the mechanism without changing the orientation of the distal reference frame.

Figure 6:
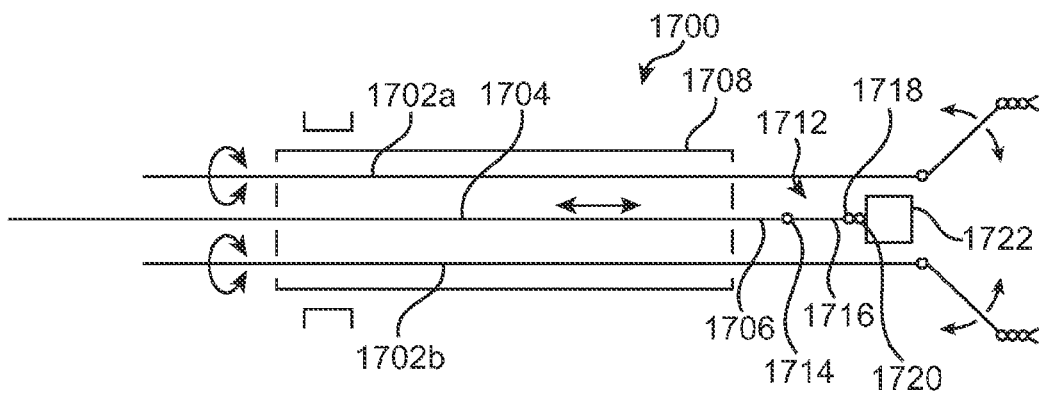
FIG. 6 is a schematic view that illustrates aspects of a minimally invasive surgical instrument assembly.

FIG. 6 is a schematic view that illustrates aspects of another minimally invasive surgical instrument assembly 1700. Surgical instrument assembly 1700 is similar to instrument assembly 1600 in that surgical instruments 1702a,1702b function similarly to instruments 1602a,1602b as described above, but instead of a fixed endoscopic imaging system at the end of the guide tube, assembly 1700 has an independently operating endoscopic imaging system 1704.

In one aspect, imaging system 1704 is mechanically similar to surgical instruments 1602 as described above. Summarizing these aspects as shown in FIG. 6, optical system 1704 includes a substantially rigid elongate tubular proximal body segment 1706 that extends through guide tube 1708, and at proximal body segment 1706's distal end there is coupled a 1 or 2 DOF parallel motion mechanism 1712 that is similar to parallel motion mechanism 1622. Parallel motion mechanism 1712 includes a first joint 1714, an intermediate distal body segment 1716, and a second joint 1718. A wrist mechanism or other active joint (e.g., one DOF to allow changing pitch angle; two DOFs to allow changing pitch and yaw angles) 1720 couples an image capture component 1722 to second joint 1718. Alternatively, joint 1714 is an independently controllable one or two DOF joint (pitch/yaw), joint 1718 is another independently controllable one or two DOF joint (e.g., pitch/yaw), and image capture component 1722 is coupled directly at the distal end of the joint 1718 mechanism. An example of a suitable stereoscopic image capture component is shown in U.S. patent application Ser. No. 11/614,661, incorporated by reference above. In some aspects imaging system 1704 moves longitudinally (surges) inside guide tube 1708. Control of imaging system 1704 is further described in concurrently filed U.S. patent application Ser. No. 11/762, 236, incorporated by reference above. In some aspects, roll may be undesirable because of a need to preserve a particular field of view orientation. Having heave (up/down), sway (side-to-side), surge (retraction/insertion), yaw, and pitch DOFs allows the image capture component to be moved to various positions while preserving a particular camera reference for assembly 1700 and viewing alignment for the surgeon.

Figure 7:
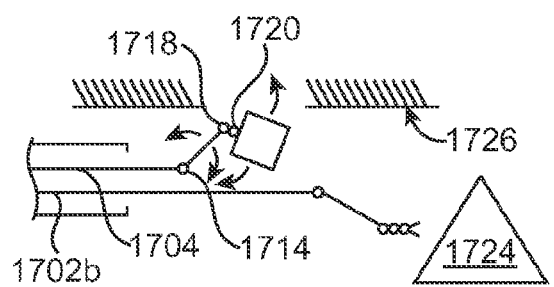
FIG. 7 is a schematic side view of a detail of FIG. 6.

FIG. 7 is, for illustrative purposes only, a side view schematic to FIG. 6's plan view schematic. FIG. 7 shows that parallel motion mechanism 1712 moves image capture component 1722 away from surgical instrument assembly 1700's longitudinal centerline. This displacement provides an improved view of surgical site 1724 because some or all of the instrument body distal segment ends are not present in the image output to the surgeon as would occur in, e.g., instrument assembly 1600 (FIG. 5). The pitch of parallel motion mechanism 1712 and of image capture component 1722 is controllable, as illustrated by the arrows.

Figure 8:
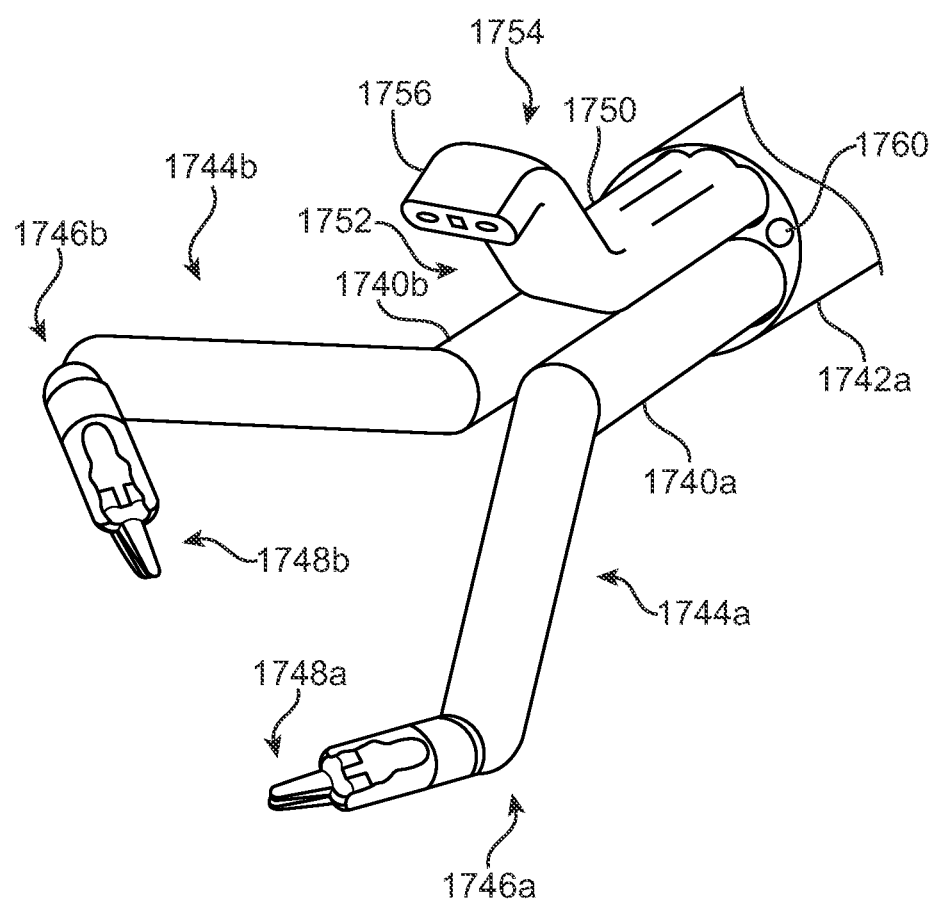
FIG. 8 is a diagrammatic perspective view of a surgical instrument assembly.

FIG. 8 is a diagrammatic perspective view that illustrates an embodiment of surgical instrument assembly 1700. As shown, two independently teleoperated surgical instruments 1740a,1740b (each instrument is associated with a separate master—e.g. one left hand master for the left instrument and one right hand master for the right instrument) run through and emerge at the distal end of a rigid guide tube 1742. Each instrument 1740a,1740b is a 6 DOF instrument, as described above, and includes a parallel motion mechanism 1744a, 1744b, as described above, with wrists 1746a,1746b and end effectors 1748a,1748b attached. In addition, an independently teleoperated endoscopic imaging system 1750 runs through and emerges at the distal end of guide tube 1742. In some aspects imaging system 1750 also includes a parallel motion mechanism 1752, a pitch-only wrist mechanism 1754 at the distal end of the parallel motion mechanism 1752 (the mechanism may have either one or two DOFs in joint space), and a stereoscopic endoscopic image capture component 1756 coupled to wrist mechanism 1754. In other aspects, wrist mechanism 1754 may include a yaw DOF. In yet another aspect, the proximal and distal joints in imaging system 1750 are independently controlled. In an illustrative use, parallel motion mechanism 1752 heaves and sways image capture component 1756 up and to the side, and wrist mechanism 1754 orients image capture component 1756 to place the center of the field of view between the instrument tips if the instruments are working to the side of the guide tube's extended centerline. In another illustrative use, the distal body segment of imaging system is independently pitched up (in some aspects also independently yawed), and image capture component 1756 is independently pitched down (in some aspects also independently yawed). As discussed above and below, imaging system 1750 may be moved to various places to retract tissue.

Also shown is an auxiliary channel 1760, through which, e.g., irrigation, suction, or other surgical items may be introduced or withdrawn. In some aspects, one or more small, steerable devices may be inserted via auxiliary channel 1760 to spray a cleaning fluid (e.g., pressurized water, gas) and/or a drying agent (e.g., pressurized air or insufflation gas) on the imaging system's windows to clean them. In another aspect, such a cleaning wand may be a passive device that attaches to the camera before insertion. In yet another aspect, the end of the wand is automatically hooked to the image capture component as the image capture component emerges from the guide tube's distal end. A spring gently pulls on the cleaning wand so that it tends to retract into the guide tube as the imaging system is withdrawn from the guide tube.

FIG. 7 further illustrates that as image capture component 1722 is moved away from assembly 1700's centerline it may press against and move an overlying tissue structure surface 1726, thereby retracting the tissue structure from the surgical site as shown. The use of imaging system 1704 to retract tissue is illustrative of using other surgical instruments, or a device specifically designed for the task, to retract tissue. Such "tent-pole" type retraction may be performed by any of the various movable components described herein, such as the distal end exit or side exit flexible devices and the parallel motion mechanisms on the rigid body component devices, as well as other devices discussed below (e.g., with reference to FIG. 21).

Figure 9:
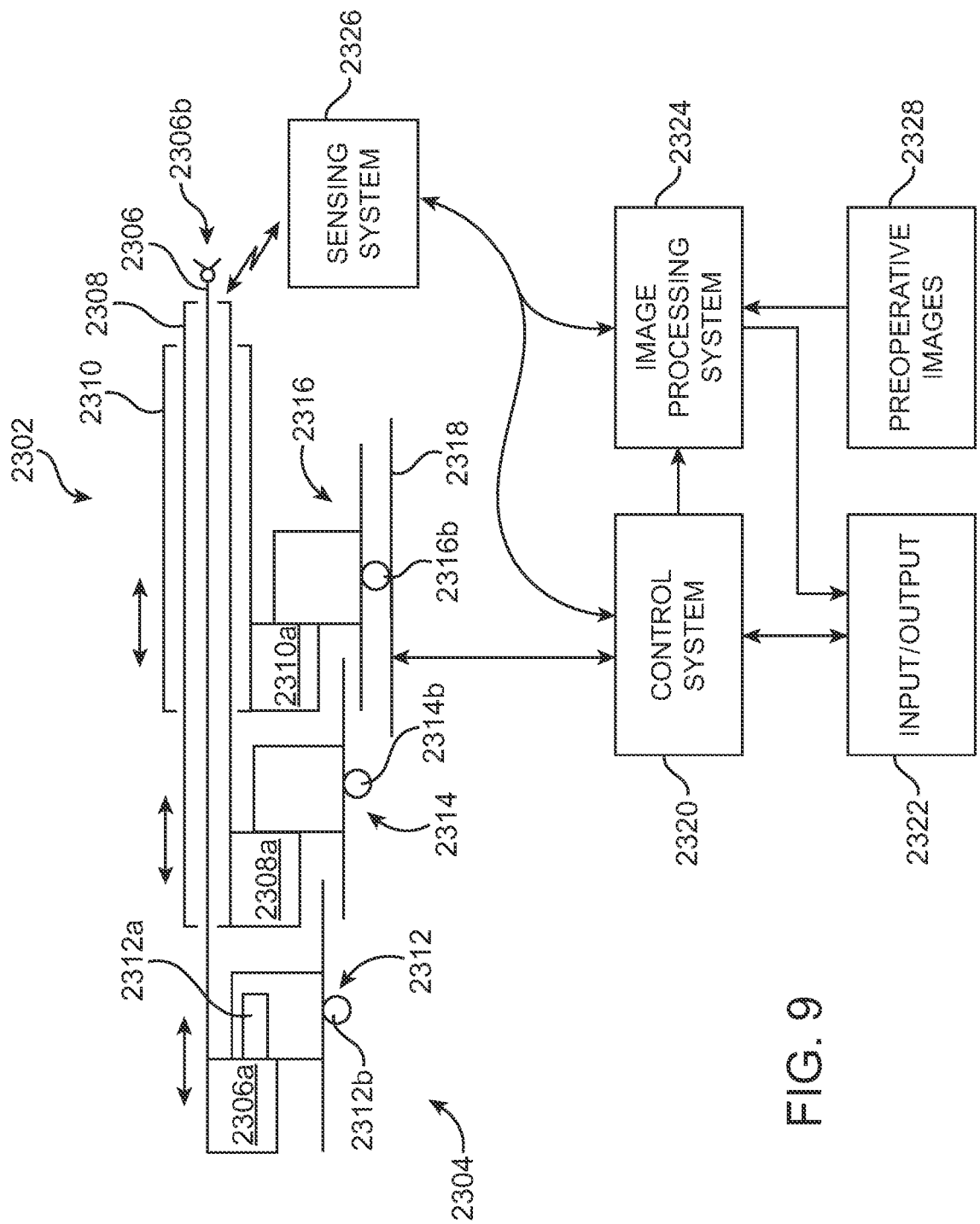
FIG. 9 is a schematic view of an interface between a surgical instrument assembly and an actuator assembly.

FIG. 9 is a schematic view that illustrates aspects of an interface between surgical instrument assembly 2302, which represents flexible and rigid mechanisms as variously described herein, and an illustrative actuator assembly 2304. For the purposes of this example, instrument assembly 2302 includes surgical instrument 2306, primary guide tube 2308 that surrounds instrument 2306, and secondary guide tube 2310 that surrounds primary guide tube 2308.

As shown in FIG. 9, a transmission mechanism is positioned at the proximal ends of each instrument or guide tube: transmission mechanism 2306a for instrument 2306, transmission mechanism 2308a for primary guide tube 2308, and transmission mechanism 2310a for secondary guide tube 2310. Each transmission mechanism is mechanically and removably coupled to an associated actuator mechanism: transmission mechanism 2306a to actuator mechanism 2312, transmission mechanism 2308a to actuator mechanism 2314, transmission mechanism 2310a to actuator mechanism 2316. In one aspect, mating disks are used as in the da Vinci® Surgical System instrument interface, as shown in more detail below. In another aspect, mating gimbal plates and levers are used. Various mechanical components (e.g., gears, levers, cables, pulleys, cable guides, gimbals, etc.) in the transmission mechanisms are used to transfer the mechanical force from the interface to the controlled element. Each actuator mechanism includes at least one actuator (e.g., servomotor (brushed or brushless)) that controls movement at the distal end of the associated instrument or guide tube. For example, actuator 2312a is an electric servomotor that controls surgical instrument 2306's end effector 2306b grip DOF. An instrument (including a guide probe as described herein) or guide tube (or, collectively, the instrument assembly) may be decoupled from the associated actuator mechanism(s) and slid out as shown. It may then be replaced by another instrument or guide tube. In addition to the mechanical interface there is an electronic interface between each transmission mechanism and actuator mechanism. This electronic interface allows data (e.g., instrument/guide tube type) to be transferred.

In some instances one or more DOFs may be manually actuated. For instance, surgical instrument 2306 may be a passively flexible laparoscopic instrument with a hand-actuated end effector grip DOF, and guide tube 2308 may be actively steerable to provide wrist motion as described above. In this example, the surgeon servocontrols the guide tube DOFs and an assistant hand controls the instrument grip DOF.

In addition to the actuators that control the instrument and/or guide tube elements, each actuator assembly may also include an actuator component (e.g., motor-driven cable, lead screw, pinion gear, etc.; linear motor; and the like) that provides motion along instrument assembly 2302's longitudinal axis (surge). As shown in the FIG. 9 example, actuator mechanism 2312 includes linear actuator 2312b, actuator mechanism 2314 includes linear actuator 2314b, and actuator mechanism 2316 includes linear actuator 2316b, so that instrument 2306, primary guide tube 2308, and secondary guide tube 2310 can each be independently coaxially moved. As further shown in FIG. 9, actuator assembly 2316 is mounted to setup arm 2318, either passively or actively as described above. In active mounting architectures, the active mounting may be used to control one or more component DOFs (e.g., insertion of a rigid guide tube).

Control signals from control system 2320 control the various servomotor actuators in actuator assembly 2304. The control signals are, e.g., associated with the surgeon's master inputs at input/output system 2322 to move instrument assembly 2302's mechanical slave components. In turn, various feedback signals from sensors in actuator assembly 2304, and/or instrument assembly 2302, and/or other components are passed to control system 2320. Such feedback signals may be pose information, as indicated by servomotor position or other position, orientation, and force information, such as may be obtained with the use of fiber Bragg grating-based sensors. Feedback signals may also include force sensing information, such as tissue reactive forces, to be, e.g., visually or haptically output to the surgeon at input/output system 2322.

Image data from an endoscopic imaging system associated with instrument assembly 2302 are passed to image processing system 2324. Such image data may include, e.g., stereoscopic image data to be processed and output to the surgeon via input/output system 2322 as shown. Image processing may also be used to determine instrument position, which is input to the control system as a form of distal position feedback sensor. In addition, an optional sensing system 2326 positioned outside and near the patient may sense position or other data associated with instrument assembly 2302. Sensing system 2326 may be static or may be controlled by control system 2320 (the actuators are not shown, and may be similar to those depicted or to known mechanical servo components), and it may include one or more actual sensors positioned near the patient. Position information (e.g., from one or more wireless transmitters, RFID chips, etc.) and other data from sensing system 2326 may be routed to control system 2320. If such position information or other data is to be visually output to the surgeon, control system 2320 passes it in either raw or processed form to image processing system 2324 for integration with the surgeon's output display at input/output system 2322. Further, any image data, such as fluoroscopic or other real-time imaging (ultrasound, X-ray, MRI, and the like), from sensing system 2326 are sent to image processing system 2324 for integration with the surgeon's display. And, real-time images from sensing system 2326 may be integrated with preoperative images accessed by image processing system 2324 for integration with the surgeon's display. In this way, for instance, preoperative images of certain tissue (e.g., brain tissue structures) are received from a data storage location 2328, may be enhanced for better visibility, the preoperative images are registered with other tissue landmarks in real time images, and the combined preoperative and real time images are used along with position information from instrument and actuator assemblies 2302,2304 and/or sensing system 2326 to present an output display that assists the surgeon to maneuver instrument assembly 2302 towards a surgical site without damaging intermediate tissue structures.

Figure 10:
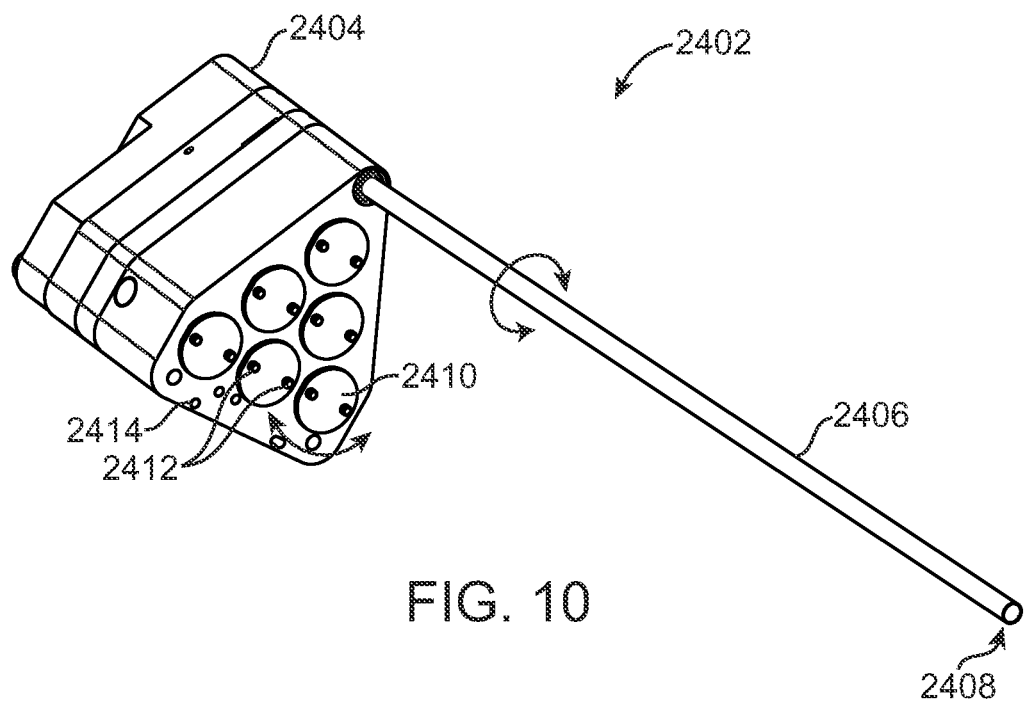
FIG. 10 is a perspective view of the proximal segment of a minimally invasive surgical instrument.

FIG. 10 is a perspective view of the proximal portion of a minimally invasive surgical instrument 2402. As shown in FIG. 10, instrument 2402 includes a transmission mechanism 2404 coupled to the proximal end of an instrument body tube 2406. Components at body tube 2406's distal end 2408 are omitted for clarity and may include, e.g., the 2 DOF parallel motion mechanism, wrist, and end effector combination as described above; joints and an endoscopic imaging system as described above; etc. In the illustrative embodiment shown, transmission mechanism 2404 includes six interface disks 2410. One or more disks 2410 are associated with a DOF for instrument 240. For instance, one disk may be associated with instrument body roll DOF, and a second disk may be associated with end effector grip DOF. As shown, in one instance the disks are arranged in a hexagonal lattice for compactness—in this case six disks in a triangular shape. Other lattice patterns or more arbitrary arrangements may be used. Mechanical components (e.g., gears, levers, gimbals, cables, etc.) inside transmission mechanism 2404 transmit roll torques on disks 2410 to e.g., body tube 2406 (for roll) and to components coupled to distal end mechanisms. Cables and/or cable and hypotube combinations that control distal end DOFs run through body tube 2406. In one instance the body tube is approximately 7 mm in diameter, and in another instance it is approximately 5 mm in diameter. Raised pins 2412, spaced eccentrically, provide proper disk 2410 orientation when mated with an associated actuator disk. One or more electronic interface connectors 2414 provide an electronic interface between instrument 2402 and its associated actuator mechanism. In some instances instrument 2402 may pass information stored in a semiconductor memory integrated circuit to the control system via its associated actuator mechanism. Such passed information may include instrument type identification, number of instrument uses, and the like. In some instances the control system may update the stored information (e.g., to record number of uses to determine routine maintenance scheduling or to prevent using an instrument after a prescribed number of times). U.S. Pat. No. 6,866,671 (Tierney et al.), which discusses storing information on instruments, is incorporated by reference. The electronic interface may also include power for, e.g., an electrocautery end effector. Alternately, such a power connection may be positioned elsewhere on instrument 2402 (e.g., on transmission mechanism 2404's housing). Other connectors for, e.g., optical fiber lasers, optical fiber distal bend or force sensors, irrigation, suction, etc. may be included. As shown, transmission mechanism 2404's housing is roughly wedge-or pie-shaped to allow it to be closely positioned to similar housings, as illustrated below.

Figure 11:
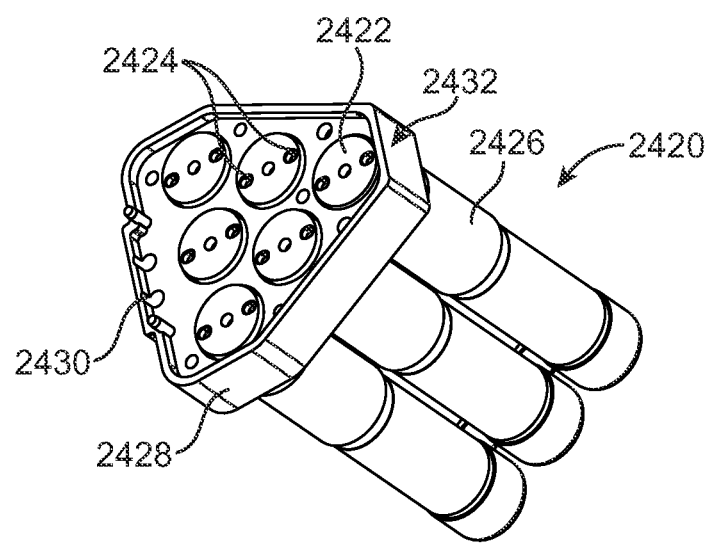
FIG. 11 is a perspective view of a segment of an actuator assembly that mates with and actuates the instrument shown in FIG. 10.

FIG. 11 is a perspective view of a portion of an actuator assembly 2420 that mates with and actuates components in surgical instrument 2402. Actuator disks 2422 are arranged to mate with interface disks 2410. Holes 2424 in disks 2422 are aligned to receive pins 2412 in only a single 360-degree orientation. Each disk 2422 is turned by an associated rotating servomotor actuator 2426, which receives servocontrol inputs as described above. A roughly wedge-shaped mounting bracket 2428, shaped to correspond to instrument 2402's transmission mechanism housing, supports the disks 2422, servomotor actuators 2426, and an electronic interface 2430 that mates with instrument 2402's interface connectors 2414. In one instance instrument 2402 is held against actuator assembly 2420 by spring clips (not shown) to allow easy removal. As shown in FIG. 11, a portion 2432 of actuator assembly housing 2428 is truncated to allow instrument body tube 2406 to pass by. Alternatively, a hole may be placed in the actuator assembly to allow the body tube to pass through. Sterilized spacers (reusable or disposable; usually plastic) may be used to separate the actuator assembly and the instrument's transmission mechanism to maintain a sterile surgical field. A sterile thin plastic sheet or "drape" (e.g., 0.002-inch thick polyethylene) is used to cover portions of the actuator assembly not covered by the spacer, as well as to cover portions of the manipulator arm. U.S. Pat. No. 6,866,671, incorporated by reference above, discusses such spacers and drapes.

Figure 12:
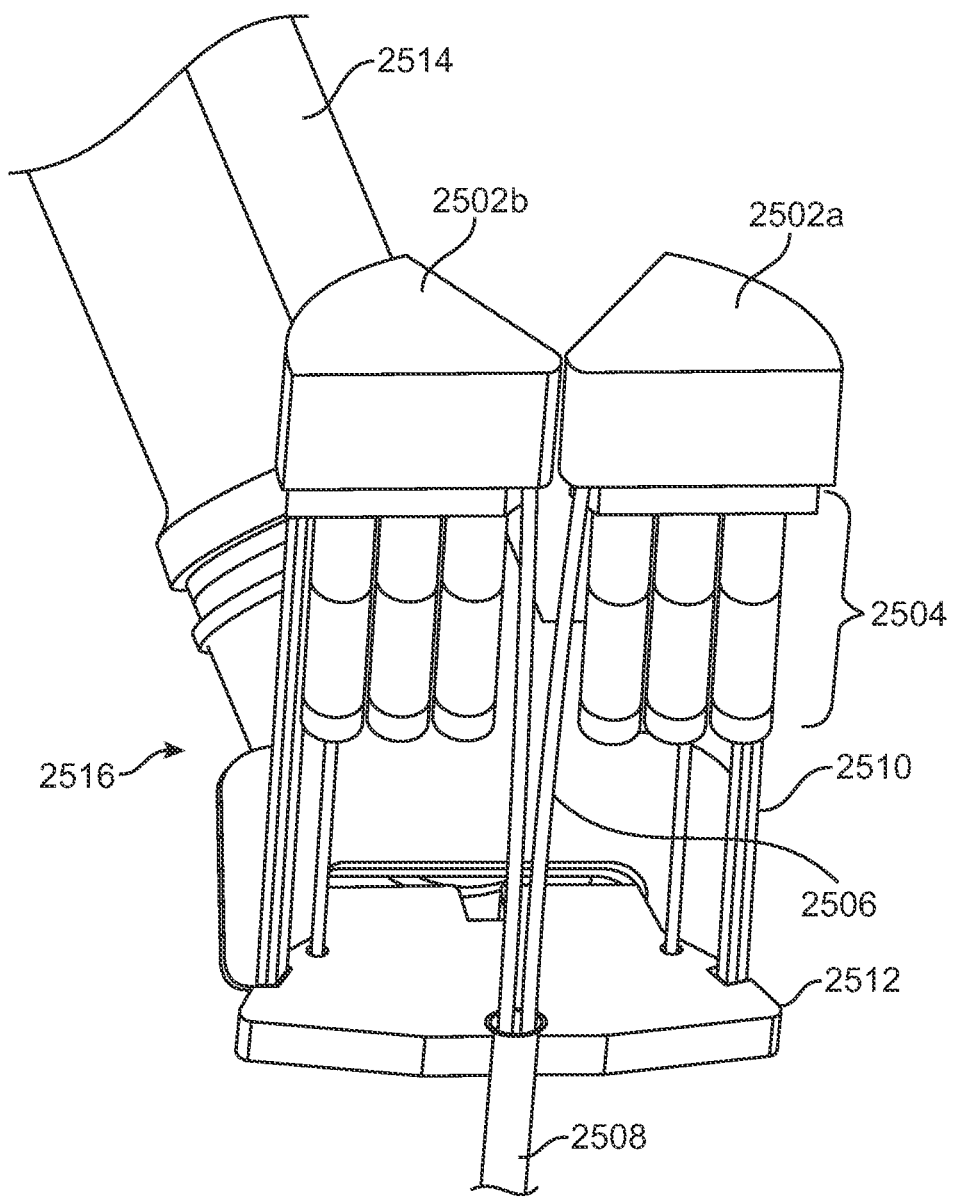
FIG. 12 is a diagrammatic perspective view that illustrates mounting minimally invasive surgical instruments and actuator assemblies at the end of a setup arm.

FIG. 12 is a diagrammatic perspective view that illustrates aspects of mounting minimally invasive surgical instruments and their associated actuator assemblies at the end of a setup/manipulator arm. As shown in FIG. 12, surgical instrument 2502a is mounted on actuator assembly 2504, so that the transmission mechanism mates with the actuator assembly (optional spacer/drape is not shown) as described above. Instrument 2502a's body tube 2506 extends past actuator assembly 2504 and enters a port in rigid guide tube 2508. As depicted, body tube 2506, although substantially rigid, is bent slightly between the transmission mechanism housing and the guide tube as discussed above with reference to FIG. 5. This bending allows the instrument body tube bores in the entry guide to be spaced closer than the size of their transmission mechanisms would otherwise allow. Since the bend angle in the rigid instrument body tube is less than the bend angle for a flexible (e.g., flaccid) instrument body, cables can be stiffer than in a flexible body. High cable stiffness is important because of the number of distal DOFs being controlled in the instrument. Also, the rigid instrument body is easier to insert into a guide tube than a flexible body. In one embodiment the bending is resilient so that the body tube assumes its straight shape when the instrument is withdrawn from the guide tube (the body tube may be formed with a permanent bend, which would prevent instrument body roll). Actuator assembly 2504 is mounted to a linear actuator 2510 (e.g. a servocontrolled lead screw and nut or a ball screw and nut assembly) that controls body tube 2506's insertion within guide tube 2508. The second instrument 2502b is mounted with similar mechanisms as shown. In addition, an imaging system (not shown) may be similarly mounted.

FIG. 12 further shows that guide tube 2508 is removably mounted to support platform 2512. This mounting may be, for example, similar to the mounting used to hold a cannula on a da Vinci® Surgical System manipulator arm. Removable and replaceable guide tubes allow different guide tubes that are designed for use with different procedures to be used with the same telemanipulative system (e.g., guide tubes with different cross-sectional shapes or various numbers and shapes of working and auxiliary channels). In turn, actuator platform 2512 is mounted to robot manipulator arm 2514 (e.g., 4 DOF) using one or more additional actuator mechanisms (e.g., for pitch, yaw, roll, insertion). In turn, manipulator arm 2514 may be mounted to a passive setup arm, as described above with reference to FIG. 1.

Figure 13:
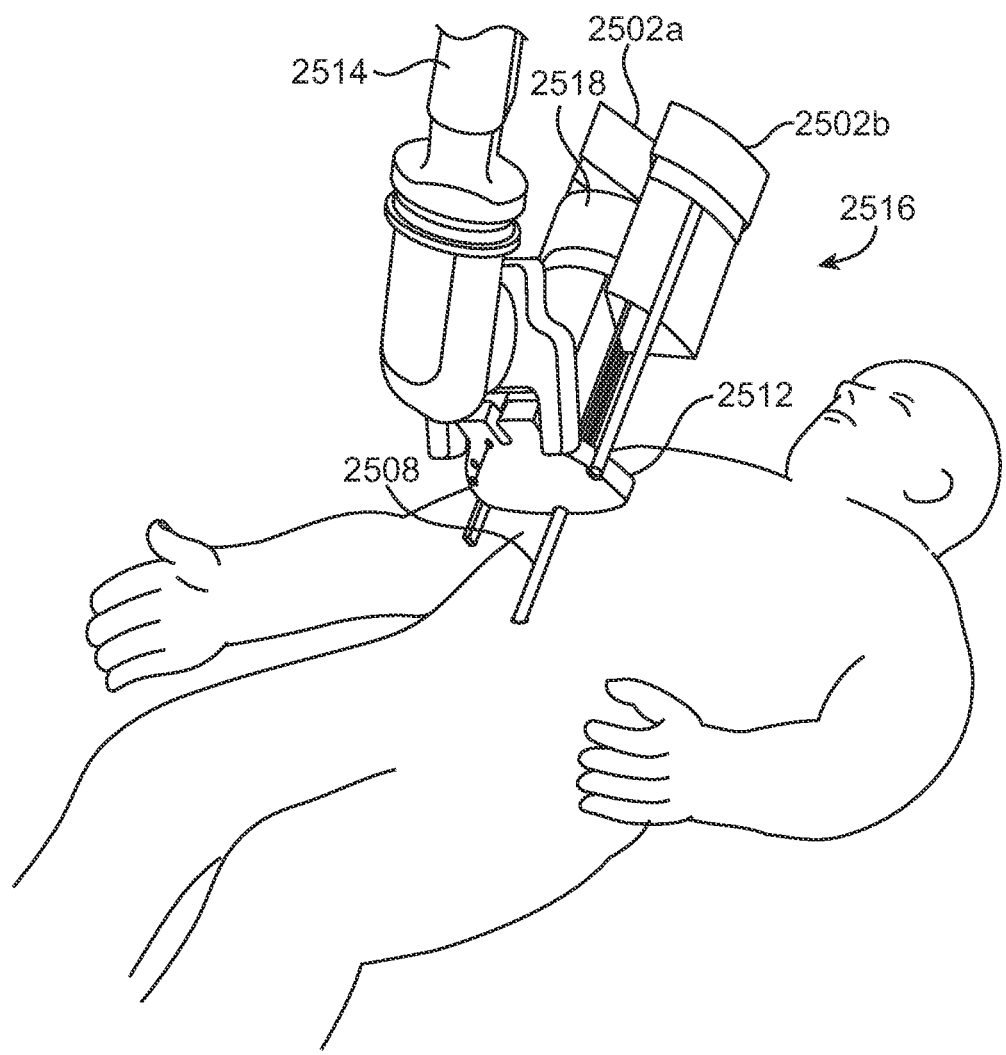
FIG. 13 is another diagrammatic perspective view that illustrates mounting minimally invasive surgical instruments and actuator assemblies at the end of a setup arm.

FIG. 13 is a diagrammatic perspective view that illustrates aspects shown in FIG. 12 from a different angle and with reference to a patient. In FIG. 13, arm 2514 and platform 2512 are positioned so that guide tube 2508 enters the patient's abdomen at the umbilicus. This entry is illustrative of various natural orifice and incision entries, including percutaneous and transluminal (e.g., transgastric, transcolonic, transrectal, transvaginal, transrectouterine (Douglas pouch), etc.) incisions. FIG. 13 also illustrates how the linear actuators for each instrument/imaging system operate independently by showing imaging system 2518 inserted and instruments 2502a, 2502b withdrawn. These aspects may apply to other surgical instrument assemblies described herein (e.g., flexible guide tubes with end-or side-exit ports, side working tools, etc.). It can be seen that in some instances the manipulator arm moves to rotate guide tube 2508 around a remote center 2520 at the entry port into a patient. If intermediate tissue restricts movement around a remote center, however, the arm can maintain guide tube 2508 in position.

FIG. 14 is a diagrammatic view that illustrates aspects of transmission mechanisms associated with flexible coaxial guide tubes and instruments. FIG. 14 shows primary guide tube 2702 running coaxially through and exiting the distal end of secondary guide tube 2704. Likewise, secondary guide tube 2704 runs coaxially through and exits the distal end of tertiary guide tube 2706. Transmission and actuator mechanism 2708 is associated with tertiary guide tube 2706. Transmission and actuator mechanism 2710 is associated with secondary guide tube 2704, and a proximal segment of guide tube 2704 extends through (alternatively, adjacent to) transmission and actuator mechanism 2710 before entering tertiary guide tube 2706. Likewise, transmission and actuator mechanism 2712 is associated with primary guide tube 2702, and a proximal segment of guide tube 2702 extends through (alternatively, adjacent to) transmission and actuator mechanisms 2708,2710 before entering secondary and tertiary guide tubes 2704,2706. Transmission mechanisms for instruments and an imaging system (not shown) running through and exiting the distal ends of channels 2714 in primary guide tube 2702 may be similarly stacked generally along the instrument assembly's longitudinal axis, or they may be arranged around guide tube 2702's extended longitudinal axis at its proximal end as described above. Or, the controller positions may be combined side-by-side and stacked, such as for a side-exit assembly in which transmission mechanisms for the side-exiting components are positioned side-by-side, and both are stacked behind the guide tube transmission mechanism. Intermediate exit assemblies may be similarly configured. Instrument and/or imaging system actuators and controls may also be combined within the same housing as an actuator and transmission mechanism for a guide tube.

In many aspects the devices described herein are used as single-port devices—all components necessary to complete a surgical procedure enter the body via a single entry port. In some aspects, however, multiple devices and ports may be used. FIG. 15 is a diagrammatic view that illustrates multiport aspects as three surgical instrument assemblies enter the body at three different ports. Instrument assembly 2802 includes a primary guide tube, a secondary guide tube, and two instruments, along with associated transmission and actuator mechanisms, as described above. In this illustrative example, instrument assembly 2804 includes a primary guide tube, a secondary guide tube, and a single instrument, along with associated transmission and actuator mechanisms, as described above. Imaging system assembly 2806 includes a guide tube and an imaging system, along with associated transmission and actuator mechanisms, as described above. Each of these mechanisms 2802,2804,2806 enters the body 2808 via a separate, unique port as shown. The devices shown are illustrative of the various rigid and flexible aspects described herein.

FIG. 16 is another diagrammatic view that illustrates multiport aspects. FIG. 16 shows three illustrative instruments or assemblies 2810 entering different natural orifices (nostrils, mouth) and then continuing via a single body lumen (throat) to reach a surgical site.

Figure 17:
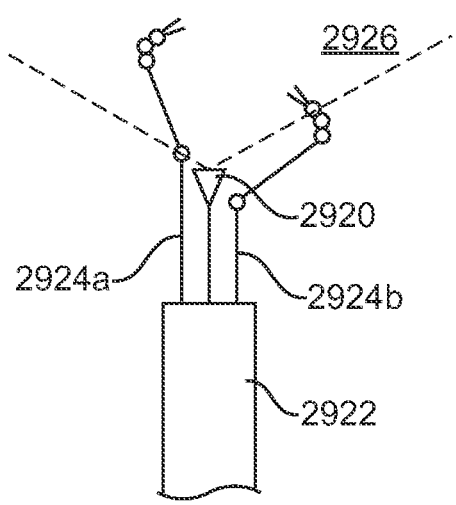
FIGS. 17-19 are diagrammatic plan views that illustrate further aspects of preventing undesired instrument collision with tissue.
Figure 18:
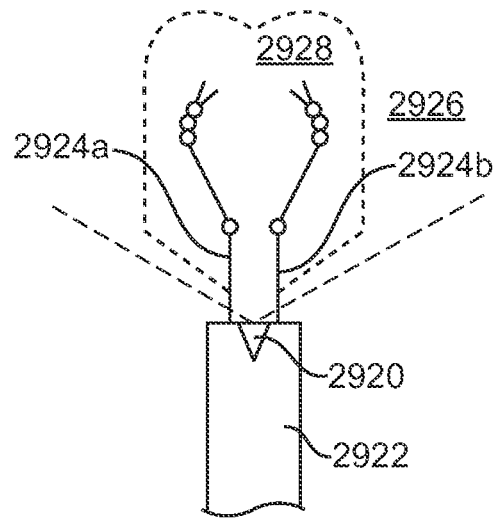
Figure 19:
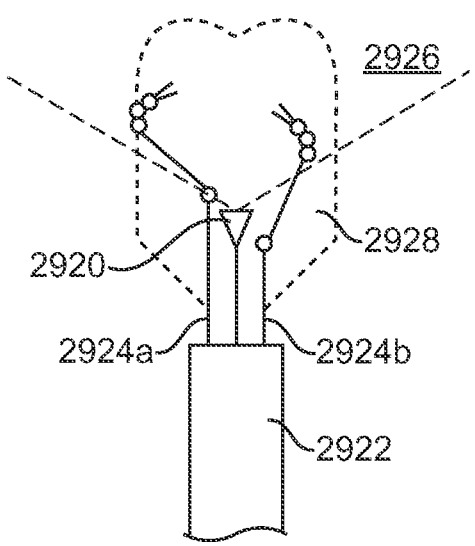

FIGS. 17-19 are diagrammatic plan views that illustrate aspects of preventing undesired instrument collision with tissue. Instruments may collide with patient tissue outside of an imaging system's field of view in spaces confined by patient anatomy (e.g., laryngeal surgery). Such collisions may damage tissue. For multi-DOF surgical instruments, some DOFs may be inside the field of view while other, more proximal DOFs may be outside the field of view. Consequently, a surgeon may be unaware that tissue damage is occurring as these proximal DOFs move. As shown in FIG. 17, for example, an endoscopic imaging system 2920 extends from the end of guide tube 2922. The left side working instrument 2924a is placed so that all DOFs are within imaging system 2920's field of view 2926 (bounded by the dashed lines). The right side working instrument 2924b, however, has proximal DOFs (an illustrative parallel motion mechanism as described above and wrist are shown) that are outside field of view 2926, even though instrument 2924b's end effector is within field of view 2926. This instrument position is illustrative of tasks such as tying sutures.

In one aspect, field of view boundaries can be determined when the camera is manufactured so that the boundaries are known in relation to the camera head (image capture component). The boundary information is then stored in a nonvolatile memory associated with the imaging system that incorporates the camera head. Consequently, the control system can use the imaging system instrument's kinematic and joint position information to locate the camera head relative to the working instruments, and therefore the control system can determine the field of view boundaries relative to the working instruments. Instruments are then controlled to work within the boundaries.

In another aspect for stereoscopic imaging systems, field of view boundaries can be determined relative to the instruments by using machine vision algorithms to identify the instruments and their positions in the field of view. This "tool tracking" subject is disclosed in U.S. patent application Publication No. U.S. 2006/0258938 A1 (Hoffman et al.), which is incorporated by reference.

As shown in FIG. 18, imaging system 2920 is placed so that the camera head is just at the distal end of guide tube 2922. Instruments 2924a and 2924b are extended from the distal end of the guide tube and within imaging system 2920's field of view. An "Allowable Volume" is defined to be coincident with the field of view boundaries. The control system prevents any part of instruments 2924a and 2924b from moving outside the Allowable Volume. Since the surgeon can see all distal moving parts of instruments 2924a and 2924b, the surgeon then moves the instruments without colliding with surrounding tissue. The instrument movements are recorded, and an "Instrument Volume" 2928 (bounded by the dotted lines), which is bounded by the farthest movements of the instruments, is determined. The Instrument Volume is a convex volume within which instruments may be moved without colliding with tissue.

Next, imaging system 2920 is inserted as shown in FIG. 19. As a result, field of view 2926 is also inserted, and parts of instruments 2924a,2924b are outside of the inserted field of view 2926. A new Allowable Volume is determined to be the newly inserted field of view plus the previously determined Instrument Volume that is outside of the field of view. Therefore, the control system will allow the surgeon to move an instrument anywhere within the new Allowable Volume. The process may be repeated for further field of view insertions or for guide tube 2922 movements. This scheme allows a surgeon to define the allowable instrument range of motion in real time without requiring a tissue model. The surgeon is only required to trace the boundaries of the instrument range of motion inside the field of view, and the control system will record this information as the field of view is changed.

Figure 20:
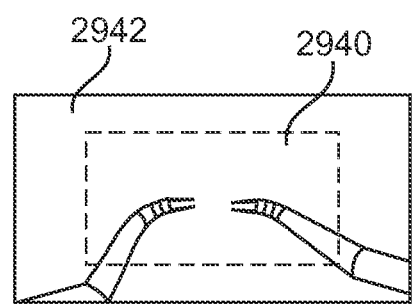
FIG. 20 is a diagrammatic view of an image mosaiced output display for a surgeon.

Another way to prevent unwanted instrument/tissue collision is by using image mosaicing. FIG. 20 is a diagrammatic view of a display (e.g., stereoscopic) that a surgeon sees during a surgical procedure. As shown in FIG. 20, the image from the new, more inserted field of view 2940 (bounded by the dashed lines) is registered and mosaiced with the image from the old, more withdrawn field of view 2942. Image mosaicing is known (see e.g., U.S. Pat. No. 4,673,988 (Jansson et al.) and U.S. Pat. No. 5,999,662 (Burt et al.), which are incorporated by reference) and has been applied to medical equipment (see e.g., U.S. Pat. No. 7,194,118 (Harris et al.), which is incorporated by reference). As a result, the surgeon sees an area larger than the current, more inserted field of view. A kinematically accurate graphical simulation of the instruments is shown in the old field of view 2942 so that the surgeon can see possible collisions in this region as the instruments move.

Figure 21:
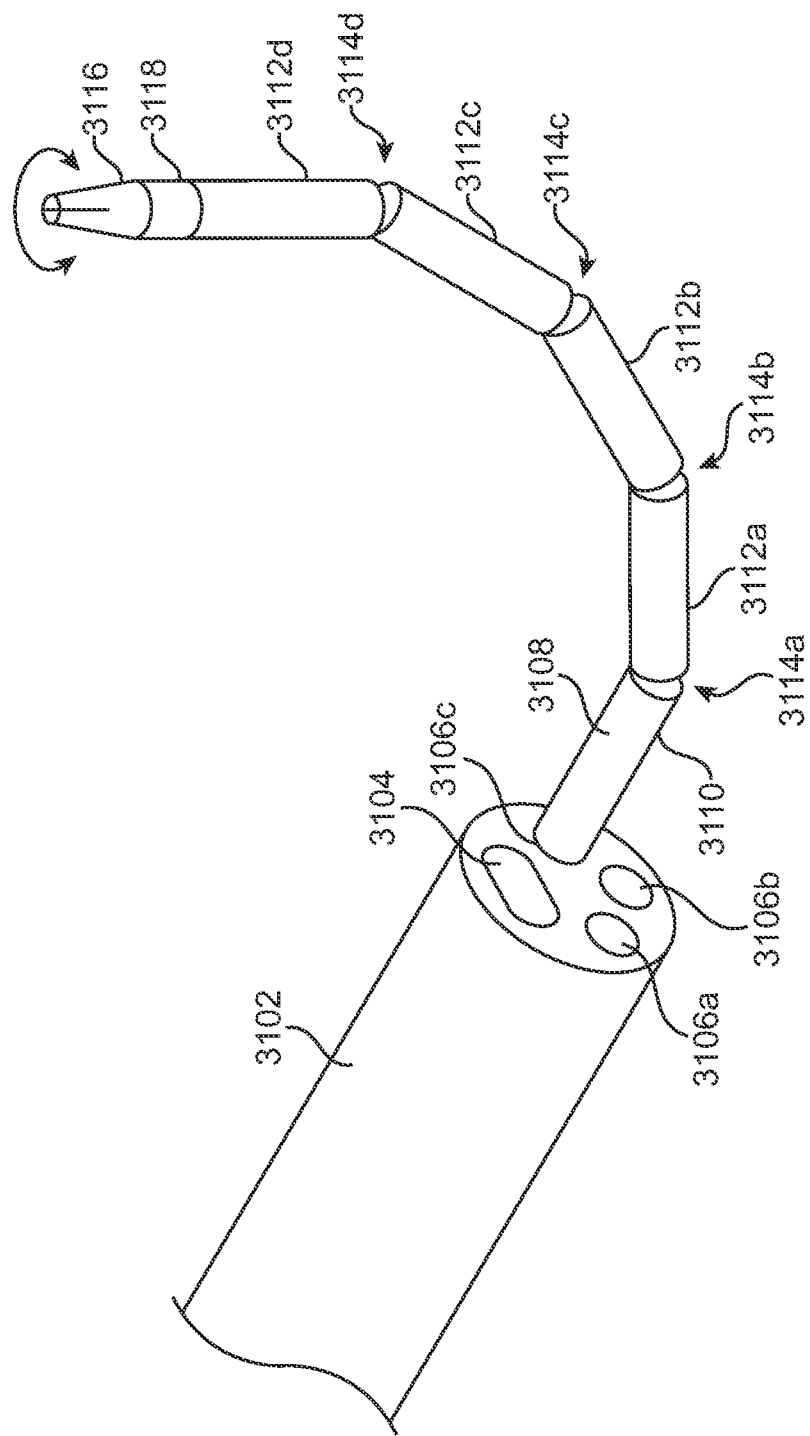
FIG. 21 is a diagrammatic perspective view of an illustrative minimally invasive surgical instrument assembly that includes a multi-jointed instrument dedicated to retraction.

FIG. 21 is a diagrammatic perspective view that shows aspects of an illustrative minimally invasive surgical instrument assembly that includes a multi-jointed instrument dedicated to retraction. As shown in FIG. 21, guide tube 3102 includes a channel 3104, through which an imaging system is inserted, and three channels 3106a,3106b,3106c, through which surgical instruments may be inserted. Retraction instrument 3108 is shown extending through channel 3106c.

As depicted, retraction instrument 3108 includes a proximal instrument body 3110 and four serial links 3112a-d. Four joints 3114a-d couple proximal instrument body 3110 and links 3112a-d together. In one aspect, each joint 3114a-d is an independently controllable single DOF pitch joint. In other aspects the joints may have additional DOFs. An actively controlled (either hand or telemanipulated) gripper 3116 is mounted at the distal end of the most distal link 3112d via a passive roll joint 3118. In some aspects other end effectors, or none, may be substituted for the gripper. In one aspect the combined length of links 3112a-d and gripper 3116 is sufficient to retract tissue beyond the working envelope of instruments that extend through channels 3106a and 3106b. For example, the combined lengths of the links and the gripper may be approximately equal to the full insertion range (e.g., approximately 5 inches) of the instruments. Four links and joints are shown, and other numbers of links and joints may be used. Retraction is done using various combinations of pitching joints 3114a-d and rolling instrument 3108 within channel 3106c.

For performing a retraction, instrument 3108 is inserted so that each joint 3114a-d is exposed one after the other. Insertion depth may be varied so that retraction can begin at various distances from the distal end of the guide tube with various numbers of joints as the joints exit from the guide tube's distal end. That is, for example, retraction may begin as soon as joint 3114d is inserted past the distal end of the guide tube. For retraction, gripper 3116 may grip tissue. Passive roll joint 3118 prevents the gripped tissue from being torqued as instrument 3108 is rolled within channel 3106c. In one aspect, the control system couples the motions of instrument 3108 and guide tube 3102. This coupled control of motion allows tissue to be held in place by gripper 3116 as the guide tube is moved to the left or right "underneath" the retracted tissue. For example, as the distal end of guide tube 3102 is moved to the left, instrument 3108 is rolled (and joint 3114a-d pitch may be changed) to move gripper 3116 to the right.

Figure 31:
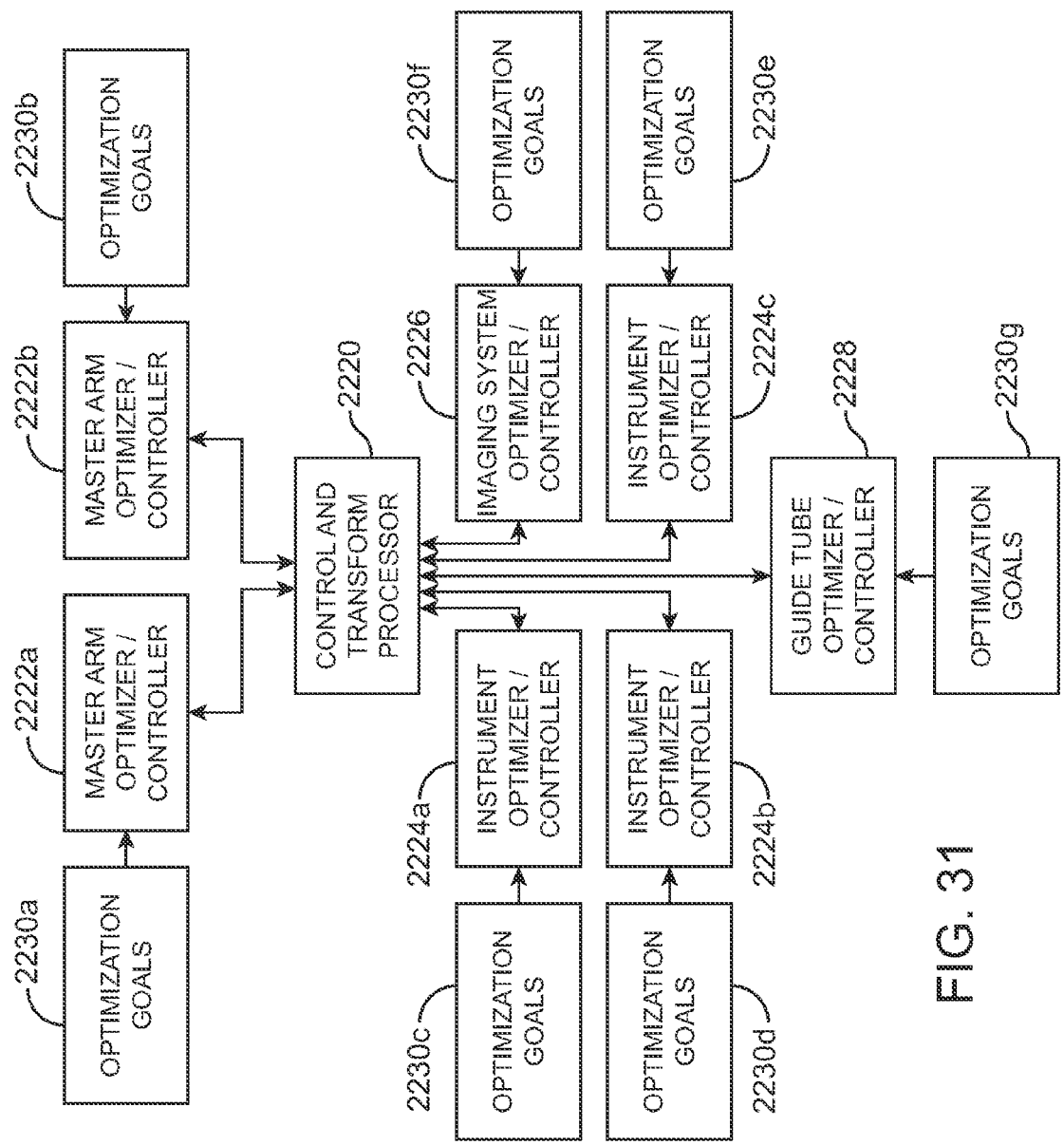
FIG. 31 is a diagrammatic view of a distributed motion control system for a minimally invasive telesurgical system.

FIG. 21 further illustrates an aspect of instrument position and control within guide tubes. The working surgical instruments need not be inserted though guide tube channels that correspond to or are aligned with their working position. For example, as shown in FIG. 31 the left side working instrument does not have to be inserted through the left-most channel 3106c. Instead, the left side working instrument may be inserted via the "bottom" channel 3106b. The right side working instrument may then be inserted via the right-most channel 3106a. Then, the left and right side working instruments may be controlled to work at a surgical site in alignment with the field of view of an imaging system inserted via channel 3104 that has not been rolled or yawed. Stated another way, the left-right axis between the working instruments' insertion channels does not have to be aligned with the left-right axis between the working instruments' end effectors at the surgical site or with the left-right axis interpupillary axis of the stereoscopic imaging system. Further, by the control system recognizing which instrument is coupled to each particular actuator, left-right instrument position may be varied. For example, retraction instrument 3108 may be inserted via channel 3106a, the right side working instrument may be inserted via channel 3106b, and the left side working instrument may be inserted via channel 3106c. In some aspects, with appropriately shaped channels and/or imaging systems, the imaging system may be inserted via one of several channels. For example, "top" channel 3104 and "bottom" channel 3106b may be oblong shaped with a center bore that holds a cylindrical instrument body. Consequently, an imaging system may be inserted via the "top" or "bottom" channel, and a working instrument may be inserted via the other "top" or "bottom" channel.

Figure 22:
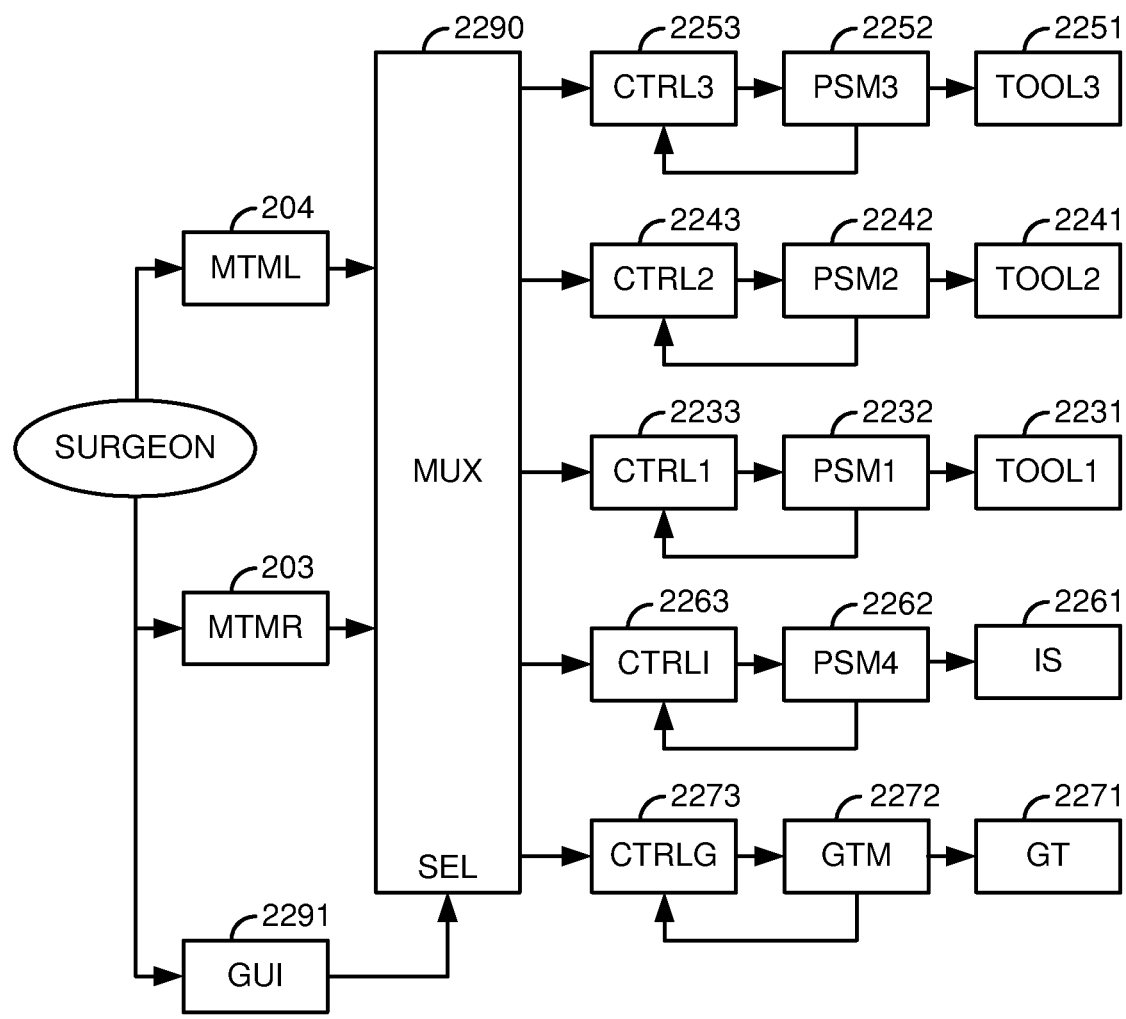
FIG. 22 is a block diagram of components used for controlling and selectively associating devices on a patient side support system with input devices in a telesurgical system.

FIG. 22 is a block diagram of components used for controlling and selectively associating medical devices on the patient side support system 2104 to operator manipulated input devices 203, 204 of the surgeon's console 2102. Various surgical tools such as graspers, cutters, and needles may be used to perform a medical procedure at a work site within the Patient. In this example, three surgical tools (TOOL1, TOOL2,TOOL3) 2231,2241,2251 are used to robotically perform the procedure and the imaging system (IS) 2261 is used to view the procedure. The tools 2231,2241,2251 and imaging system 2261 may be disposed in a guide tube (GT) 2271 so as to be extendable beyond a distal end of the guide tube 2271. The guide tube 2271 may be inserted into the Patient through an entry aperture such as a minimally invasive incision or a natural orifice using the setup portion of a robotic arm assembly and maneuvered by a guide tube manipulator 2272 towards the work site where the medical procedure is to be performed.

Each of the devices 2231,2241,2251,2261,2271 is manipulated by its own manipulator. In particular, the imaging system 2261 is manipulated by an imaging system manipulator (PSM4) 2262, the first surgical tool 2231 is manipulated by a first tool manipulator (PSM1) 2232, the second surgical tool 2241 is manipulated by a second tool manipulator (PSM2) 2242, the third surgical tool 2251 is manipulated by a third tool manipulator (PSM3) 2252, and the guide tube 2271 is manipulated by a guide tube manipulator 2272.

Each of the instrument manipulators 2232,2242,2252,2262 is a mechanical assembly that carries actuators and provides a mechanical, sterile interface to transmit motion to its respective articulated instrument. Each instrument 2231,2241,2251,2261 is a mechanical assembly that receives the motion from its manipulator and, by means of a cable transmission, propagates the motion to its distal articulations (e.g., joints). Such joints may be prismatic (e.g., linear motion) or rotational (e.g., they pivot about a mechanical axis). Furthermore, the instrument may have internal mechanical constraints (e.g., cables, gearing, cams, belts, etc.) that force multiple joints to move together in a predetermined fashion. Each set of mechanically constrained joints implements a specific axis of motion, and constraints may be devised to pair rotational joints (e.g., joggle joints). Note also that in this way the instrument may have more joints than the available actuators.

In direct control mode, each of the input devices 203,204 may be selectively associated with one of the devices 2261, 2231,2241,2251, 2271 through a multiplexer (MUX) 2290 so that the associated device may be controlled by the input device through its controller and manipulator. For example, the Surgeon may specify the association through a graphical user interface (GUI) 2291 on the surgeon's console 2102 for the left and right input devices 203,204 to be respectively associated with the first and second surgical tools 2231, 2241, which are telerobotically controlled through their respective controllers 2233, 2243 and manipulators 2232,2242 so that the Surgeon may perform a medical procedure on the Patient while the surgical tool 2251, imaging system 2261 and guide tube 2271 are each soft locked in place through their respective controllers (such as shown in FIGS. 24, 25). If the Surgeon desires to control movement of the surgical tool 2251 using one of the input devices 203,204, then the Surgeon may do so by simply disassociating the input device from its currently associated device and associating it instead to the tool 2251. Likewise, if the Surgeon desires to control movement of either the imaging system 2261 or guide tube 2271 using one or both of the input devices 203,204, then the Surgeon may do so by simply disassociating the input device from its currently associated device and associating it instead to the imaging system 2261 or guide tube 2271.

As alternatives to using the GUI 2291 for providing selection input SEL for the MUX 2290, the selective association of the input devices 203,204 to devices 2251,2241,2231,2261, 2271 may be performed by the Surgeon using voice commands understood by a voice recognition system, or by the Surgeon depressing a button on one of the input devices 203,204, or by the Surgeon depressing a foot pedal on the surgeon's console 2102, or by the Surgeon using any other well known mode switching technique. Although such mode switching is described herein as being performed by the Surgeon, it may alternatively be performed by an Assistant under the direction of the Surgeon.

Figure 23:
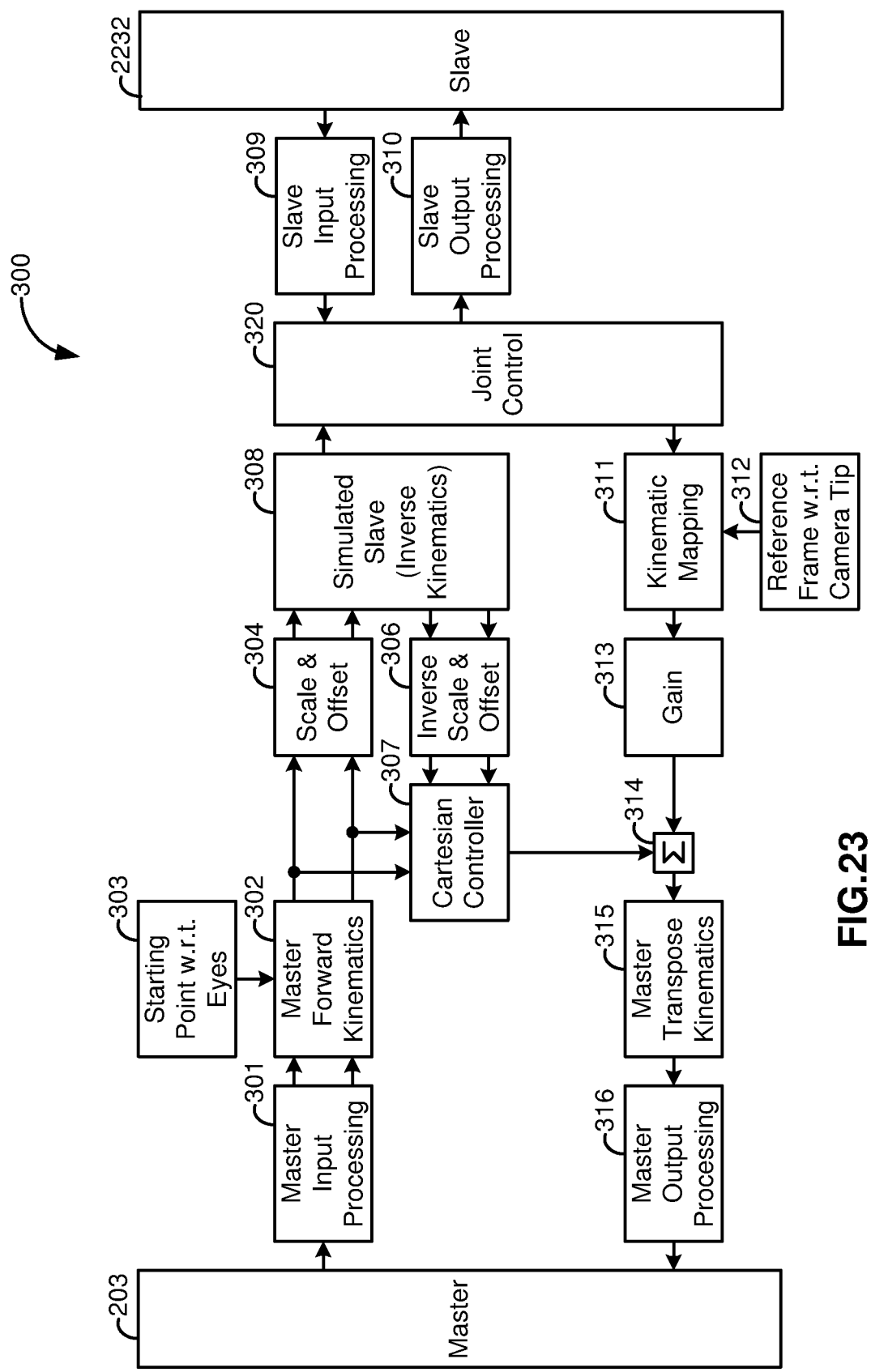
FIG. 23 is a block diagram of a master/slave control system included in manipulator controllers in the telesurgical system.

Each of the controllers 2233,2243,2253,2263,2273 comprises a master/slave control system. FIG. 23 illustrates, as an example, a block diagram of a master/slave control system 300 for controlling movement of the tool slave manipulator 2232 when it is associatecd with the input device 203 and consequently, the position and orientation of its attached tool 2231, as commanded by movement of the master manipulator 203 by the Surgeon. A similar master/slave control system may be provided for each of the other slave manipulators (e.g., 2241,2251,2261,2271) in the system 2100.

Both the master and slave manipulators include a number of linkages connected by joints so as to facilitate multiple degrees-of-freedom movement. As the Surgeon moves the master manipulator 203 from one position to another during the course of performing a surgical procedure, sensors associated with the master manipulator joints provide information indicating such command movement in master joint space, and sensors associated with the slave manipulator joints provide information indicating slave manipulator and consequently, tool 2231 movement in slave joint space for feedback purposes.

A master input processing unit 301 receives the information of the master joint positions, which are sampled at the control system processing rate (e.g., 1300 Hz in the present example), from the master joint sensors in the master manipulator 203, and computes joint velocities from the sensed joint positions. A master forward kinematics processing unit 302 receives the master joint positions and velocities from the master input processing unit 301, transforms them from master joint space to corresponding positions and velocities of the master frame (i.e., the frame associated with the master manipulator 203) in Cartesian space relative to the eye reference frame (i.e., the reference frame associated with the position of the surgeon's eyes), using, for example, a Jacobian matrix and eye related information separately determined and provided in block 303.

A scale and offset processing unit 304 receives the Cartesian position and velocity commands from the master forward kinematics processing unit 302, scales the commanded movement according to a scale factor selected to perform the surgical procedure, and takes into account offsets to generate desired slave tool frame (i.e., the frame associated with the tool 2231) positions and velocities. For economy of words, Cartesian position is to be interpreted to include Cartesian orientation in this specification where appropriate, Cartesian velocity is to be interpreted to include translational and angular velocities where appropriate. The scale adjustment is useful where small movements of the slave manipulator 2232 are desired relative to larger movement of the master manipulator 203 in order to allow more precise movement of the slave tool 2231 at the surgical site. The offsets, on the other hand, determine, for example, the corresponding position and/or orientation of an end effector frame (e.g., the frame associated with an end effector of the tool 2231) in the camera reference frame (i.e., the frame associated with the image capturing end of the imaging system) relative to a position and orientation of the master frame in the eye reference frame.

A simulated slave processing unit 308 (also referred to as a "simulated domain") receives desired slave tool frame position and velocity commands from the scale and offset processing unit 304, and limits the desired slave tool frame position, orientation and velocities, to assigned Cartesian limits for instance to enforce correct and intuitive operation of the tool 2231 by keeping it within its dexterous workspace and to prevent motions that would result in excessive forces being exerted by the end effector of the tool 2231. The simulated slave processing unit 308 generates simulated slave joint positions and velocities corresponding to the limited slave tool frame positions and velocities, while making sure that the generated slave joint positions and velocities do not exceed the actual slave joint's range of motion and maximum velocities (i.e., joint limits) even in the vicinity of kinematic singularities for the slave kinematics.

An inverse scale and offset processing unit 306 receives the simulated joint position and velocity commands from the simulated slave processing unit 308, and performs an inverse function to that of the scale and offset processing unit 304 on them. A Cartesian controller 307 receives as first inputs, the inputs to the scale and offset processing unit 304 and as second inputs, the outputs of the inverse scale and offset processing unit 306. The Cartesian controller 307 then generates an error signal as a difference of the first and second inputs, and a Cartesian force "$F_{CART}$" from the error signal such as with the following formula:

$$F_{CART} = K(\Delta x) + B(\Delta \dot{x}) \quad (1)$$

where "K" is a spring constant, "B" is a damping constant, "$\Delta \dot{x}$" is the difference between the Cartesian velocity inputs to the Cartesian controller 307 and "$\Delta x$" is the difference between the Cartesian position inputs to the Cartesian controller 307. For an orientation error, a corresponding torque in Cartesian space is determined.

A master transpose kinematics processing unit 315 receives the Cartesian force $F_{CART}$ through a summation node 314, and generates a corresponding torque in joint space using, for example, the Jacobian transpose matrix and kinematic relationships associated with the master manipulator 203. A master output processing unit 316 receives the master torque signals from the master transpose kinematics processing unit 315, generates electrical currents corresponding to the master torque signals, and supplies the electrical currents to corresponding master joint motors of the master manipulator 203. As a result, a surgeon operating the master manipulator 203 feels the Cartesian force, $F_{CART}$, whenever the surgeon is commanding a position or velocity which exceeds system Cartesian or slave joint limits, or would result in a kinematic singularity condition for the slave manipulator 2232.

As the master input processing unit 301 is receiving master joint positions from sensors in the master manipulator 203, a slave input processing unit 309 is also receiving slave joint positions from position sensors in the slave manipulator 2232 at the control system processing rate. A joint control unit 320 receives the slave joint positions from the slave input processing unit 309 and the simulated joint position commands provided from the simulated slave processing unit 308, and generates slave torque command signals for the slave joint motors and master torque feedback command signals for the master joint motors.

The slave torque command signals are generated by the joint control unit 320 so as to drive joints of the slave manipulator until feedback errors calculated in the joint control unit 320 zero out. A slave output processing unit 310 receives the slave torque command signals from the joint control unit 320, converts them into appropriate electrical currents, and supplies the electrical currents to the joint motors of the slave manipulator so as to drive the motors accordingly.

The master torque feedback command signals are generated by the joint control unit 320 as a function of the slave joint position and velocity tracking errors so as to reflect forces being exerted against the tool 2231 or its slave manipulator 2232 back to the master manipulator 203 so that they may be felt by the Surgeon. A kinematic mapping unit 311 receives the master torque feedback command signals from the joint control unit 320, and generates the corresponding Cartesian force being exerted against the tip of the tool 2231 relative to the camera frame of the imaging system using the slave kinematic configuration and the previously calculated slave reference frame position information provided in block 312.

A gain 313 adjusts the magnitude of the Cartesian force so as to ensure system stability while providing adequate force sensation to the Surgeon. The gain adjusted Cartesian force is then passed through the summation node 314, and processed along with the Cartesian force provided by the Cartesian controller 307 through the master transpose kinematics processing unit 315 and master output processing 316 as previously described in reference to their processing of the Cartesian force provided by the Cartesian controller 307.

Additional details related to conventional aspects of the master/slave control system 300, such as the various reference frames referred to herein and the calculation of the surgeon eye related information provided in block 303 and the slave reference frame information provided in block 312, which are based upon well-known mathematics, are described, for example, in previously incorporated by reference and U.S. Pat. No. 6,424,885, "Camera Referenced Control in a Minimally Invasive Surgical Apparatus" where the notion of reference frame is termed "slave fulcrum".

The joint control unit 320 includes a joint controller for each active joint and gear of the slave manipulator 2232 that is being controlled by the master/slave control system 300. In particular, where the slave manipulator 2232 includes various joints to move the tool 2231 through its operable workspace, each of these joints will have its own controller. To simplify the description herein and in the claims, the term "joint" is to be understood as a connection (translational or revolute) between two links, and may include gears (or prismatic joints) as well as any other controllable component coupled to linear drive mechanisms that may be used in controlling robotic arm assemblies.

Figure 26:
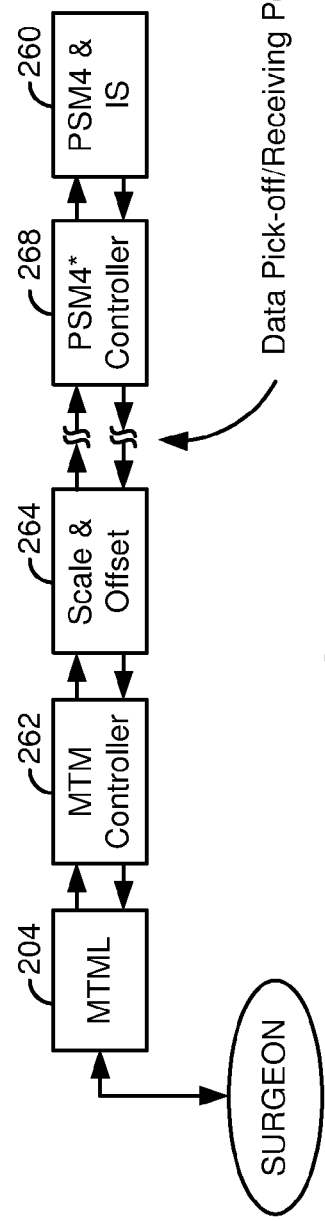
FIGS. 26-27 are block diagrams of a direct "imaging system" mode architecture implemented in the manipulator controllers in the telesurgical system.
Figure 27:
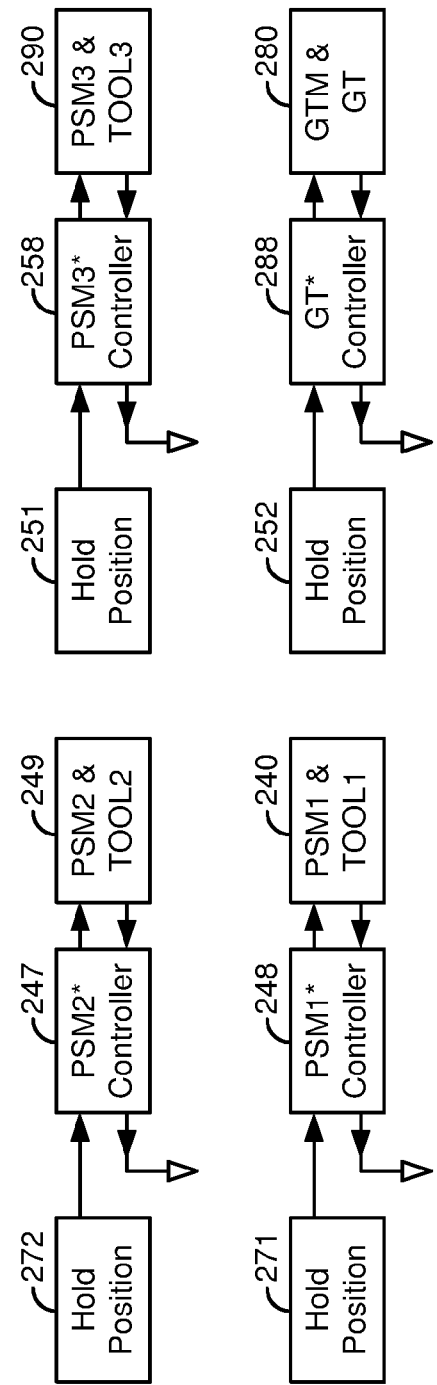

Direct control modes are control modes in which the user has direct control over a specific slave manipulator. All other slave manipulators (i.e., the ones that are not connected to a master device) are soft-locked (i.e., all their joints are held in place by their respective controllers). As an example, in a single-port system such as described herein, three direct control modes are defined as a direct "tool following" mode in which the two hand-operable input devices are associated with two tool slave manipulators and their respective tools, a direct "imaging system" mode in which one or both of the hand-operable input devices are associated with the imaging system, and a direct "guide tube" mode in which one or both hand-operable input devices are associated with the guide tube. For examples, FIGS. 24-25 illustrate a direct "tool following" mode in which the left and right master input devices 204,203 are respectively associated with the first and second tools while a third tool, the imaging system and the guide tube are held in place by their respective controllers; FIGS. 26-27 illustrate a direct "imaging system" mode in which the left master input device 204 is associated with the imaging system while the first tool, second tool, third tool and guide tube are held in place by their respective controllers; and FIGS. 28-29 illustrate a direct "guide tube" mode in which the left and right master input devices 204,203 are associated with the guide tube while the first tool, second tool, third tool and imaging system are held in place by their respective controllers.

As indicated in FIGS. 24,26,28, data pick-off/receiving points (respectively at the inputs to the inverse scale & offset blocks 306 and outputs of the scale & offset blocks 304 of the master/slave control systems implemented in the associated device controllers) are available to provide commanded state information to non-associated controllers for coupled control modes and receive state information back from the non-associated controllers, as described herein. To simplify the drawings, both the inverse scale & offset block 306 and scale & offset block 304 are included in a single block designated as "Scale & Offset" in the figures. Although data pick-off/receiving points respectively at the inputs to the inverse scale & offset blocks 306 and outputs of the scale & offset blocks 304 are used in these examples, it is to be appreciated that other data pick-off and receiving points may be used in practicing the various aspects of the present invention.

Also to simplify the figures, the master/slave control system 300 has been split into master and slave side portions (on opposite sides of the "Scale & Offset" blocks) with the PSM1* Controller 248, PSM2* Controller 247, PSM4* Controller 268, and GT* Controller 288 comprising the slave side components (e.g., control system 300 blocks 308,320,309, 310,311,312,313 of FIG. 23) and the MTM Controllers 241, 242,262,281,282 comprising the master side components (e.g., control system 300 blocks 301,302,303,307,314,315, 316 of FIG. 23). Hold position blocks 251,252,253,271,272 in FIGS. 25, 27, 29 indicate state commands (each indicating a constant position and orientation for its respective device) that are stored in one or more memory devices and respectively provided to the slave side PSM3* Controller 258, GT* Controller 288, PSM4* Controller 268, PSM1* Controller 248, and PSM2* Controller 247, while following data generated in these controllers are ignored (or otherwise discarded) as indicated by downward point arrows from these controllers, so that their respective manipulators and devices are held at the commanded states.

In a coupled control mode, the Surgeon is directly controlling movement of an associated slave manipulator (e.g., one of the manipulators 2232,2242,2252,2262,2272) while indirectly controlling movement of one or more non-associated slave manipulators, in response to commanded motion of the directly controlled slave manipulator, to achieve a secondary objective. Examples of secondary objective include optimizing device workspaces (i.e., maximizing their ranges of motion), optimizing the imaging system's view of other devices and/or the work site, minimizing the chance of collisions between devices and/or the patient's anatomy, and driving non-associated devices to desired poses. By automatically performing secondary tasks through coupled control modes, the system's usability is enhanced by reducing the Surgeon's need to switch to another direct mode to manually achieve the desired secondary objective. Thus, coupled control modes allow the Surgeon to better focus on performing the medical procedure and to pay less attention to managing the system. As described below, the user interface has three coupled control modes: a mode for the instrument(s), a mode for the imaging system, and a mode for guide tube (i.e. as many modes as the number of manipulators designed to perform different functions within the surgical system).

It is useful to provide haptic cues to the Surgeon to indicate when motion of a coupled manipulator occurs, since the Surgeon otherwise may not be aware of the movement of any device that is being indirectly controlled through a coupled control mode. This is not a problem for directly controlled devices, because the master/slave control system for such directly controlled devices generally provides a haptic feedback path. Therefore, a haptic cue such as a detent may be provided that signals to the Surgeon when a coupled mode becomes engaged.

The GUI 2291 used by the Surgeon to specify the association of inputs devices 203,204 and devices 2231,2241,2251, 2261,2271 may also be used by the Surgeon to specify various parameters of the coupled control modes. For example, the Surgeon may use the GUI 2291 to select which device manipulators participate in various coupled control modes and to define and/or prioritize the secondary objectives associated with the coupled control modes.

Figure 30:
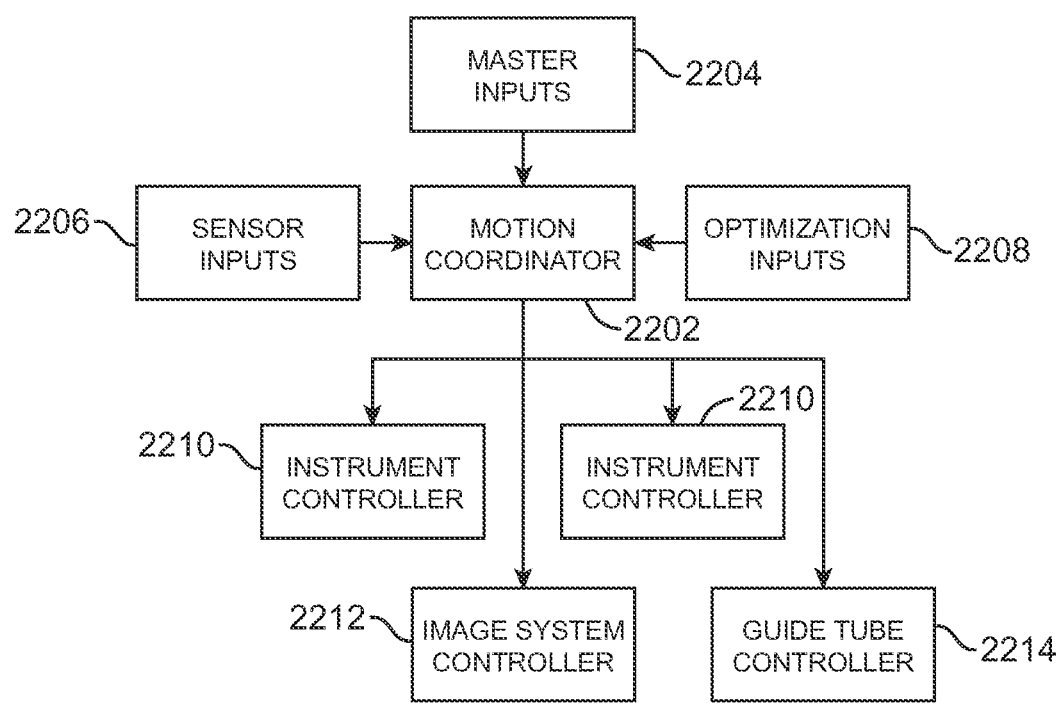
FIG. 30 is a diagrammatic view of a centralized motion control system for a minimally invasive telesurgical system.

FIG. 30 is a diagrammatic view that illustrates coupled control aspects of a centralized motion control and coordination system architecture for minimally invasive telesurgical systems that incorporate surgical instrument assemblies and components described herein. A motion coordinator system 2202 receives master inputs 2204, sensor inputs 2206, and optimization inputs 2208.

Master inputs 2204 may include the surgeon's arm, wrist, hand, and finger movements on the master control mechanisms. Inputs may also be from other movements (e.g., finger, foot, knee, etc. pressing or moving buttons, levers, switches, etc.) and commands (e.g., voice) that control the position and orientation of a particular component or that control a task-specific operation (e.g., energizing an electrocautery end effector or laser, imaging system operation, and the like).

Sensor inputs 2206 may include position information from, e.g., measured servomotor position or sensed bend information. U.S. patent application Ser. No. 11/491,384 (Larkin, et al.) entitled "Robotic surgery system including position sensors using fiber Bragg gratings", incorporated by reference, describes the use of fiber Bragg gratings for position sensing. Such bend sensors may be incorporated into the various instruments and imaging systems described herein to be used when determining position and orientation information for a component (e.g., an end effector tip). Position and orientation information may also be generated by one or more sensors (e.g., fluoroscopy, MRI, ultrasound, and the like) positioned outside of the patient, and which in real time sense changes in position and orientation of components inside the patient.

Optimization inputs 2208 relate to the secondary objectives. They may be high-level commands, or the inputs may include more detailed commands or sensory information. An example of a high level command would be a command to an intelligent controller to optimize a workspace. An example of a more detailed command would be for an imaging system to start or stop optimizing its camera. An example of a sensor input would be a signal that a workspace limit had been reached.

Motion coordinator 2202 outputs command signals to various actuator controllers and actuators (e.g., servomotors) associated with manipulators for the various telesurgical system arms. FIG. 30 depicts an example of output signals being sent to two instrument controllers 2210, to an imaging system controller 2212, and to a guide tube controller 2214. Other numbers and combinations of controllers may be used. The motion coordinator 2202 determines how to take advantage of the overall system kinematics (i.e., the total degrees of freedom of the system) to achieve the secondary objectives indicated by the optimization inputs 2208.

As an example, such a motion coordination system may be used to control surgical instrument assembly 1700 (FIG. 6). Instrument controllers 2210 are associated with instruments 1702a,1702b, imaging system controller 2212 is associated with imaging system 1704, and guide tube controller 2214 is associated with guide tube 1708. Accordingly, in some aspects the surgeon who operates the telesurgical system will simultaneously and automatically access at least the three control modes identified above: an instrument control mode for moving the instruments, an imaging system control mode for moving the imaging system, and a guide tube control mode for moving the guide tube. A similar centralized architecture may be adapted to work with the various other mechanism aspects described herein.

FIG. 31 is a diagrammatic view that illustrates aspects of a distributed motion control and coordination system architecture for minimally invasive telesurgical systems that incorporate surgical instrument assemblies and components described herein. In the illustrative aspects shown in FIG. 31, control and transform processor 2220 exchanges information with two master arm optimizer/controllers 2222a,2222b, with three surgical instrument optimizer/controllers 2224a, 2224b,2224c, with an imaging system optimizer/controller 2226, and with a guide tube optimizer/controller 2228. Each optimizer/controller is associated with a master or slave arm (which includes, e.g., the camera (imaging system) arm, the guide tube arm, and the instrument arms) in the telesurgical system. Each of the optimizer/controllers receives arm-specific optimization goals 2230a-2230g.

The double-headed arrows between control and transform processor 2220 and the various optimizer/controllers represents the exchange of Following Data associated with the optimizer/controller's arm. Following Data includes the full Cartesian configuration of the entire arm, including base frame and distal tip frame. Control and transform processor 2220 routes the Following Data received from each optimizer/controller to all the optimizer/controllers so that each optimizer/controller has data about the current Cartesian configuration of all arms in the system. In addition, the optimizer/controller for each arm receives optimization goals that are unique for the arm. Each arm's optimizer/controller then uses the other arm positions as inputs and constraints as it pursues its optimization goals. In one aspect, each optimization controller uses an embedded local optimizer to pursue its optimization goals. The optimization module for each arm's optimizer/controller can be independently turned on or off. For example, the optimization module for only the imaging system and the guide tube may be turned on.

The distributed control architecture provides more flexibility than the centralized architecture, although with the potential for decreased performance. It easier to add in a new arm and to change the overall system configuration if such a distributed control architecture is used rather than if a centralized architecture is used. In this distributed architecture, however, the optimization is local versus the global optimization that can be performed with the centralized architecture, in which a single module is aware of the full system's state.

Figure 32:
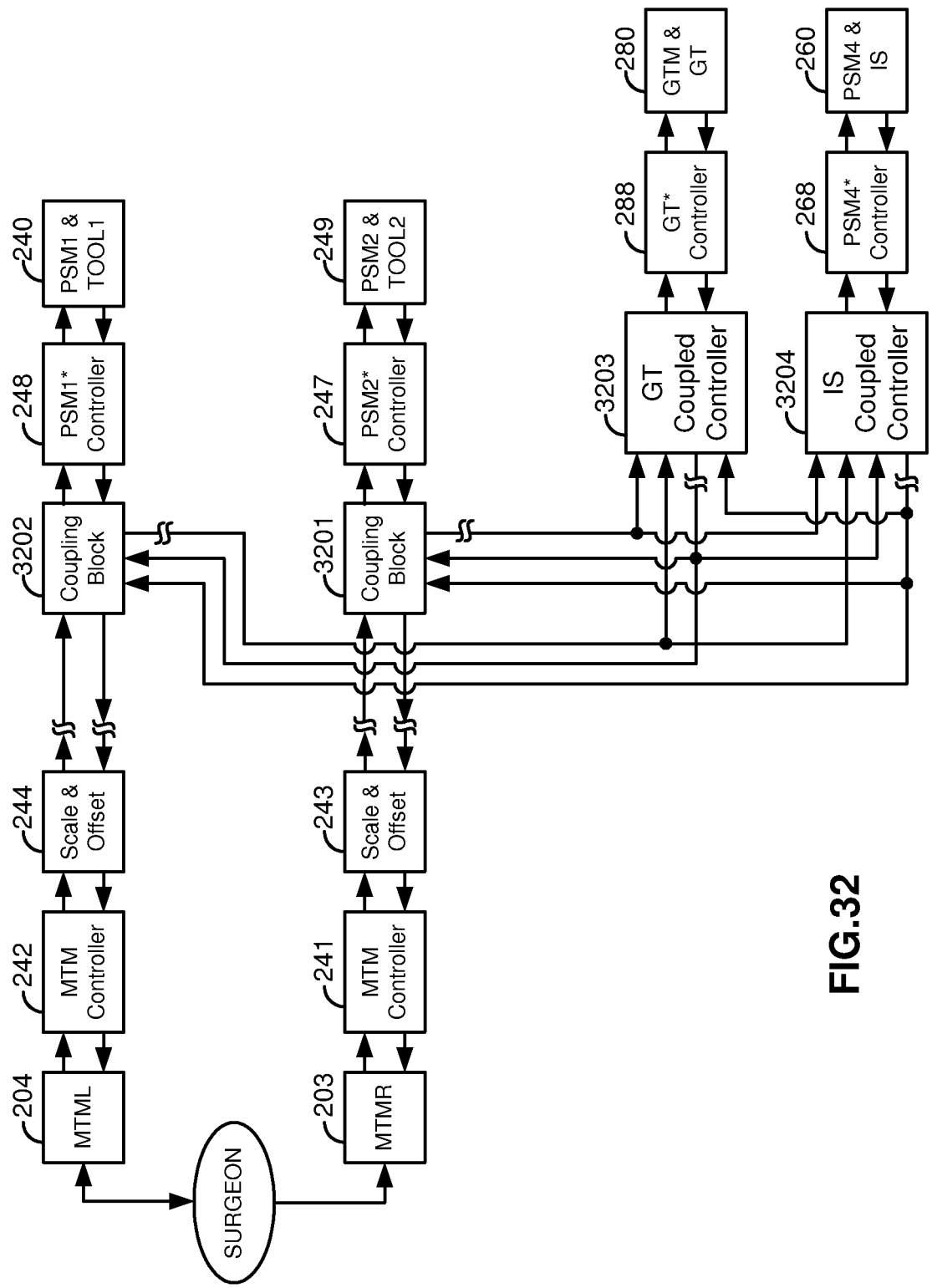
FIG. 32 is a block diagram of a coupled "tool following" mode architecture implemented in the manipulator controllers in the telesurgical system.
Figure 33:
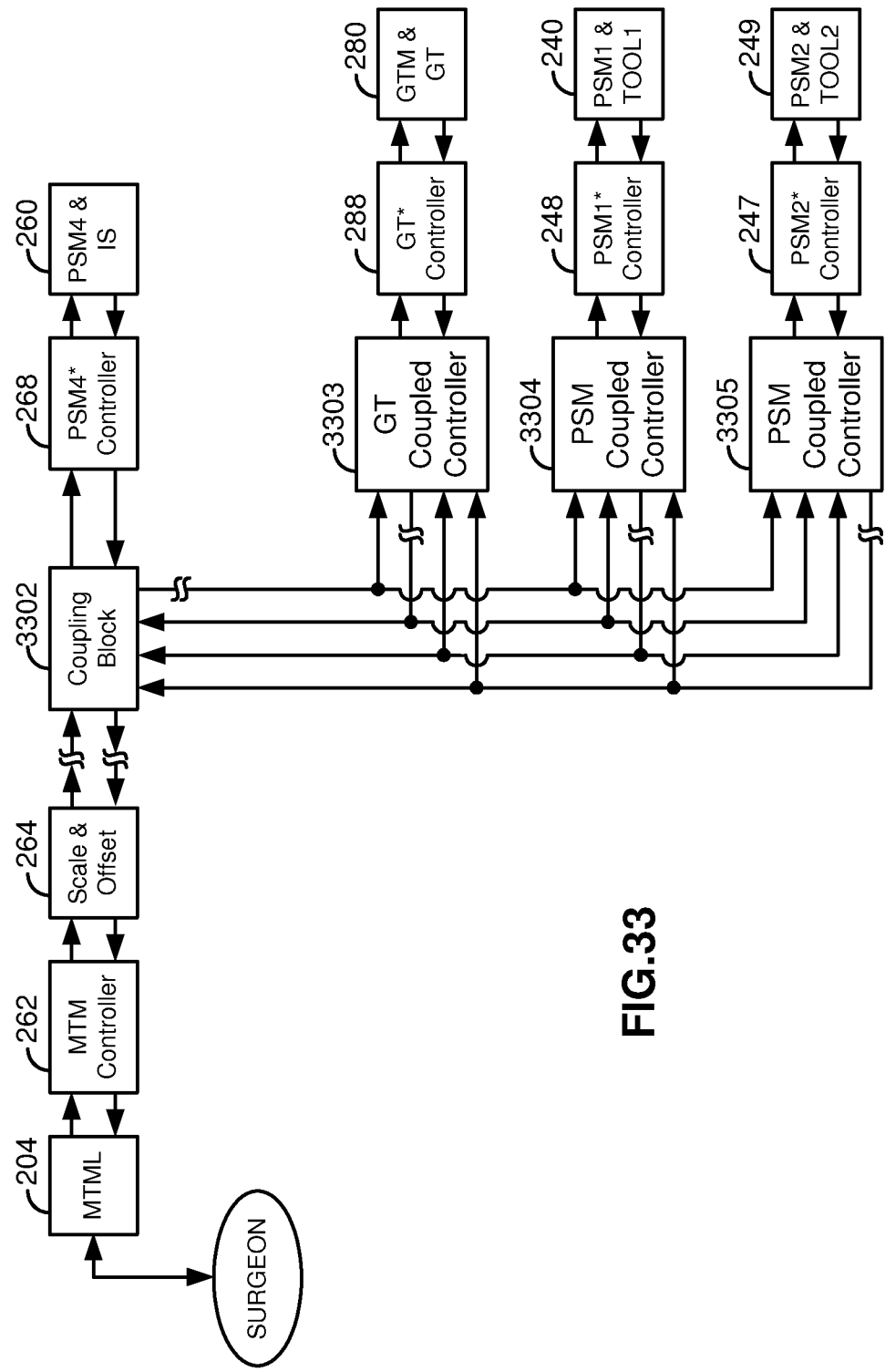
FIG. 33 is a block diagram of a coupled "imaging system" mode architecture implemented in the manipulator controllers in the telesurgical system.
Figure 34:
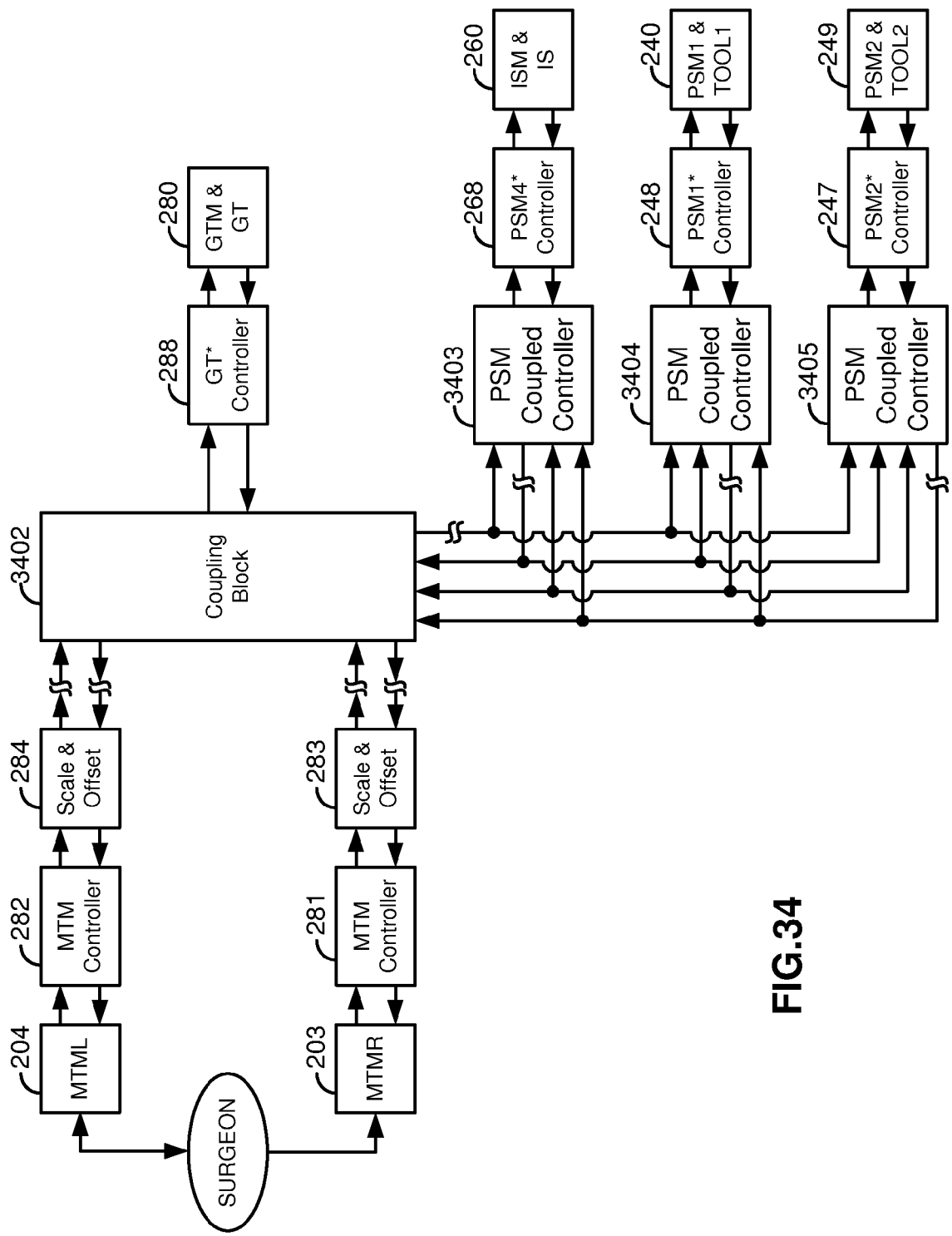
FIG. 34 is a block diagram of a coupled "guide tube" mode architecture implemented in the manipulator controllers in the telesurgical system.

FIGS. 32-34 illustrate aspects of particular coupled control modes where associated devices are directly controlled to accomplish primary objectives and non-associated devices are indirectly controlled to accomplish secondary objectives. In particular, FIG. 32 illustrates a coupled "tool following" mode example in which the left and right master input devices 204,203 are respectively associated with the first and second tools while information of their commanded movement is made available by coupling blocks 3202,3201 connected to data pick-off points of their respective master/slave control systems to coupled controllers 3204,3203 of the imaging system and the guide tube so that they may perform desired "secondary" objectives; FIG. 33 illustrates a coupled "imaging system" mode example in which the left master input device 204 is associated with the imaging system while information of its commanded movement is made available by a coupling block 3302 connected to data pick-off points of its master/slave control system to coupled controllers 3304,3305,3303 of the first tool, second tool, and guide tube so that they may perform desired "secondary" objectives; and FIG. 34 illustrates a coupled "guide tube" mode example in which the left and right master input devices 204,203 are associated with the guide tube while information of its commanded movement is made available by a coupling block 3402 connected to data pick-off points of its master/slave control system to coupled controllers 3404,3405,3403 of the first tool, second tool, and imaging system so that they may perform desired "secondary" objectives. Note that in these coupled mode examples, the third tool is assumed not to be deployed to simplify the figures.

The coupling blocks and device coupled controllers illustrated in FIGS. 32-34 may be implemented in a distributed fashion as shown so that they are either integrated in or implemented outside their respective controllers or they may be implemented in a centralized fashion so they are integrated into a single unit outside of their respective controllers. To transform the direct "tool following" mode to a corresponding coupled "tool following" mode, coupling blocks 3201, 3202 (as shown in FIG. 32) are coupled to the data pick-off/ receiving points (as shown in FIG. 24). Device coupled controllers 3203,3204, which command and control their respective device controllers to perform secondary objectives, are coupled at data pick-off/receiving points of their respective device controllers and to the coupling blocks 3202, 3201 so that they may receive and send information back and forth as indicated by the arrows in FIG. 32. Likewise, to transform the direct "imaging system" mode to a corresponding coupled "imaging system" mode, coupling block 3302 (as shown in FIG. 33) is coupled to the data pick-off/receiving points (as shown in FIG. 26). Device coupled controllers 3303,3304,3305, which command and control their respective device controllers to perform secondary objectives, are coupled at data pick-off/receiving points of their respective device controllers and to the coupling block 3302 so that they may receive and send information back and forth as indicated by the arrows in FIG. 33. Finally, to transform the direct "guide tube" mode to a corresponding coupled "guide tube" mode, coupling block 3402 (as shown in FIG. 34) is coupled to the data pick-off/receiving points (as shown in FIG. 28). Device coupled controllers 3403,3404,3405, which command and control their respective device controllers to perform secondary objectives, are coupled at data pick-off/receiving points of their respective device controllers and to the coupling block 3402 so that they may receive and send information back and forth as indicated by the arrows in FIG. 34.

Figure 36:
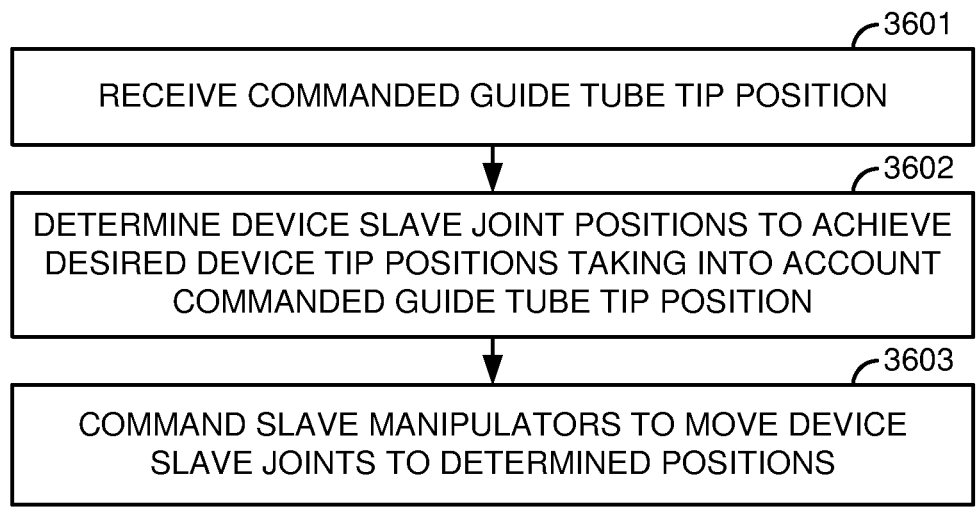
Figure 37:
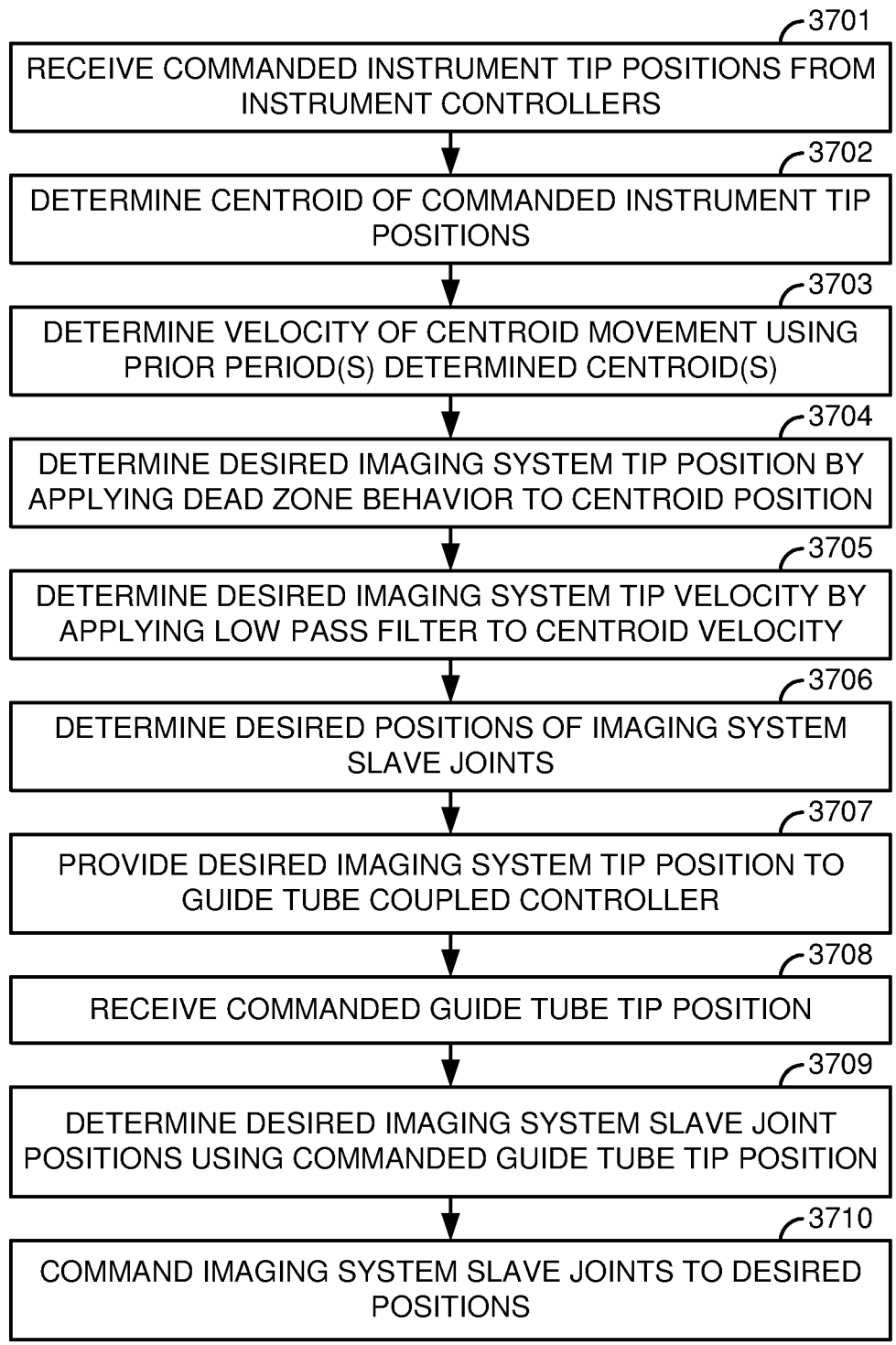
Figure 38:
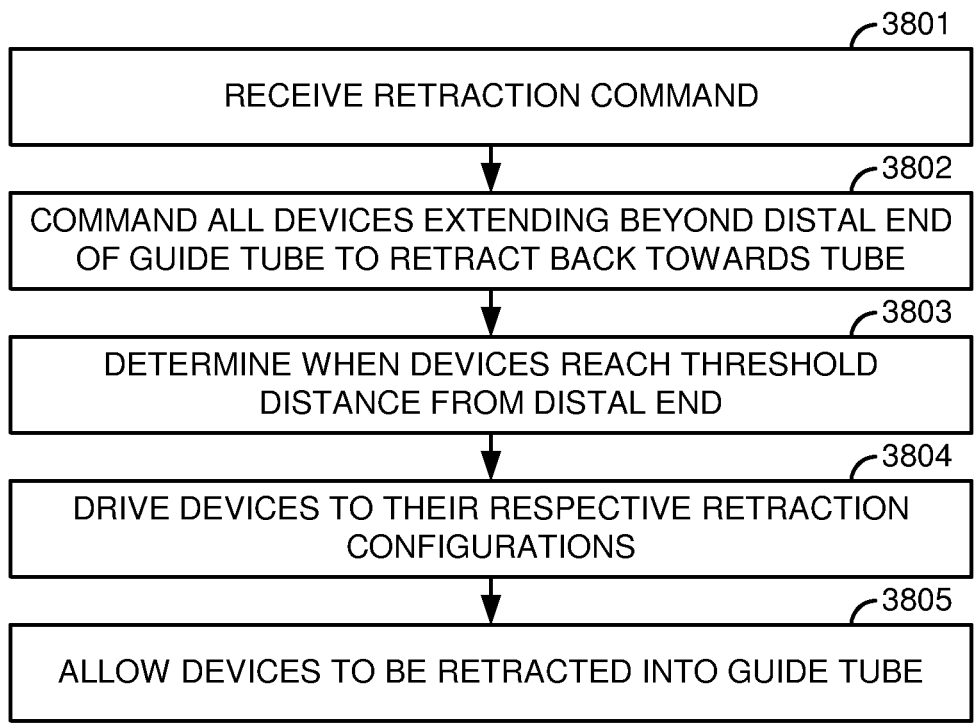
FIG. 38 is a flow diagram for a guide tube coupled control mode example.
Figure 40:
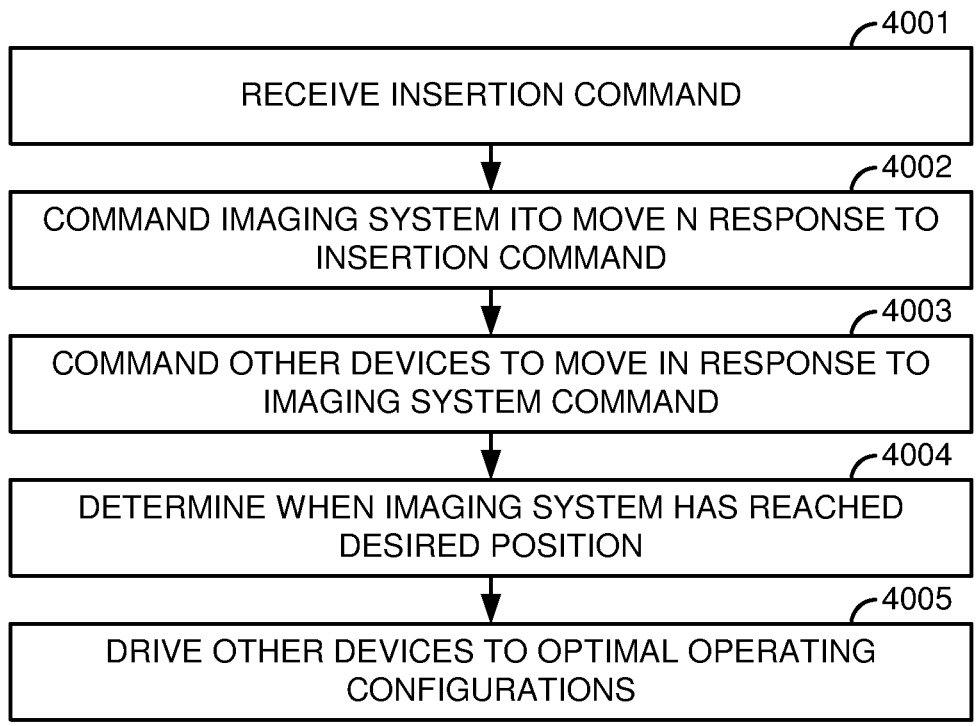
FIG. 40 is a flow diagram for an imaging system coupled control mode example.

FIGS. 35-40 are flow diagrams illustrating examples of coupled control modes. As previously explained, the user interface has three coupled control modes: a mode for the instrument(s), a mode for the imaging system, and a mode for the guide tube. FIGS. 35-37 and 39 are examples of instrument coupled control, FIG. 38 is an example of a guide tube coupled control, and FIG. 40 is an example of an imaging system coupled control. The methods described in reference to FIGS. 35-40, as well as various controllers and other processing units described herein are preferably implemented in processor 220 as described in reference to FIG. 4.

Figure 35:
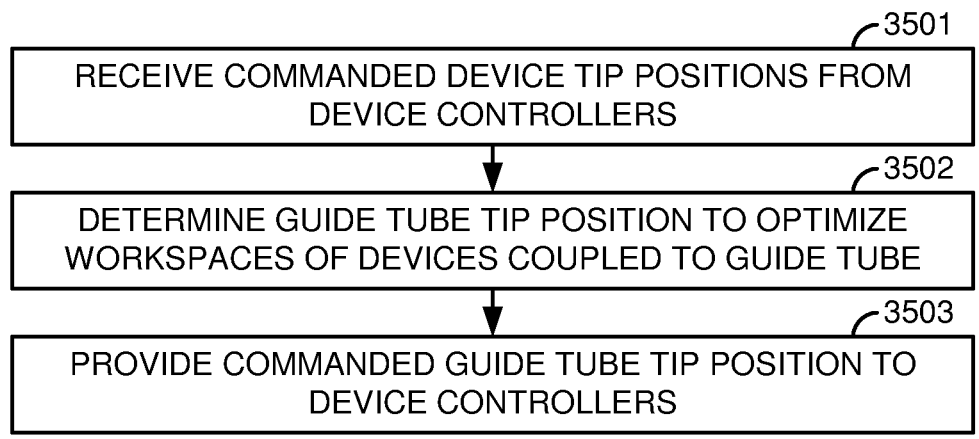
FIGS. 35-37 are flow diagrams for an instrument coupled control mode example.

FIGS. 35-36 illustrate a first part of an example of instrument coupled control in which the workspaces of articulated devices that are coupled to a guide tube and extendable beyond a distal end of the guide tube are optimized. FIG. 6 is one example of such an instrument assembly. Although the present example describes use of a guide tube for optimizing workspaces of articulated devices used to perform a medical procedure, it is to be appreciated that aspects of the invention are also applicable to any base coupled to the articulated devices so that the articulated devices move when the base moves. As an example, the patient side support system 2104, which is described in reference to FIGS. 1-3, may also function as such a base if rotational setup joints 2114a, 2114b are actively drivable.

Referring first to FIG. 35, in 3501, the guide tube coupled controller 3203 (e.g., the motion coordinator 2202 or the guide tube optimizer/controller 2228, depending upon whether a centralized or distributed coupled mode architecture is employed), that is operating at the time in an instrument coupled control mode, receives commanded device tip positions from coupling blocks and coupled controllers of all devices that are coupled to the guide tube (i.e., devices that move when the guide tube moves). For example, a device may be coupled to the guide tube if it is disposed within the guide tube or if it is otherwise physically attached to the guide tube. As used herein (except in places where the context of the description clearly indicates otherwise), the phrase "device tip position" means information indicative of the Cartesian coordinates in a fixed reference frame for the device's most distal joint and an orientation determined by an angular position of the most distal joint.

In 3502, the guide tube coupled controller 3203 uses the received commanded device tip positions to determine a guide tube tip position that optimizes workspaces of the devices coupled to the guide tube while their respective controllers maintain their device tip positions. Since the optimization function requires knowledge of the range of motion limits and kinematics of the devices, as well as the current tip positions of the guide tube and the devices, such range of motion and kinematics information is preferably provided to the guide tube coupled controller 3203 either at system startup or other convenient time in a conventional manner while current tip positions of the devices are provided during operation by the device coupling blocks and coupled controllers as previously described. To determine the desired guide tube tip position, each of the device controllers may provide a desired Cartesian pose for its device so that the guide tube coupled controller solves the kinematics in such a way as to have the guide tube tip positioned so as to allow the device's joints to be configurable as close as possible to its desired pose while not moving its tip from the desired tip position.

Preferably such optimization is performed by minimizing a cost function using ranges of motion of the devices and selected weightings. For example, weight values may be selected so that maximizing the ranges of motions of the instruments 2231,2241 being directly controlled is more heavily weighted (i.e., having higher priority) than maximizing the range of motion of the imaging system 2261 and any other device whose tip is being held in place (i.e., held or "soft-locked" in position by its controller). In 3503, the determined guide tube tip position is then provided to the guide tube controller 2272 to drive the guide tube 2271 to the determined tip position and to the device controllers 2233, 2243,2263 so that they may drive their respective devices 2231,2241,2261 to articulated joint configurations that optimize their respective workspaces as described in reference to FIG. 36 as follows.

Referring now to FIG. 36 to describe complementary actions performed by the device controllers of devices coupled to the guide tube, in 3601, the commanded position of the guide tube 2271 is received from the guide tube coupled controller. In 3602, the device controllers generate updated joint position commands for their respective slave manipulators to accommodate the new guide tube position while satisfying commanded device tip positions. For the instruments 2231,2241, which are associated with the input devices 204, 203 under instrument coupled control mode, the commanded device tip positions correspond to tip positions commanded by the input devices 204,203. For the imaging system 2261 or another instrument 2251, which are not associated at the time with the input devices 204,203, the commanded device tip positions are their current tip positions so that the tips of these non-associated devices are effectively held in place. In 3603, the device controllers provide the updated joint position commands to their respective slave manipulators so that the device workspaces are optimized.

FIG. 37 illustrates an optional second part of the example in which movement of the imaging system 2261 is coupled to movement of the instruments 2231,2241 so that the instruments are well placed in a field of view of the imaging system. Whereas the first part of the example described in reference to FIGS. 35-36 addresses the secondary objective of optimizing the workspaces of devices coupled to the guide tube and extendable beyond the distal end of the guide tube, the second part of the example addresses the secondary objective of optimizing the view of the device tips in images captured by the imaging system.

Referring now to FIG. 37, in 3701, the imaging system coupled controller 3204 (e.g., the motion coordinator 2202 or the imaging system optimizer/controller 2226, depending upon whether a centralized or distributed coupled mode architecture is employed), that is operating at the time in an instrument coupled control mode, receives commanded device tip positions from all device controllers. In 3702, the imaging system coupled controller determines a centroid of the commanded instrument tip positions and in 3703, it determines a centroid velocity using differences in centroid positions determined in the present and previous digital process periods. In 3704 and 3705, tremor filtering is performed to determine a desired imaging system tip position and velocity by respectively applying a dead zone behavior to the centroid position and a low pass filter to the centroid velocity.

In 3706, the imaging system coupled controller 3204 then determines desired joint positions for the imaging system 2261 using inverse kinematics of the articulated imaging system 2261 and the current tip position of the guide tube 2271. In 3707, the imaging system coupled controller determines an imaging system tip position corresponding to the modified slave joint positions using forward kinematics of the imaging system 2261 and provides the determined imaging system tip position to the guide tube coupled controller 3203. Note that the imaging system tip position determined in 3707 should be the same as the desired imaging system tip position in 3704 unless joint limits or singularities were encountered in 3707, in which case, they would be different in order to avoid the limits or singularities. The guide tube coupled controller then processes the imaging system tip position along with the instrument tip positions according to the first part of the example as described in reference to FIG. 35 to generate a guide tube tip position that optimizes workspaces of the instruments and imaging system. In 3708, the imaging system coupled controller 3204 receives the commanded guide tube tip position from the guide tube coupled controller 3203 and uses it in 3709 to determine commanded slave joint positions by applying the imaging system tip position determined in 3707 and the modified guide tube tip position to the same equations and limits used in performing 3706. In 3710, the commanded slave joint positions determined by the imaging system controller 2263 are then provided as actuator commands to the imaging system manipulator 2262 to manipulate or move the imaging system 2261 accordingly.

Upon completion of a medical procedure, all medical devices used during the procedure should be retracted back out of the patient. Rather than doing this one at a time using direct control modes, it is advantageous to retract all devices at the same time using coupled control modes. In particular, by retracting one device under direct control, it is desirable that all other devices follow in retraction under coupled control while addressing secondary objectives such as avoiding collisions with each other and/or the patient anatomy during the retraction. In addition, before retracting each device into its guide tube, it is necessary to first place the device in a retraction configuration so that it may be retracted into the guide tube. For example, the retraction instrument 3108 depicted in FIG. 21 can only be fully retracted into channel 3106c of guide tube 3102 after each of its links 3112a-3112d is aligned with the channel 3106c. Thus, it is desirable to automatically drive each of the devices into its retraction configuration before the device enters its guide tube. This applies to the device being retracted under direct control as well as the devices being retracted indirectly through coupled control modes.

Conversely, before performing a medical procedure, all medical devices to be used during the procedure should be inserted into the patient. Rather than doing this one at a time using direct control modes, it is advantageous to insert all devices at the same time using coupled control modes. In particular, by inserting one device under direct control, it is desirable that all other devices follow in insertion under coupled control while addressing secondary objectives such as avoiding collisions with each other and/or the patient anatomy during the insertion. In addition, after the instruments are inserted into the patient and they reach the work site, it is useful to place the instruments into configurations that optimize their workspaces. It is also useful for the working ends of the instruments to be well placed in a field of view of an imaging system. Thus, it is desirable to automatically drive each of the instruments into its optimal configuration after the imaging system reaches a desired viewing point at the work site.

FIG. 38 illustrates an example of using coupled control for retracting medical devices into a guide tube. Although any one of the devices may be directly controlled while the others are indirectly controlled for retraction into the guide tube, the example employs a virtual degree of freedom (DOF) of the guide tube manipulator for controlling the retraction. Since all devices are coupled to the guide tube, all devices move as the guide tube moves. The guide tube manipulator in this example, however, doesn't have an actuator for insertion/retraction, so it effects a virtual insertion/retraction DOF by causing the devices to be moved in the desired insertion/retraction direction by passing the guide tube insertion/retraction command to each of the device controllers while the guide tube remains in place.

In 3801, the guide tube coupling block 3402 periodically receives conventional time-sampled output from its associated Surgeon manipulated input device(s) that indicates in this case that the guide tube is to be retracted backward (e.g., away from a work site) along its longitudinal axis. In 3802, the coupling block 3402 relays the received retraction commands to the other device coupled controllers so that they in turn, command their respective device manipulators to retract their respective devices in the desired retraction direction from their positions at the time.

In 3803, each of the device controllers (i.e., other than the guide tube controller) determines when the proximal end of the most proximal rotated link of its respective device is within a threshold distance "TH" from the distal end of the guide tube. The threshold distance "TH" may be determined, for example, by taking into account the current rotation angle of the most proximal rotated link, the rate at which the retraction is being commanded by the Surgeon on the input device, and the clearance between the "straightened out" device and the channel through which the device extends through in the guide tube. In particular, the threshold distance "TH" is selected so that each of the devices may be retracted back into the guide tube without striking the ends or sides of its respective channel through which it is disposed.

The distance between the proximal end of the most proximal rotated link of device and the distal end of the guide tube may be determined in a conventional manner by determining a first vector that extends from a remote center "RC" (i.e., a pivot point of the guide tube) to the distal end of the guide tube, determining the most proximal rotated link of the device, determining a second vector that extends from the remote center "RC" to the most proximal joint rotating the most proximal rotated link of the device, and determining the distance between the proximal end of the most proximal rotated link of a device and the distal end of the guide tube from the difference between the first and second vectors.

In 3804, each of the device controllers (i.e., other than the guide tube controller) drives its device to a retraction configuration (i.e., a joint and link configuration that allows the device to be fully retracted into the guide tube) upon determining that the proximal end of the most proximal rotated link of its respective device is within the threshold distance "TH" from the distal end of the guide tube. The rate that the device is driven to its retraction configuration is determined at least in part by the rate at which the output of the input device is changing in the insertion/retraction commanded direction so that collisions between the device and the guide tube are avoided. In addition, possible collisions with other devices and/or the patient are also to be avoided and taken into account as each of the device controllers drives its device to its retraction configuration. In 3805, once each device is determined by its respective device controller to be in its retraction configuration, the device controller allows its respective device to be retracted into its channel in the guide tube in response to retraction commands issued from the input device(s) associated at the time with the guide tube.

Since the image capturing end of the imaging system is generally positioned closer to the distal end of the guide tube than the instruments so that the working ends of the instruments and the work site are well positioned within the field of view of the imaging system, the most proximal rotated link of the imaging system will generally be the first rotated link of the group of devices extending beyond the distal end of the guide tube to reach the threshold distance "TH" from the distal end when the group of devices is being retracted. As the most proximal rotated link of each of the other devices reaches the threshold distance "TH" from the distal end of the guide tube, its device controller drives its device to its retraction configuration.

As an alternative to the method described in reference to 3803-3804, rather than waiting until the most proximal rotated link of each device reaches a threshold distance "TH" from the distal end of the guide tube before the device controller starts driving the device to its retraction configuration, each of the device controllers may start driving its device to the retraction configuration immediately upon receiving a command indicating desired movement in the retraction direction. In this case, each device controller is configured to drive its device to its retraction configuration in a manner that ensures that any rotated link of the device is properly aligned to freely enter the device's channel prior to its entry into the channel while avoiding harm to the patient and collisions with other devices.

While driving the imaging system to its retraction configuration, it is important to keep in mind that the imaging system controller uses the received information of the position of the associated instrument's end effector to command movement of its image capturing end to maintain the end effector in its field of view. Since the operator is viewing the image captured by the image capturing end on a display screen while moving the input device, the operator may become disoriented and/or move the input device in an incorrect manner to properly command retraction of its associated instrument. To compensate for such a non-intuitive experience, the reference frames (i.e. blocks 303 and 312 of FIG. 23) used to compute kinematics of the master and slave manipulators (i.e., blocks 302 and 311 of FIG. 23) are modified such that the position/orientation of the master with respect to the display screen being viewed by the operator constantly corresponds to the position and orientation of the tip (e.g., point on the end effector) of the associated instrument with respect to the tip (e.g., point on the image capturing end) of the imaging system.

In the event that a device controller subsequently receives an insertion command (i.e., a command to move the device in a direction extending away from the distal end of the guide tube), the device controller may automatically drive the device to a desired operational configuration. The desired operational configuration may be a preferred configuration stored in a memory device associated with one or more processors that implement the various controllers and processes described herein. Alternatively, it may be a previously assumed operational configuration that has been stored the memory device. As an example of this latter case, the device joint positions for the operational configurations of the devices just prior to initiating their retraction towards the guide tube may be stored in the memory device so that if the Surgeon decides to re-insert the devices (or their replacement devices after a tool exchange procedure), their device controllers may automatically drive the devices back to the stored operational configurations.

In some instances a surgical instrument is removable and may be replaced with a different surgical instrument that has a structure similar to instrument but a different end effector so as to perform a different surgical task. Accordingly, a single guide tube may be used for one or more interchangeable surgical instruments. In one instance the end effector of the surgical instrument is removable so that it may be readily exchanged with another. In another instance, a surgical accessory such as a clip or suturing material may be provided to a grasping end effector for delivery to the work site while guide tube remains in the patient. A convenient way of performing such end effector exchange (also referred to herein as a "tool exchange") or providing such a surgical accessory to a retracted grasping end effector is to use a fenestrated guide tube wherein one or more cut-outs are provided in the guide tube in a part externally extending out of the patient while another part of the guide tube extends internally into the patient through the entry aperture.

Figure 39:
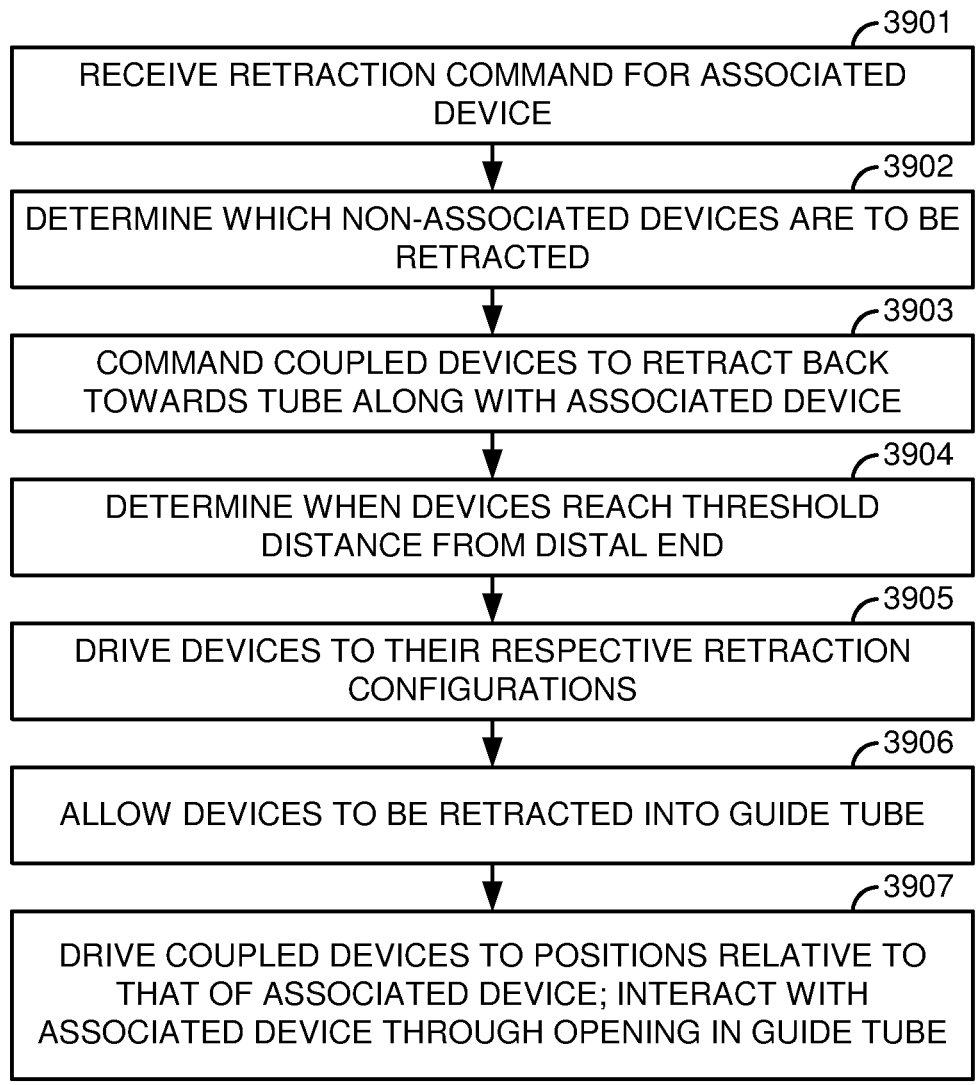
FIG. 39 is a flow diagram for a tool retraction into a fenestrated guide tube for a tool exchange or accessory providing operation in a coupled "tool following" mode example.

FIG. 39 illustrates an example of using coupled control for retracting medical devices into a fenestrated guide tube for a tool exchange or other purpose such as delivering a surgical accessory to the work site. In the example, a plurality of devices including an imaging system and at least two instruments extend through and beyond the distal end of a guide tube.

In 3901, a retraction command is received from an input device associated with an instrument to be retracted (referred to herein as the "associated instrument"). The retraction command is indicated by movement of the input device in a direction that would result in commanding the associated instrument to be retracted back towards and/or into a distal end of the guide tube. As previously described in reference to FIGS. 23 and 32, sensed joint movement of the input device is processed by the instrument's master/slave control system and the resulting commanded state of the distal tip of the associated instrument is picked off at the output of the scale & offset block and provided along with information identifying the associated instrument (and in particular, its placement in the guide tube) through a coupling block to coupled controller blocks of other devices in the system.

In 3902, a determination is made within each of the coupled controller blocks whether its associated device is to be retracted back along with the associated instrument. In the case of the coupled controller block for the imaging system, the determination is affirmative so that the operator may continuously view the working end of the associated instrument as it is retracted back into the guide tube. In the case of the coupled controller blocks of other devices, the determination takes into account whether their respective instruments would be blocking access to the associated instrument's end effector from an opening in the guide tube through which the tool exchange and providing of a surgical accessory is to take place. If the unretracted instrument would block such access to the associated instrument's end effector through the opening, then the determination for coupled controller block of the blocking instrument would also be affirmative. On the other hand, the determination for coupled controller blocks of non-blocking instruments would be negative.

In 3903, coupled controller blocks making affirmative determinations then relay the received retraction commands to their respective controllers, which in turn, command their respective device manipulators to retract their devices (referred to herein as the "coupled devices") in the desired retraction direction from their positions at the time.

In 3904, each of the retracting device controllers (for both the associated device and the coupled devices) determines when the proximal end of the most proximal rotated link of its respective device is within a threshold distance "TH" from the distal end of the guide tube in the manner described in reference to 3803 of FIG. 38.

In 3905, each of the device controllers then commands its respective device manipulator to drive its device to a retraction configuration (i.e., a joint and link configuration that allows the device to be fully retracted into the guide tube) upon determining that the proximal end of the most proximal rotated link of its respective device is within the threshold distance "TH" from the distal end of the guide tube in the manner described in reference to 3804 of FIG. 38 (including compensating for the moving imaging system as described therein).

In 3906, once each device being retracted is determined by its respective device controller to be in its retraction configuration, the device controller allows its respective device to be retracted into its channel in the guide tube in response to retraction commands issued from the input device.

In 3907, once the operator determines that the end effector of the associated instrument is in proper position relative to the opening in the fenestrated guide tube, movement of the input device and consequently, the associated instrument is stopped. The imaging system, however, may continue to move to ensure that the associated instrument's end effector is properly within its field of view. In addition, the blocking instrument continues to move until it no longer blocks the access to the associated instrument's end effector through the opening in the fenestrated guide tube. After access to the associated instrument's end effector is clear from the opening, then an exchange of end effectors may be performed and/or a surgical accessory may be provided to the end effector as the imaging system views the activity with the associated instrument's end effector.

FIG. 40 illustrates an example of using coupled control for extending medical devices out of the guide tube and inserting it towards a work site. Although any one of the devices may be directly controlled while the others are indirectly controlled for insertion towards the work site, the example assumes the imaging system is being directly controlled for insertion while the instruments are indirectly controlled through coupled control to follow the image capturing end of the imaging system. Using the imaging system to lead the insertion is advantageous since it allows the surgeon to see the path towards the work site.

Control during insertion may be accomplished, for example, in a manner similar to telemanipulated endoscope control in the da Vinci® Surgical System—in one aspect the surgeon virtually moves the image with one or both of the masters; she uses the masters to move the image side to side and to pull it towards herself, consequently commanding the imaging system and its associated instrument assembly (e.g., a flexible guide tube) to steer towards a fixed center point on the output display and to advance inside the patient. In one aspect the camera control is designed to give the impression that the masters are fixed to the image so that the image moves in the same direction that the master handles are moved, as in the da Vinci® surgical system. This design causes the masters to be in the correct location to control the instruments when the surgeon exits from camera control, and consequently it avoids the need to clutch (disengage), move, and declutch (engage) the masters back into position prior to beginning or resuming instrument control. In some aspects the master position may be made proportional to the insertion velocity to avoid using a large master workspace. Alternatively, the surgeon may clutch and declutch the masters to use a ratcheting action for insertion. In some aspects, insertion (e.g., past the glottis when entering via the esophagus) may be controlled manually (e.g., by hand operated wheels), and automated insertion (e.g., servomotor driven rollers) is then done when the distal end of the surgical instrument assembly is near the surgical site. Preoperative or real time image data (e.g., MRI, X-ray) of the patient's anatomical structures and spaces available for insertion trajectories may be used to assist insertion.

In 4001, the imaging system controller receives an insertion command from an associated input device. In 4002, the imaging system controller commands the imaging system manipulator to move the imaging system in response to insertion command, while in 4003, the imaging system controller provides the movement command to other device coupled controllers so that they may also command their respective devices to move in response to the imaging system commanded movement. In 4004, the imaging system controller determines whether the image capturing end of the imaging system has reached its desired position. This determination may be performed either automatically based upon programmed criteria or it may be indicated through action taken by the Surgeon such as depressing a button on the input device associated with the imaging system at the time. In 4005, after the imaging system controller has determined that the image capturing end of the imaging system has reached its desired position it provides an indication of such to the instrument coupled controllers (e.g., the motion controller 2202 or the instrument optimizer/controllers 2224*a*,2224*b*,2224*c*, depending upon which instruments are to be deployed and whether a centralized or distributed coupled mode architecture is employed) so that the instrument controllers in response thereof command their respective instrument manipulators to move their instruments into their optimal operating configurations. Placing the devices in their optimal operating configurations in this case generally involve placing the working ends of the instruments within the field of view of the imaging system and optimizing the workspaces of the instruments (such as shown, for example, in FIG. 18).

As apparent from the coupled control mode examples described herein, not all position information provided to the motion coordinator or the device optimizer/controllers is used. Therefore, either more information than is necessary is transmitted between the device controllers with some of it being ignored or only necessary information is transmitted. Although the descriptions of FIGS. 30-31 may indicate the former, it is to be appreciated that the implementations described therein may also apply to the latter.

It is further noted that any time the image capturing end of the imaging system moves as a coupled device, the image reference frame used by the Surgeon for master/slave teleoperation changes and such change may affect the ability of Surgeon to perform precise surgical motions. In such case, a number of actions may be taken for large motions of the imaging capturing end of the imaging system. For example, haptic feedback may be provided on the input device to assist the Surgeon to take appropriate action, or a computer generated auxiliary view of devices extending out of a distal end of a guide tube may be provided from a stable (e.g., fixed) perspective and relied upon by the Surgeon for master/slave teleoperation, or the images captured by the imaging system may be modified in real-time to maintain an intuitively correct master/slave mapping with the modified images displayed on the surgeon console.

These descriptions of examples of various minimally invasive surgical systems, assemblies, and instruments, and of the associated components, are not to be taken as limiting. It should be understood that many variations that incorporate the aspects described herein are possible. For example, various combinations of rigid and flexible instruments and instrument components, and of guide tubes and guide tube components, fall within the scope of this description. The claims define the invention.

What is claimed is:

1. A robotic system comprising:
   a master input device;
   first and second slave manipulators;
   means for commanding the second slave manipulator to move in response at least in part to commanded movement of the first slave manipulator when the first slave manipulator moves in response to movement of the master input device; and
   means for commanding the first slave manipulator to move in response at least in part to commanded movement of the second slave manipulator when the second slave manipulator moves in response to movement of the master input device.

2. The robotic system according to claim 1, wherein the first slave manipulator is adapted to move an instrument coupled to a base and the second slave manipulator is adapted to move the base, and wherein the means for commanding the second slave manipulator commands the second slave manipulator to move the base so as to optimize a workspace of the instrument when the first slave manipulator is commanded to move the instrument in response to movement of the master input device.

3. The robotic system according to claim 2, wherein the means for commanding the first slave manipulator commands the first slave manipulator to maintain a working end of the instrument at a desired position and orientation when the second slave manipulator is commanded to move the base in response to movement of the master input device.

4. The robotic system according to claim 3, wherein the base comprises a guide tube to which the instrument is coupled so as to be extendable beyond a distal end of the guide tube and to move when the guide tube moves.

5. The robotic system according to claim 1, wherein the first slave manipulator is adapted to move an instrument and the second slave manipulator is adapted to move an imaging system, wherein the means for commanding the second slave manipulator commands the second slave manipulator to move the imaging system so as to maintain a working end of the instrument within a field of view of the imaging system when the first slave manipulator is commanded to move the instrument in response to movement of the master input device.

6. The robotic system according to claim 5, wherein the means for commanding the first slave manipulator commands the first slave manipulator to move the instrument so as to follow movement of the imaging system when the second slave manipulator is commanded to move the imaging system in response to movement of the master input device.

7. The robotic system according to claim 1, wherein the first slave manipulator is adapted to move an imaging system coupled to a base and the second slave manipulator is adapted to move the base, and wherein the means for commanding the second slave manipulator commands the second slave manipulator to move the base so as to optimize a workspace of the imaging system when the first slave manipulator is commanded to move the imaging system in response to movement of the master input device.

8. The robotic system according to claim 7, wherein the means for commanding the first slave manipulator commands the first slave manipulator to move the imaging system so as to maintain an image capturing end of the imaging system at a desired position and orientation when the second slave manipulator is commanded to move the base in response to movement of the master input device.

9. The robotic system according to claim 8, wherein the base comprises a guide tube to which the imaging system is coupled so as to be extendable beyond a distal end of the guide tube and to move when the guide tube moves.

10. A robotic system comprising:
    a first instrument;
    a base that the first instrument is coupled to so that the first instrument moves when the base moves;
    a base controller configured to cause the base to be moved so as to optimize a workspace of the first instrument in response to commanded movement of the first instrument; and
    a first instrument controller configured to cause the first instrument to be moved according to the commanded movement of the first instrument while automatically compensating for movement of the base.

11. The robotic system according to claim 10, further comprising:
    a second instrument coupled to the base so that the second instrument moves when the base moves;
    wherein the base controller is configured to cause the base to be moved so as to continuously optimize workspaces of both the first and second instruments in response to commanded movement of the first and second instruments; and
    a second instrument controller configured to cause the second instrument to be moved according to commanded movement of the second instrument while automatically compensating for movement of the base.

12. The robotic system according to claim 11, further comprising:
    an imaging system having an image capturing end and coupled to the base so that the imaging system moves when the base moves;
    wherein the base controller is configured to cause the base to be moved so as to optimize workspaces of both the first and second instruments subject to a constraint that maintains a position and orientation of the image capturing end relative to a fixed reference frame.

13. The robotic system according to claim 12, further comprising:
    a surgeon console having operator manipulatable first and second input devices;
    wherein the base controller is configured to determine whether movement of the base to optimize workspaces of the first and second instruments requires movement from the maintained position and orientation of the image capturing end, and
    wherein the base controller is configured to provide an indication of such required movement to an operator of at least one of the first and second input devices.

14. The robotic system according to claim 13, wherein the indication is at least one of visual, audio, and haptic indications.

15. The robotic system according to claim 13, wherein the base controller is configured to cause the base to be moved so as to optimize workspaces of the first and second instruments as a priority over an imaging system controller configured to maintain the position and orientation of the image capturing end following receipt of an indication of such priority from the operator of the at least one of the first and second input devices.

16. The robotic system according to claim 11, further comprising:
an imaging system having an image capturing end, the imaging system being coupled to the base so that the imaging system moves when the base moves; and
an imaging system controller configured to cause the imaging system to be moved so as to maintain a first end effector of the first instrument and a second end effector of the second instrument within a field of view of the image capturing end as the first and second instruments are commanded to move.

17. The robotic system according to claim 16, wherein the imaging system controller is configured to cause the image capturing end to move so as to maintain the first and second end effectors within the field of view by calculating and causing maintenance of a set point for manipulation of the imaging system based upon a calculated centroid of the first and second end effectors in an image from the image capturing system.

18. The robotic system according to claim 17, wherein the imaging system controller is configured to compute the set point by applying the calculated centroid to a low pass filter and applying a dead-zone behavior in causing movement of the imaging system.

19. A robotic system comprising:
a plurality of devices, wherein each of the plurality of devices is manipulated by a corresponding one of a plurality of slave manipulators;
a master input device; and
means for concurrently commanding the plurality of slave manipulators to move the plurality of devices in a common degree-of-freedom direction in response to movement of the master input device.

20. The robotic system according to claim 19, wherein the common degree-of-freedom direction is a direction in which distal tips of the plurality of devices move in parallel directions.

21. The robotic system according to claim 19, further comprising:
a guide tube through which the plurality of devices is disposed so as to be extendable beyond a distal end of the guide tube, wherein the common degree-of-freedom is defined relative to the guide tube.

22. The robotic system according to claim 21, wherein the common degree-of-freedom is movement in a surge direction relative to a distal end of the guide tube.

23. The robotic system according to claim 21, further comprising:
a plurality of device controllers, wherein each of the plurality of device controllers is configured to control movement of a corresponding one of the plurality of slave manipulators; and
a guide tube controller configured to control movement of the guide tube in a plurality of degrees-of-freedom not including translational motion parallel to a longitudinal axis of the guide tube, wherein the guide tube controller is configured to receive commanded movement from the master input device, wherein the guide tube controller is configured to control movement of the guide tube for commanded movement in the plurality of degrees-of-freedom, and wherein the guide tube controller is configured to command the plurality of device controllers to control movement of the plurality of devices for commanded movement parallel to the longitudinal axis of the guide tube.

24. The robotic system according to claim 23, wherein each of the plurality of slave manipulators is configured to retract its respective device in a proximal direction in response to a retraction command indicated by the commanded movement from the guide tube controller, and wherein each of the plurality of slave manipulators is configured to drive its respective device to a retraction configuration so that its respective device may freely enter the guide tube.

25. The robotic system according to claim 24, wherein each of the plurality of device controllers is configured to determine when a most proximal pitch or yaw rotated link of its respective device is within a threshold distance from the distal end of the guide tube, and wherein each of the plurality of device controllers is configured to drive its respective device to a retraction configuration upon such determination.

26. The robotic system according to claim 23, wherein each of the plurality of device controllers is configured to extend its respective device in a distal direction in response to an insertion command indicated by the commanded movement from the guide tube controller.

27. The robotic system according to claim 23, wherein the plurality of device controllers is configured to retract the plurality of devices in unison in a proximal direction in response to a retraction command indicated by the commanded movement from the guide tube controller.

28. The robotic system according to claim 27, wherein each of the plurality of device controllers is configured to drive its respective device of the plurality of devices to a retraction configuration so that the plurality of devices may freely enter the guide tube in response to the retraction command.

29. The robotic system according to claim 23, wherein the plurality of device controllers is configured to extend the plurality of devices in unison in a distal direction in response to an insertion command indicated by the commanded movement from the guide tube controller.

30. The robotic system according to claim 29, wherein each of the plurality of device controllers is configured to drive its respective device of the plurality of devices to an operational configuration defined by information of joint positions stored in a memory device in response to the insertion command.

31. The robotic system according to claim 30, wherein the operational configurations indicate configurations corresponding to information stored in the memory device.

32. The robotic system according to claim 19, wherein one of the plurality of devices comprises an imaging system, and the robotic system further comprises:
a surgeon console having the master input device and a display, wherein images captured by the imaging system are processed and displayed on the display.

33. The robotic system according to claim 32, further comprising:
means for providing haptic feedback on the master input device to indicate movement of an image capturing end of the imaging system.

34. The robotic system according to claim 32, further comprising:
means for providing a computer generated auxiliary view of the plurality of devices as taken from a stable perspective.

35. The robotic system according to claim 32, further comprising:
means for modifying reference frames used for computing kinematics of the master input device and one of the plurality of slave manipulators such that a position and orientation of the master input device with respect to a display viewable by an operator as the operator moves the master input device constantly corresponds to a position and orientation of a tip of a device manipulatable by the one of the plurality of slave manipulators with respect to an image capturing end of the imaging system.

36. The robotic system according to claim 19, further comprising:
a fenestrated guide tube through which the plurality of devices is disposed so as to be extendable beyond a distal end of the fenestrated guide tube, wherein the common degree-of-freedom is movement parallel to a longitudinal axis of the fenestrated guide tube.

37. The robotic system according to claim 36, wherein the means for concurrently commanding the plurality of slave manipulators to move the plurality of devices in a common degree-of-freedom direction in response to movement of the master input device comprises:
means for directly controlling one of the plurality of slave manipulators in response to movement of the master input device; and
means for indirectly controlling another of the plurality of slave manipulators in response to commanded movement of the directly controlled one of the plurality of slave manipulators.

38. The robotic system according to claim 37, wherein the directly controlled slave manipulator of the plurality of slave manipulators manipulates a first instrument, and the indirectly controlled slave manipulator of the plurality of slave manipulators manipulates a second instrument that is interposed between the first instrument and an opening in the fenestrated guide tube when the first instrument is retracted into the fenestrated guide tube, the first and second instruments being in the plurality of devices.

39. The robotic system according to claim 37, wherein the directly controlled slave manipulator of the plurality of slave manipulators manipulates an instrument, and the indirectly controlled slave manipulator of the plurality of slave manipulators manipulates an imaging system, the instruments and the imaging system being in the plurality of devices.

40. The robotic system according to claim 39, further comprising:
means for modifying reference frames used for computing kinematics of the master input device and of the directly controlled slave manipulator of the plurality of slave manipulators such that a position and orientation of the master input device with respect to a display, viewable by an operator as the operator moves the master input device, constantly corresponds to a position and orientation of a tip of the instrument, being controlled by the master input device, with respect to an image capturing end of the imaging system.

41. A robotic system comprising:
a plurality of instruments, each of the plurality of instruments manipulated by a corresponding one of a plurality of slave manipulators;
an imaging system manipulated by an imaging system manipulator;
a master input device; and
means for commanding the plurality of slave manipulators to move their corresponding ones of the plurality of instruments in response to commanded movement of the imaging system when the imaging system manipulator moves in response to movement of the master input device.

42. The robotic system according to claim 41, wherein the means for commanding the plurality of slave manipulators comprises a plurality of subunits, each of the plurality of subunits coupled to a corresponding one of the plurality of slave manipulators, wherein each of the plurality of subunits is configured to command its corresponding one of the plurality of slave manipulators to move in response to movement of the master input device.

43. The robotic system according to claim 41, wherein the means for commanding the plurality of slave manipulators commands individual of the plurality of slave manipulators to move its respective instrument of the plurality of instruments so as to be within a field of view of the imaging system as the imaging system manipulator moves in response to movement of the master input device.

44. The robotic system according to claim 41, wherein the means for commanding the plurality of slave manipulators commands individual of the plurality of slave manipulators to move its respective instrument of the plurality of instruments so as to maximize the respective instrument's available range of motion.

45. The robotic system according to claim 41, further comprising:
a guide tube through which the plurality of instruments and the imaging system are disposed within and extendable beyond a distal end of the guide tube.

46. The robotic system according to claim 45, further comprising:
a guide tube manipulator for manipulating the guide tube; and
means for commanding the guide tube manipulator to move so as to avoid the imaging system from reaching a boundary limit relative to the guide tube as the imaging system manipulator moves the imaging system in response to movement of the master input device.

* * * * *